(12) United States Patent
Hergenrother et al.

(10) Patent No.: US 10,272,099 B2
(45) Date of Patent: Apr. 30, 2019

(54) TUMOR-SELECTIVE COMBINATION THERAPY

(71) Applicants: The Board of Regents of the University of Texas System, Austin, TX (US); The Board of Trustees of the University of Illinois, Urbana, IL (US)

(72) Inventors: Paul J. Hergenrother, Champaign, IL (US); David A. Boothman, Dallas, TX (US); Joseph S. Bair, Mullica Hill, NJ (US); Lifen Cao, Dallas, TX (US); Jinming Gao, Plano, TX (US); Xiumei Huang, Dallas, TX (US); Xiuquan Luo, Plano, TX (US); Xinpeng Ma, Dallas, TX (US); Zachary R. Moore, Dallas, TX (US); Elizabeth I. Parkinson, Champaign, IL (US)

(73) Assignees: The Board of Regents of the University of Texas System, Austin, TX (US); The Board of Trustees of the University of Illinois., Urbana, IL (US)

( * ) Notice: Subject to any disclaimer, the term of this patent is extended or adjusted under 35 U.S.C. 154(b) by 0 days.

(21) Appl. No.: 14/783,344

(22) PCT Filed: Apr. 8, 2014

(86) PCT No.: PCT/US2014/033400
§ 371 (c)(1),
(2) Date: Oct. 8, 2015

(87) PCT Pub. No.: WO2014/168991
PCT Pub. Date: Oct. 16, 2014

(65) Prior Publication Data
US 2016/0030457 A1    Feb. 4, 2016

Related U.S. Application Data

(60) Provisional application No. 61/810,008, filed on Apr. 9, 2013.

(51) Int. Cl.
| | | |
|---|---|---|
| *A61K 31/353* | (2006.01) | |
| *A61K 31/4745* | (2006.01) | |
| *A61K 31/131* | (2006.01) | |
| *A61K 31/706* | (2006.01) | |
| *A61K 45/06* | (2006.01) | |
| *C12Q 1/6886* | (2018.01) | |
| *A61K 31/4738* | (2006.01) | |

(52) U.S. Cl.
CPC ......... *A61K 31/706* (2013.01); *A61K 31/131* (2013.01); *A61K 31/353* (2013.01); *A61K 31/4738* (2013.01); *A61K 31/4745* (2013.01); *A61K 45/06* (2013.01); *C12Q 1/6886* (2013.01); *C12Q 2600/106* (2013.01); *C12Q 2600/158* (2013.01)

(58) Field of Classification Search
CPC .. A61K 31/706; A61K 31/353; A61K 31/131; A61K 45/06; A61K 31/4745
USPC .......................................... 514/27, 292, 454
See application file for complete search history.

(56) References Cited

U.S. PATENT DOCUMENTS

| | | |
|---|---|---|
| 5,716,963 A | 2/1998 | Avendano Lopez et al. |
| 6,809,096 B1 | 10/2004 | Delfourne et al. |
| 2002/0198264 A1 | 12/2002 | Gerson et al. |
| 2004/0001871 A1 | 1/2004 | Boothman et al. |
| 2009/0275608 A1 | 11/2009 | Ossovskaya et al. |
| 2013/0030237 A1 | 1/2013 | Theuer |

FOREIGN PATENT DOCUMENTS

| | | | |
|---|---|---|---|
| JP | 2006-522088 | | 9/2006 |
| JP | 2010-538967 | | 12/2010 |
| JP | 2011-503111 | | 1/2011 |
| WO | WO 2004-087713 | | 10/2004 |
| WO | WO 2008-083107 | | 7/2008 |
| WO | WO 2009-064738 | | 5/2009 |
| WO | WO 2012/037378 | * | 3/2012 |
| WO | WO 2012/040492 | | 3/2012 |
| WO | WO 2013/056073 | | 4/2013 |

OTHER PUBLICATIONS

Hamlet et al. Beckmann Rearrangement Studies of alphaB-Acetylenic Ketoxirnes. Chemical Communications p. 1230-1231, 1970.*
Sun et al. Selective Induction of Necrotic Cell Death in Cancer Cells by β-Lapachone through Activation of DNA Damage Response Pathway. Cell Cycle 5:17, 2029-2035, Sep. 1, 2006. (Year: 2006).*
Bentle et al. Exploiting Novel Calcium-Mediated Apoptotic Processes for the Treatment of Human Breast Cancers with Elevated NQ01 Levels. Annual report, U.S. Army Medical Research and Materiel Command. Award No. W81XWH-04-1-0301. Report Date: Mar. 2005. (Year: 2005).*
Li et al., "Modulating endogenous NQ01 levels identifies key regulatory mechanisms of action of β-lapachone for pancreatic cancer therapy," *Clin. Cancer Res.*, 17(2):275-285, 2011.

(Continued)

*Primary Examiner* — Yih-Horng Shiao
(74) *Attorney, Agent, or Firm* — Parker Highlander PLLC

(57) ABSTRACT

The therapies described herein can be selectively lethal toward a variety of different cancer cell types and cancer conditions in a subject. The combination therapies described herein can be useful for the management, treatment, control, or adjunct treatment of diseases, where the selective lethality is beneficial in chemotherapeutic therapy, particularly where the disease is accompanied by elevated levels of NQO1.

20 Claims, 75 Drawing Sheets

(56) References Cited

OTHER PUBLICATIONS

PCT International Preliminary Report on Patentability issued in International Application No. PCT/US2014/033400, dated Oct. 22, 2015.
PCT International Search Report and Written Opinion issued in International Application No. PCT/US2014/033400, dated Aug. 25, 2014.
Bair et al., "Chemistry and biology of deoxynyboquinone, a potent inducer of cancer cell death," *J. Am. Chem. Soc.*, 132:5469-5478, 2010.
Extended European Search Report issued in European Application No. 14783210.9, dated Nov. 2, 2016.
Huang et al., "An NQO1 substrate with potent antitumor activity that selectively kills by PARP1-induced programmed necrosis," *Cancer Res.*, 72(12):3038-3047, 2012.
Office Action issued in Japanese Application No. 2016-507622, dated Jan. 11, 2018.

* cited by examiner

COMPARISON OF ß-LAP LD$_{50}$ VALUES WITH NQOI ACTIVITY
IN VARIOUS PANCREATIC CANCER CELL LINES

| CELL LINE | ENZYME ACTIVITY (U) | ß-LAP LD$_{50}$ (µM, 2h) | | |
|---|---|---|---|---|
| | | VEHICLE | DIC[1] | BAPTA[2] |
| MIA PaCa-2 | 410 ± 30 | 4.5 ± 0.4 | >20 | >20 |
| KD17-1 | 70 ± 8 | 9.5 ± 0.5 | >20 | >20 |
| KD17-3 | 90 ± 4 | 5.4 ± 0.3 | >20 | >20 |
| KD17-7 | 50 ± 3 | 14.0 ± 0.1 | >20 | >20 |
| KD6 | 200 ± 10 | 4.2 ± 0.1 | >20 | >20 |
| KD8 | 380 ± 10 | 4.2 ± 0.4 | >20 | >20 |
| ASPC-1 | 570 ± 30 | 3.71 ± 0.1 | >20 | >20 |
| CFPAC-1 | 1200 ± 20 | 3.1 ± 0.1 | >20 | 9.5 ± 0.1 |
| BXPC3 | 380 ± 2 | 3.6 ± 0.2 | >20 | 16.7 ± 0.1 |
| HS766T | 870 ± 20 | 7.4 ± 0.5 | >20 | >20 |

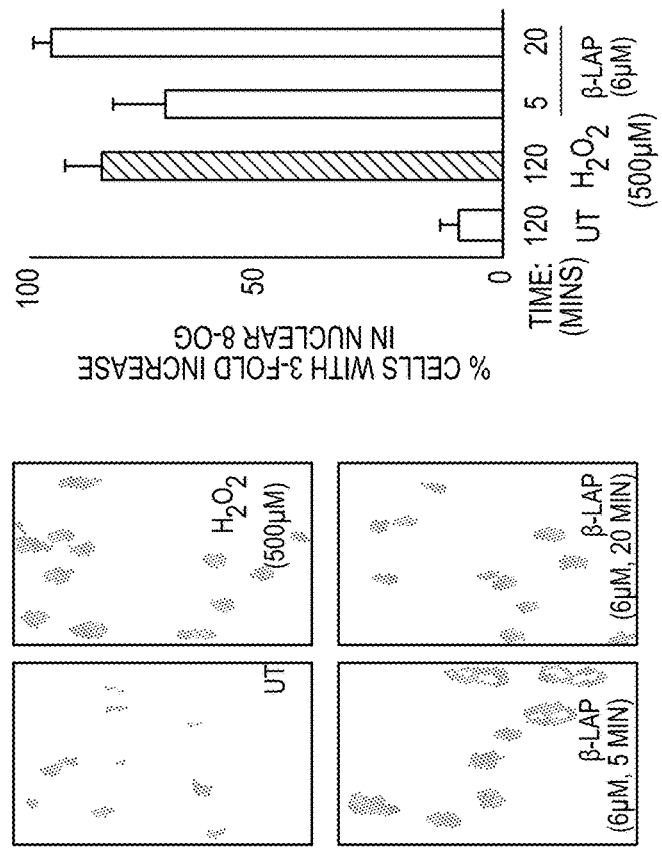
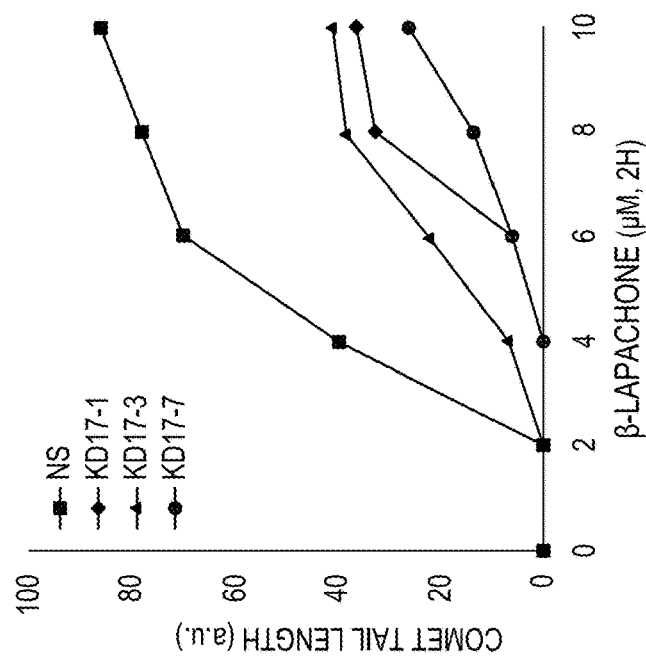
*Figure 4C*
*Figure 4B*

A.

B.

C.

*P<0.01
**P<0.001

- CONTROL
- 2.5 UM ß-LAP
- 2.5 UM ß-LAP + 12 MM MEOX
- 4.0 UM ß-LAP

OLIGO : ETC COMPLEX I INHIBITOR

FCCP : ETC UNCOUPLER

ROTENONE : ETC COMPLEX IV INHIBITOR

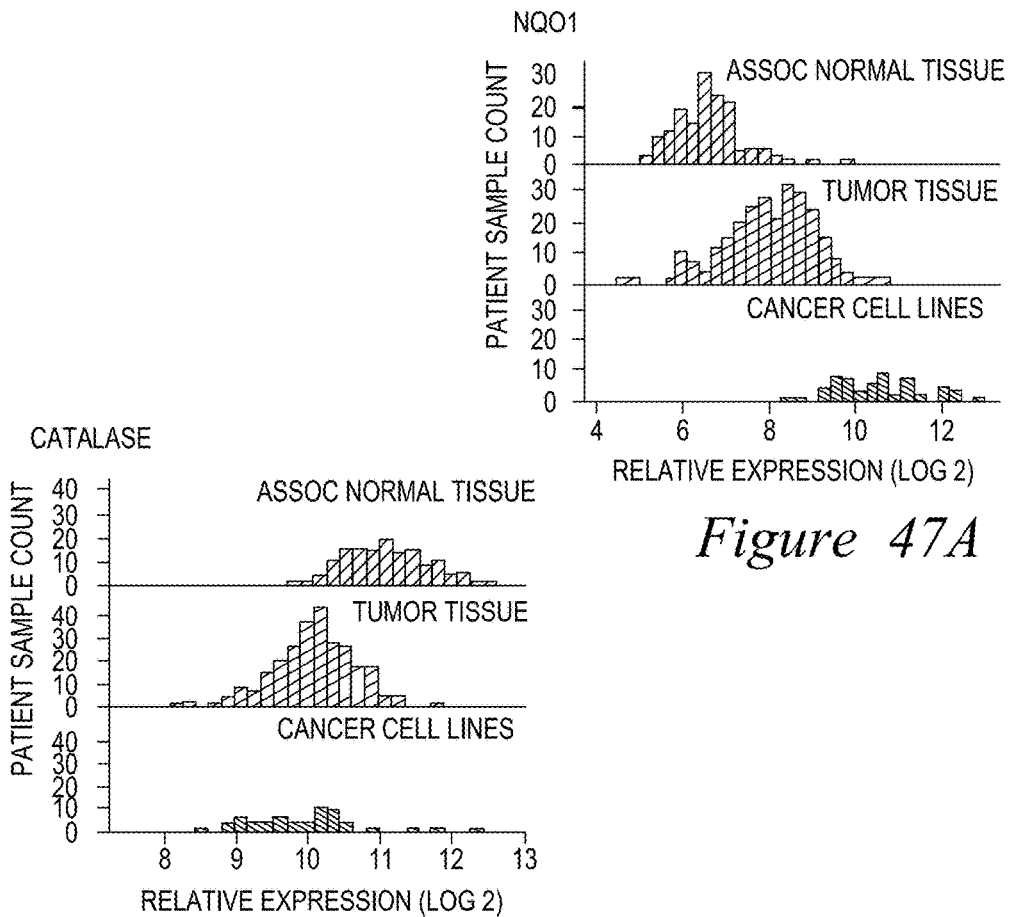
Figure 47A
Figure 47B
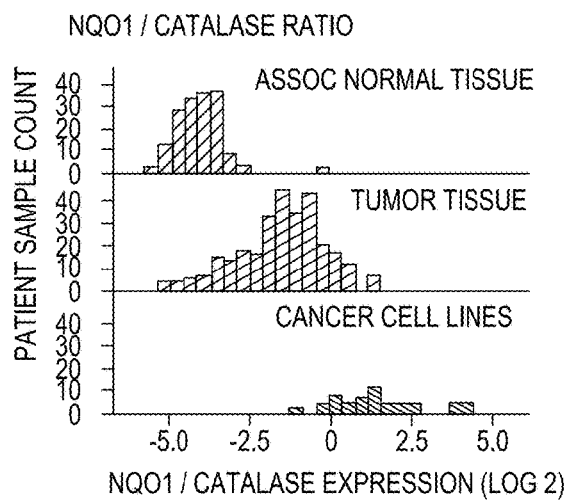
Figure 47C

TUMOR-SELECTIVE COMBINATION THERAPY

RELATED APPLICATIONS

This application is a national phase application under 35 U.S.C. § 371 of International Patent Application No. PCT/US2014/033400, filed Apr. 8, 2014, which claims priority under 35 U.S.C. § 119(e) to U.S. Provisional Patent Application No. 61/810,008, filed Apr. 9, 2013, each of which is incorporated herein by reference.

GOVERNMENT SUPPORT

This invention was made with government support under contract number CA102792 awarded by the National Institutes of Health. The government has certain rights in the invention.

BACKGROUND OF THE INVENTION

A fundamental challenge in cancer treatment is the discovery of compounds that are toxic to cancer cells but not healthy cells. A salient feature of cancer is rapid and unrestricted cell division. The vast majority of traditional chemotherapeutics target rapidly dividing cells by disrupting the cell cycle, causing cell death. Because some healthy tissues require cell division as part of their function, antiproliferative cytotoxins can also kill healthy cells, resulting in severe, dose-limiting side effects. Accordingly, new therapeutic methods and new cellular targets must be identified that better differentiate healthy and cancerous cells. The targets may be present in only a small fraction of cancer patients, thereby allowing for a personalized strategy to treat cancer.

Quinone-containing molecules are frequently cytotoxic and harm cells through one of two mechanisms. Many quinones are conjugate addition acceptors and readily alkylate nucleophilic species such as DNA and cysteine residues. Quinones are also substrates for 1-electron reductases, such as cytochrome P450s, cytochrome b5, xanthine oxidase, and glutathione reductase. Reduction of quinones by these enzymes generates a highly reactive semiquinone that can damage biomolecules directly, or can be oxidized by dissolved oxygen resulting in the formation of an equivalent of superoxide anion radical and the parent quinone. Thus, 1-electron reduction of quinones can catalytically create reactive oxygen species (ROS) that damage the cell.

NAD(P)H quinone oxidoreductase (NQO1, DT diaphorase) is an FAD-dependent 2-electron reductase whose primary function is to protect the cell from cytotoxins, especially quinones. Although generally identified as a cytosolic protein, NQO1 has been identified in subcellular compartments such as the mitochondria and nucleus. By reducing quinones in a 2-electron process, NQO1 bypasses the toxic semiquinone and forms hydroquinones, which are commonly unreactive toward oxygen. Hydroquinones are then conjugated with molecules such as glutathione, glucose, or sulfate, and excreted by the cell. However, some hydroquinone-containing molecules are unstable and react with oxygen in two 1-electron oxidations back to the quinone, generating ROS. The relative stability of hydroquinones toward air oxidation cannot be predicted based on molecular structure and it does not correlate with reduction potential.

NQO1 has attracted much attention as a potential target for the treatment of cancer because it has been shown to be frequently expressed at much higher levels in tumors relative to adjacent healthy tissue, particularly in the case of lung cancer. In addition, NQO1 activity appears to increase during tumor progression. Other than for lung, breast, and colon tissues, relatively little data on the levels of NQO1 in normal tissues have been reported. Whereas low levels of NQO1 are reported in bone marrow and liver cells—two tissues frequently damaged by chemotherapeutics—relatively high levels of NQO1 have been noted in stomach and kidney cells.

The prospect of discovering toxins that are activated, instead of deactivated, by NQO1 has attracted researchers for many years. Such molecules would turn this normally cytoprotective enzyme into a liability for the cell. Two general classes of molecules have been discovered that fit this description: DNA alkylators whose electrophilicity is increased after bioreduction, and redox cycling molecules that generate ROS catalytically after reduction. Examples of such DNA alkylators include Mitomycin C, EO9, and MeDZQ, and examples of such ROS generators include β-lapachone (β-lap) and streptonigrin, the cytotoxic mechanisms of which each involve NQO1-mediated bioreduction. These classes of molecules are composed almost exclusively of quinone-containing compounds.

The concentration of β-lap delivered to cells may induce different forms of cell death, with lower concentrations inducing apoptosis and higher concentrations initiating calcium-dependent necroptosis. In addition to ROS generation in RBCS, the poor aqueous solubility of β-lap necessitates the use of hydroxypropyl-β-cyclodextrin (HPβCD) as a solubility aid, high concentrations of which cause hemolysis of RBCS in vitro. To address the issues of compound instability and damage to RBCS, the Boothman and Gao groups have designed a micellar formulation of β-lap that demonstrates greatly improved PK properties and efficacy in murine tumor models (Blanco, Boothman, Gao et al., *Cancer Res.* 2010, 70, 3896).

While personalized medicine strategies have produced life-saving anticancer drugs, they affect only a small percentage of cancer patients. Because NQO1 levels are highly elevated in a large number of solid tumors, a treatment that successfully exploits NQO1 levels could benefit a significant fraction of all cancer patients. Thus, new therapeutic methods that exploit elevated NQO1 levels and that can selectively inhibit or kill cancer cells are needed to benefit larger numbers of cancer patients.

SUMMARY

The invention provides compounds, compositions and methods to treat cancer and cancer tumor cells, for example, tumor cells having elevated levels of NQO1. The invention also provides novel combination therapy including the administration of NQO1 bioactivatable drugs in combination with DNA repair inhibitors to provide a tumor-selective therapy. In one embodiment, inhibiting base excision repair synergistically enhances beta-lapachone-mediated cell death for tumor-selective therapy of cancers such as pancreatic cancer.

NQO1 bioactivatable drugs include DNQ analogs and prodrugs that are NQO1 substrates, and β-lapachone and its prodrugs or analogues. These drugs make DNA repair inhibitors tumor-selective. Such DNA repair inhibitors can include inhibitors of DNA base excision (BE), single strand break (SSB), and double strand break (DSB) repair.

1. NQO1 bioactivatable drugs can be used in a tumor-selective manner against cancers with defects in base excision repair (BER). Data indicate that BER processes are deficient (e.g., XRCC1) in specific cancers known to have elevated levels of NQO1 (i.e., breast cancers). For example, XRCC1 knockdown, whose levels have been shown to be selectively deficient in breast cancer, shows enhanced lethality in response to NQO1 bioactivatable drugs. XRCC1 knockdown and other BER deficiencies can result in increased DNA single strand breaks and AP sites. Prolonged AP site, SSBs or DNA double strand breaks (DSBs) caused in a tumor-selective manner by NQO1 bioactivatable drug treatment, results in tumor-specific lethality and synergy, with dramatic tumor-selective, NQO1-dependent metabolic changes. Defects in Ogg1 are an exception because its knockdown made cells resistant to NQO1 bioactivatable drugs. These data highlight that the initial DNA lesions are 8-oxoguanine base lesions, an unreported finding at the heart of inhibiting BER processes. The formation of dramatic levels of 8-oxoguanine (8-OG) in pancreatic cancer cells in an NQO1-dependent manner has also been shown.

2. NQO1 bioactivatable drugs can be used in a tumor-selective manner in combination with poly(ADP-ribosyl) polymerase I (PARP1) inhibitors, such as the PARP1 inhibitors described herein. PARP1 inhibitors lack tumor-selectivity and NQO1 bioactivatable drugs afford this selectivity. All current published data regarding NQO1 bioactivatable drugs assert that PARP1 hyperactivation is required for tumor-selective lethality; therefore inhibiting PARP1 would not be indicated. This is not the case in long-term survival responses, because inhibiting PARP1 prevents repair of SSBs and/or DSBs. Cells die by a different, classical apoptotic mechanism, versus by programmed necrosis caused by NQO1 bioactivatable drugs alone.

All known PARP1 inhibitors tested show synergy with NQO1 bioactivatable drugs in various cancers that overexpress NQO1. Cells die by activating caspases and do not undergo programmed necrosis. Nevertheless, tumor-selective lethality is observed in each case. Data obtained include that nontoxic doses of PARP1 inhibitors synergize with nontoxic doses of NQO1 bioactivatable drugs. Data with ß-lap and DNQ analogs strongly support this observation. Additionally, dicoumarol prevents the synergy between NQO1 bioactivatable drugs and PARP1 inhibitors, and the synergy is not noted in NQO1-deficient cells since these cells lack DNA damage caused by the lack of NQO1-mediated futile redox cycle.

3. AP-site modifying drugs (e.g., methoxyamine, MeOX) can be used in combination with NQO1 bioactivatable drugs for NQO1-dependent, tumor-selective lethality. NQO1 bioactivatable drugs cause predominantly DNA base damage (e.g., 8-oxyguanine (8-OG)), and loss of Ogg1 (a glycosylase that detects 8-oxoguanine) results in resistance to these drugs. When 8-oxoguanine is repaired, massive levels of AP sites are formed. While PARP1 can bind AP sites, it was not known that PARP1 could bind AP sites modified by methoxyamine or other AP-modifying drugs. We demonstrated that MeOX enhances NQO1 bioactivatable drugs, and vice versa that NQO1 bioactivatable drugs make MeOX tumor-selective. Data obtained include that nontoxic doses of MeOX enhance nontoxic doses of NQO1 bioactivatable drugs, and that MeOX enhances loss of ATP, and more importantly significantly prevents ATP recovery after toxic or nontoxic doses of NQO1 bioactivatable drugs.

For all three of the methods described above and herein below, much lower doses of NQO1 bioactivatable drugs can be used in all three versions of the combination therapies, avoiding dose-related toxicity (i.e., methemoglobinemia) with ß-lapachone, its prodrugs, and analogues, and especially DNQ analogues.

The invention further provides methods for predicting and determining the efficacy of NQO1 bioactivatable drugs and/or their combination with base excision repair (BER) enzyme inhibitors, PARP1 inhibitors, AP base modifying drugs, or a combination thereof. The methods can include analyzing and monitoring NQO1:catalase ratios in cells or in a subject to determine if the cells or patient, or tissues of the subject, have a relatively high, medium, or low NQO1:catalase ratio, thereby allowing for a determination of the likely efficacy of the actives or combination of actives.

Another aspect of the invention provides pharmaceutical compositions that contain at least one ß-lapachone or derivative thereof, or a DNQ compound, for example, a compound of Formula (I) and a pharmaceutically acceptable diluent, carrier, or excipient, optionally in combination with a base excision repair (BER) enzyme inhibitor, a PARP1 inhibitor, or an AP base modifying drug (e.g., MeOX). The invention also provides for the use of these compounds and combinations thereof for the preparation of pharmaceutical compositions, and the subsequent use of the compositions in the treatment of patients or subjects. Patients or subjects can be mammals, including humans.

A further aspect of the invention provides methods of treating, killing, or inhibiting the growth of tumor cells that have elevated NQO1 levels or a tumor having cells that have elevated NQO1 levels, where at least one tumor cell is exposed to a therapeutically effective amount of a compound, a pharmaceutically acceptable salt or solvate thereof, a combination of compounds, or a pharmaceutically acceptable composition thereof. The administration of the compounds to cells, or to a patient in need of therapy (including vulnerable tumors known to be deficient in DNA base excision, single strand, or DNA double strand break repair), can be concurrent or sequential, with a quinone compound administered at least concurrently or after a base excision repair (BER) enzyme inhibitor, a PARP1 inhibitor, or an AP base modifying drug.

Thus, the invention provides the use of a NQO1 bioactivatable drug in combination with a base excision repair (BER) enzyme inhibitor or other active agent described herein for killing or inhibiting the growth of cancer cells in vitro, or cancer cells in a patient that has cancerous cells or a cancer tumor. The invention further provides the use of a NQO1 bioactivatable drug in combination with a base excision repair (BER) enzyme inhibitor or other active agent described herein for the manufacture of a medicament for killing or inhibiting the growth of cancer cells in vitro, or cancer cells in a patient that has cancerous cells or a cancer tumor, wherein the medicament comprises an effective lethal or inhibitory amount of the NQO1 bioactivatable drug and the base excision repair (BER) enzyme inhibitor or other active agent described herein. In other embodiments, one medicament can include a NQO1 bioactivatable drug and a second medicament can include a base excision repair (BER) enzyme inhibitor or other active agent described herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1B:
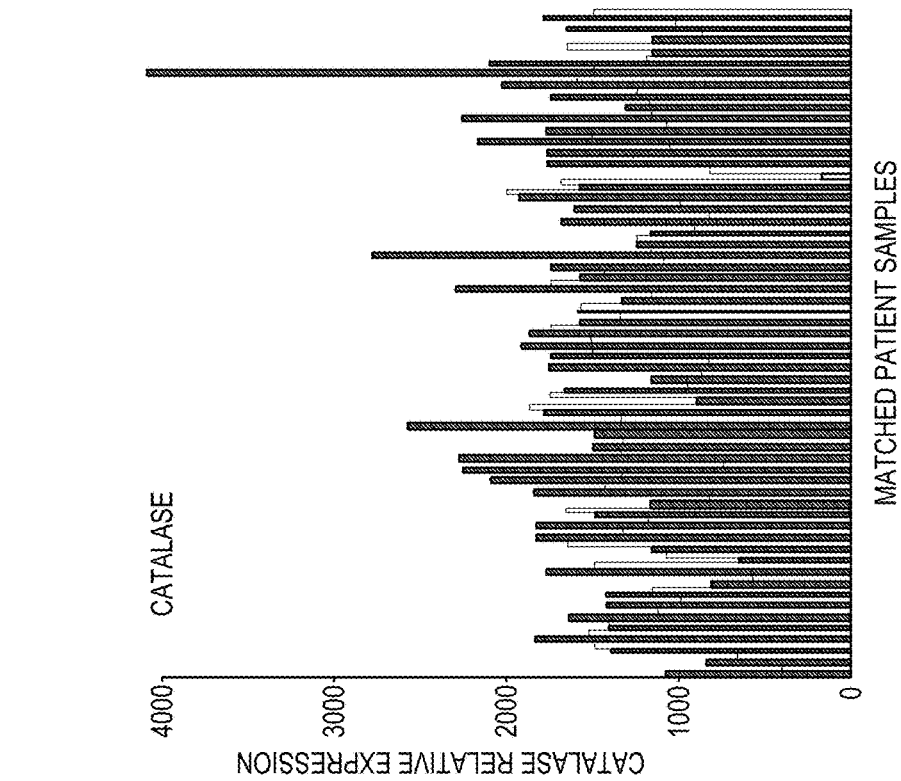
FIG. 1. Expression of NQO1 and Catalase in pancreatic tumor vs. associated normal tissue. (A,B) Matched tumor and associated normal tissue from 59 pancreatic patients were analyzed for NQO1 (A) and Catalase (B) levels, showing significant Catalase over-expression in normal vs. tumor tissue. (C,F) NQO1 levels from 349 patient samples and 85 pancreatic cancer cell lines. (D,G) Catalase levels monitored as in (C,F). (E,H) NQO1/catalase ratios can be a major determinant in the efficacy of NQO1-bioactivatable drugs. For (C—H), n=232 patient samples.
Figure 1A:
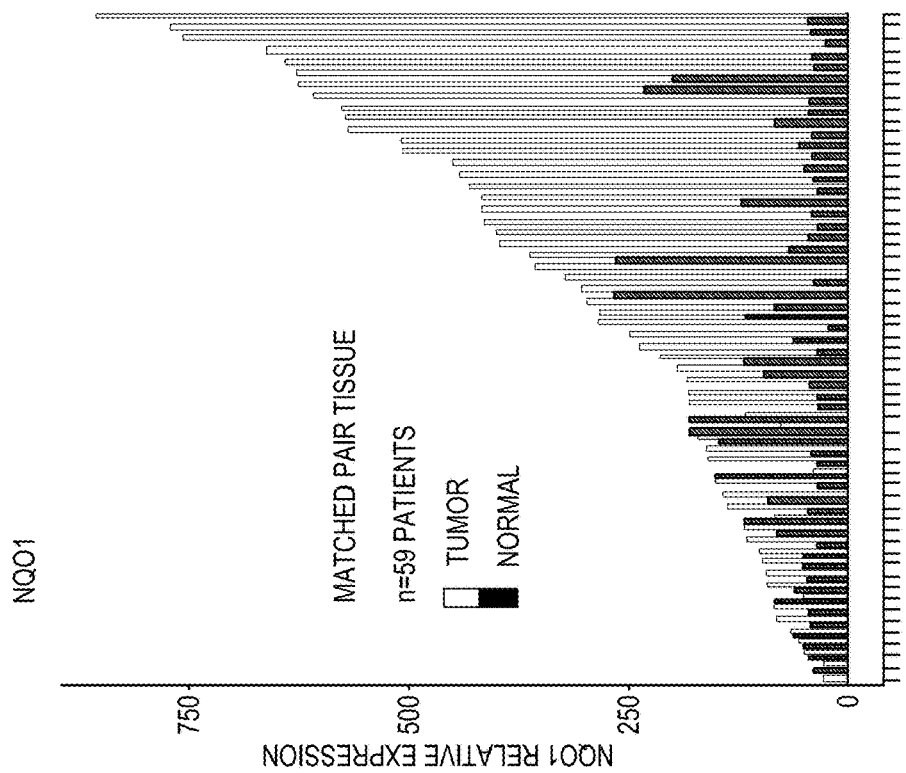
Figures 1C, 1D, 1E:
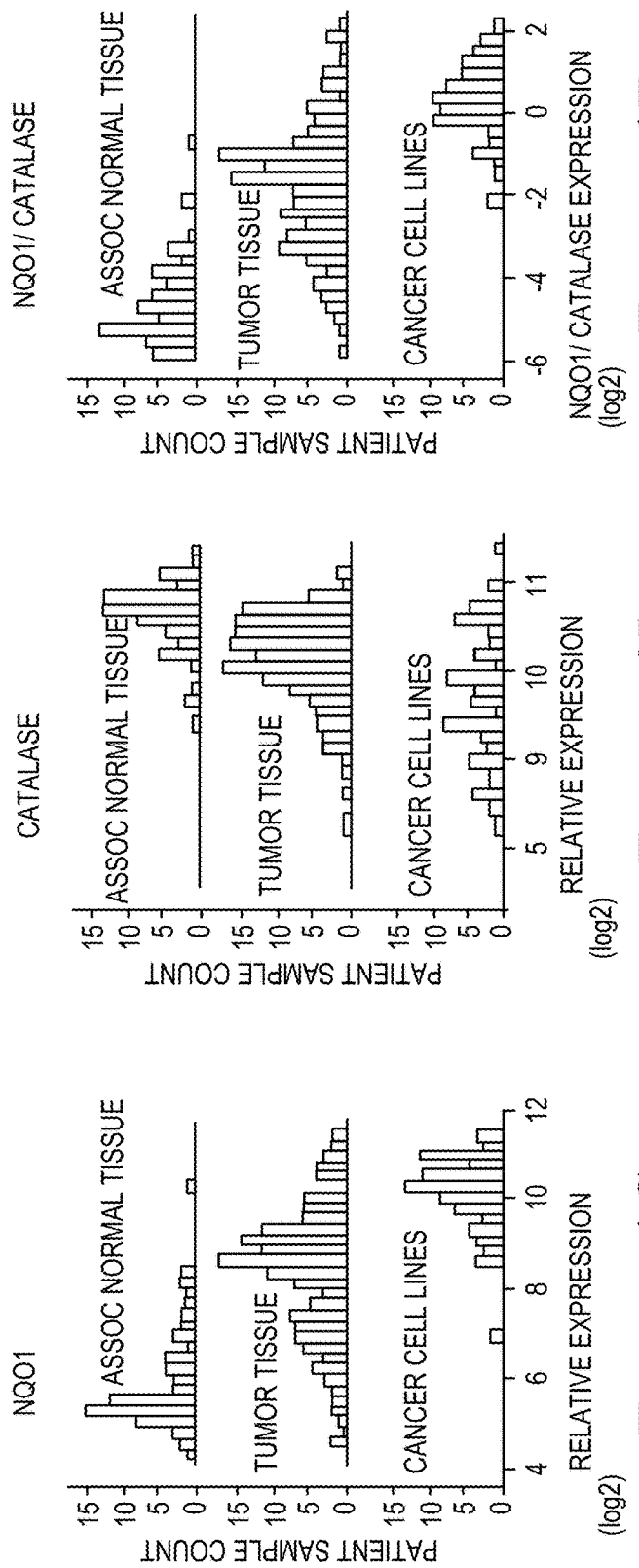
Figures 1F, 1G, 1H:
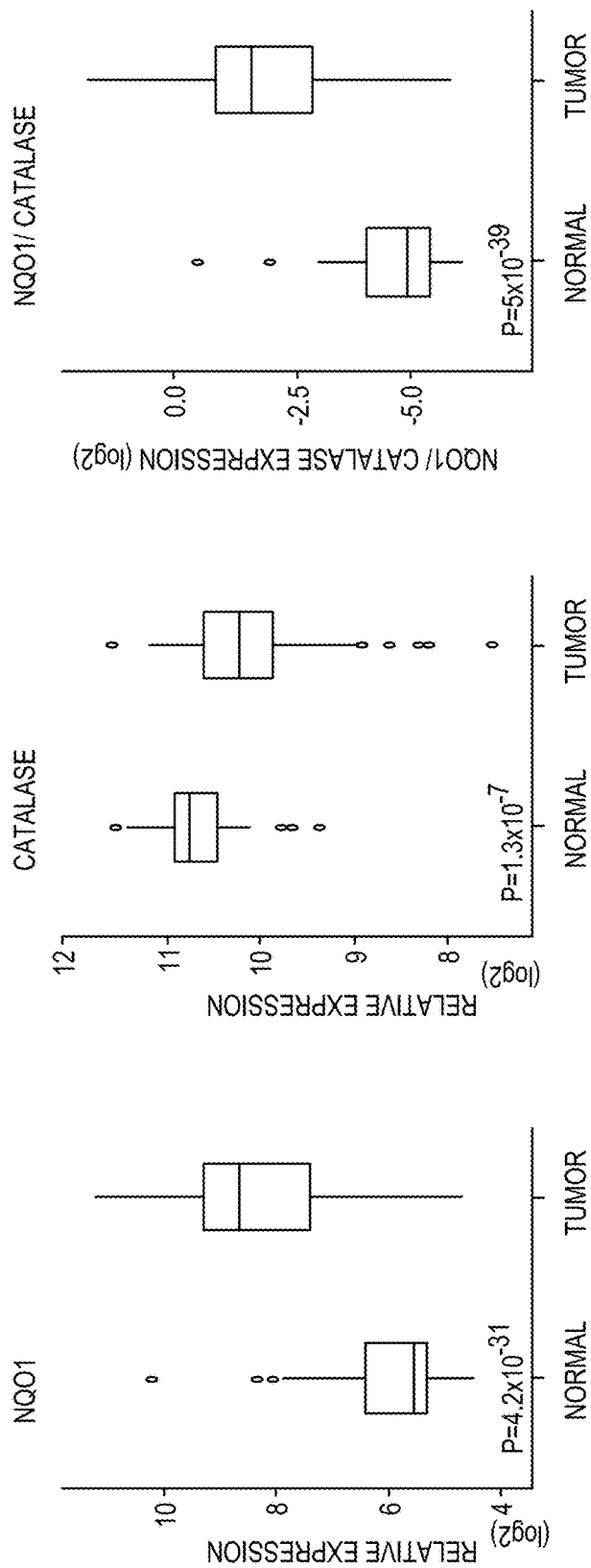

Tumor-selectivity remains a challenge for efficacious chemotherapeutic strategies against cancer. Although the recent development of β-lapachone to specifically exploit elevated levels of NAD(P)H:quinone oxidoreductase 1 (NQO1) in most solid tumors represents a novel chemotherapeutic approach, additional therapies that kill by various mechanisms such as programmed necrosis at increased potency are needed. Deoxynyboquinone (DNQ) kills a wide spectrum of cancer cell types (i.e., breast, non-small-cell lung, prostate, pancreatic) in an NQO1-dependent manner with greatly improved (20- to 100-fold) potency compared to β-lapachone. DNQ lethality relies on NQO1-dependent futile redox cycling, using oxygen and generating extensive reactive oxygen species (ROS), particularly superoxide and hydrogen peroxide. Elevated ROS levels cause extensive DNA lesions and PARP-1 hyperactivation that, in turn, results in severe NAD$^+$/ATP depletion that stimulates calcium-dependent programmed necrotic cell death responses unique to this class of NQO1 'bioactivated' drugs (e.g., β-lapachone and DNQ). It was surprisingly discovered that the combination of NQO1 bioactivatable drugs and DNA repair inhibitors provide a synergistic and tumor-selective therapy.

Pancreatic cancer will be the second leading cause of cancer-related deaths in the U.S. by 2020, where 5-year survival is <6%. Current standard of care therapies offer little selectivity and high toxicity. Novel, tumor-selective approaches are therefore desperately needed. Nearly 90% of pancreatic cancers have elevated levels (10- to 40-fold) NQO1 and we recently showed that beta-lapachone (beta-lap) was efficacious against pancreatic cancers in an NQO1-dependent manner (Li et al., Clin. Cancer Res., 2011). Beta-Lap is reduced by NQO1 like most quinones, but unlike most, its hydroquinone form is unstable and spontaneously redox cycles in a futile manner where one mole of beta-lap generates ~120 moles of superoxide in two minutes, inducing predominately DNA base and single strand break (SSB) damage.

This results in PARP1 hyperactivation and programmed necrosis, killing NQO1+ cancer cells independent of: i, p53; ii, cell cycle; iii, all known oncogenic drivers; and iv, apoptotic/antiapoptotic gene expression (e.g., Bax, Bak, Bcl2). Thus, 'NQO1 bioactivatable drugs' are tumor-selective and excellent candidates for improving efficacy of cancer therapies including therapy for pancreatic cancer and other solid tumor cancers.

To improve its efficacy, the synergistic effects of adding the AP site-modifying drug and base excision repair (BER) inhibitor, methoxyamine (MeOX), with beta-lap against NQO1 over-expressing pancreatic cancer cells were examined. MeOX+beta-lap synergy resulted in enhanced lethality of sub-lethal doses of beta-lap; increased DNA lesion formation only in tumor cells; dramatic losses in ATP levels; and dramatic suppression of glycolysis. MeOX therefore enhances PARP1 hyperactivation and synergistic cell killing by beta-lap. Mechanistically, the data indicate that PARP1 detects MeOX-AP modified sites or SSBs, allowing PARP1 hyperactivation and synergistic cell death. Because MeOX is a nontoxic agent, the combination of MeOX and a second agent can provide therapies for the treatment of cancers, particularly pancreatic cancer, as well as other NQO1 over-expressing solid cancers.

Therapeutic Quinones

DNQ is a potent chemotherapeutic agent exhibiting a wide therapeutic window that holds great promise for targeted therapy against a wide spectrum of difficult to treat cancers, including pancreatic and non-small cell lung cancer. Despite considerable advances in cancer chemotherapy, the lack of selectivity of most cancer chemotherapeutics remains a major limiting factor. Elevated NAD(P)H:quinone oxidoreductase-1 (NQO1, DT-diaphorase, EC 1.6.99.2) levels found in most solid tumors, particularly in non-small-cell lung cancer cells (NSCLC), prostate, pancreatic and breast, provide a target for therapeutic treatments described herein. NQO1 is an inducible Phase II detoxifying two-electron oxidoreductase capable of reducing most quinones, forming stable hydroquinones. In most cases, glutathione transferase then detoxifies hydroquinones, conjugating them with glutathione for secretion, and effectively avoiding more toxic semiquinones.

For some rare compounds, however, NQO1-mediated bioreduction can be exploited for antitumor activity. Rather than promoting detoxification, NQO1 activity can convert specific quinones into highly cytotoxic species. Most antitumor quinones dependent on NQO1 are DNA alkylators: (a) mitomycin C (MMC); (b) RH1; (c) E09; and (d) AZQ. However, these DNA alkylators are not only subject to detoxification pathways, but resistance from elevated or inducible DNA repair pathways limit their usefulness. Furthermore, many of these drugs are efficient substrates for one-electron oxidoreductases ubiquitously expressed in normal tissues.

The ortho-naphthoquinone, β-lapachone (β-lap, Scheme 1), kills cultured cancer cells and murine xenograft and orthotopic human or mouse tumor models in vivo in an NQO1-dependent manner. In contrast to alkylating quinones, β-lap induces cell death by NQO1-dependent reactive oxygen species (ROS) formation and oxidative stress. NQO1 metabolism of β-lap results into an unstable hydroquinone that is spontaneously oxidized by two equivalents of dioxygen, generating superoxide.

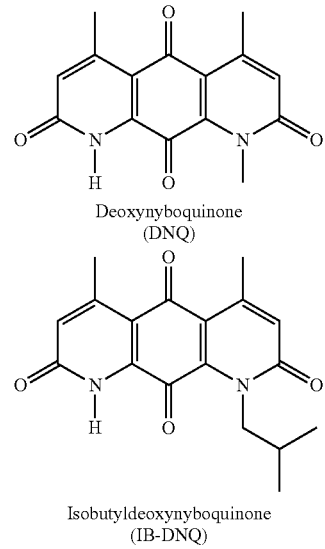

Scheme 1. Examples of Quinone Compounds.

Deoxynyboquinone (DNQ)

Isobutyldeoxynyboquinone (IB-DNQ)

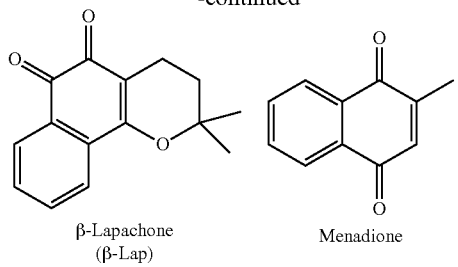

β-Lapachone (β-Lap)    Menadione

A futile cycle of oxidoreduction is thus established, and elevated superoxide levels, in turn cause massive DNA base and single strand break (SSBs) lesions that normally are easily and rapidly repaired. However, extensive DNA lesions created in β-lap-treated NQO1 over-expressing cancer cells results in hyperactivation of poly(ADP-ribose) polymerase-1 (PARP1), an otherwise essential base and SSB repair enzyme. In turn, PARP1 hyperactivation results in dramatic reduction of the $NAD^+$/ATP pool due to ADP-ribosylation, causing tremendous energy depletion and cell death. As a result, β-lap kills NQO1+ cancer cells by a unique programmed necrosis mechanism that is: (a) independent of caspase activation or p53 status; (b) independent of bcl-2 levels; (c) not affected by BAX/BAK deficiencies; (d) independent of EGFR, Ras or other constitutive signal transduction activation; and/or (e) not dependent on proliferation, since NQO1 is expressed in all cell cycle phases. Thus, β-lap is an attractive experimental chemotherapeutic, and various β-lap formulations have been, or are in, phase I/II clinical trials.

Deoxynyboquinone (DNQ, Scheme 1) is a promising anti-neoplastic agent. Prior data indicated that DNQ kills cancer cells through oxidative stress and ROS formation. The cytotoxicity of DNQ was partially prevented by N-acetylcysteine, a global free radical scavenger and precursor to glutathione. It has now been show that DNQ undergoes an NQO1-dependent futile cycle similar to β-lap, where oxygen is consumed, and ROS is formed and extensive DNA damage triggers PARP1 hyperactivation, with dramatic decreases in essential $NAD^+$/ATP nucleotide pools, indicative of programmed necrosis. Importantly, DNQ is 20- to 100-fold more potent than β-lap, with a significantly enhanced therapeutic window in NQO1+ versus NQO1− NSCLC cells. Efficacious NQO1-dependent killing by DNQ is also shown in breast, prostate, and pancreatic cancer models in vitro. Furthermore, in vitro NQO1 processes DNQ much more efficiently than β-lap, indicating that increased utilization accounts for its increased potency. Thus, DNQ offers significant promise as a selective chemotherapeutic agent for the treatment of solid tumors with elevated NQO1 levels, however, the combination therapy described herein can provide efficacious therapies with a variety of quinone compounds due to the synergy of the combination.

Because NQO1 is overexpressed in the majority of solid tumors, and the cytotoxicity of the various quinone compounds depends predominately on the elevated expression of the enzyme NQO1, thus the quinine compounds and their derivatives can be excellent means to approach targeting solid tumors. The invention provides numerous new cytotoxic compounds that can be used as new cancer therapeutics, as described herein.

The foregoing and other objects and features of the disclosure will become more apparent from the following detailed description, which proceeds with reference to the accompanying figures. Further embodiments, forms, features, aspects, benefits, objects, and advantages of the present application shall become apparent from the detailed description and figures provided herewith.

Use of NQO1 Bioactivatable Drugs for Tumor-Specific Use with DNA Repair Inhibitors NQO1 bioactivatable drugs (all β-lapachone and DNQ derivatives that are substrates for NQO1) generate tremendous levels of reactive oxygen species in an NQO1-dependent, tumor-selective manner, allowing the use of DNA repair inhibitors, including all PARP1 inhibitors, DNA double strand break repair inhibitors, as well as base excision repair inhibitors, to be used in a tumor-specific manner, effecting a tumor-selective efficacy of both agents. DNA repair inhibitors, in general, have failed because of the lack of tumor selectivity. Because these NQO1 bioactivatable drugs cause tumor selective production of DNA lesions, including DNA base damage, single strand breaks and double strand breaks, DNA repair inhibitors can be used to provide tumor selective antitumor activity. Tumor-selective activity and responses include dramatic inhibition of glycolysis as well as other tumor-selective metabolism inhibition.

NQO1 bioactivatable drugs can be used to make DNA repair inhibitors tumor-selective in a manner that is not obvious unless one knows the DNA lesions generated, and in a manner that causes metabolic changes and cell death responses that are not obvious and are altered depending on the DNA repair inhibitors used. For example, PARP1 inhibitors administered with DNQ bioactivatable drugs cause standard apoptotic responses without energy losses. In contrast, DNA double strand break repair, single strand break repair, and base excision repair inhibitors enhance PARP1 hyperactivation, with subsequent losses in energy metabolism and programmed necrosis.

The only current use of DNA repair inhibitors, such as PARP-1 inhibitors, is through the unique exploitation of tumor-specific synthetic lethality responses (e.g., use of PARP1 inhibitors in BRACA1/2 mutant tumors). This, however, is a very limited use of DNA repair inhibitors—approximately only 5% of breast cancers only. In contrast, the approach described herein can treat all cancers having elevated NQO1 and lowered Catalase levels, while normal tissue have elevated Catalase and low levels of NQO1. The methods described herein provide a new use of DNA repair inhibitors, allowing for their use in a tumor-selective manner, while also potentiating NQO1 bioactivatable drugs. Both agents can be used at nontoxic doses to render synergistic, tumor-selective efficacy responses.

To date, DNA repair inhibitors fail in the lack of tumor-selective responses and efficacy. The methods described herein resolve these limitations, while greatly potentiating NQO1 bioactivatable drugs. The methods also allow the use of 2- to >4-fold lower doses of NQO1 bioactivatable drugs, resolving toxic effects of these NQO1 bioactivatable drugs (e.g., methemaglobinemia). In the therapeutic methods, the inhibitors can be added before and after NQO1 bioactivatable drugs, at a minimum before, and optionally before, simultaneously, after, or a combination thereof. Cell death responses depend on inhibitor used. The responses are not obvious and would entail specific biomarkers to follow in vivo.

Definitions

In general, the terms and phrases used herein have their art-recognized meaning, which can be found by reference to standard texts, journal references and contexts known to those skilled in the art. Such art-recognized meanings may be obtained by reference to technical dictionaries, such as *Hawley's Condensed Chemical Dictionary* 14$^{th}$ Edition, by R. J. Lewis, John Wiley & Sons, New York, N.Y., 2001.

BER, base excision repair; SSBR, single strand break repair; DSBR, double strand break repair.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments and any further applications of the principles of the invention as described herein are contemplated as would normally occur to one skilled in the art to which the invention relates.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

A "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

A "therapeutically effective amount" of a compound with respect to the subject method of treatment refers to an amount of the compound(s) in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. The term "treating" or "treatment" can include reversing, reducing, or arresting the symptoms, clinical signs, and underlying pathology of a condition in manner to improve or stabilize a subject's condition.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "exposing" is intended to encompass definitions as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a chemotherapeutic agent.

The term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

The term "tumor" refers to a neoplasm, typically a mass that includes a plurality of aggregated malignant cells.

The following groups can be R groups or bridging groups, as appropriate, in the formulas described herein.

The term "alkyl" refers to a monoradical branched or unbranched saturated hydrocarbon chain preferably having from 1 to 30 carbon atoms. Short alkyl groups are those having 1 to 12 carbon atoms including methyl, ethyl, propyl, butyl, pentyl, and hexyl groups, including all isomers thereof. Long alkyl groups are those having 12-30 carbon atoms. The group may be a terminal group or a bridging group.

Alkyl, heteroalkyl, aryl, heteroaryl, and heterocycle groups, and cyclic and/or unsaturated versions thereof, can be R groups of Formula I, and each group can be optionally substituted.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O$^-$)$_{12}$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on a substituted group.

The term "heteroalkyl," by itself or in combination with another term, means, unless otherwise stated, a stable straight or branched chain, or cyclic hydrocarbon radical, or combinations thereof, often having from 2 to 14 carbons, or 2 to 10 carbons in the chain, including at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. The heteroalkyl group can have, for example, one to about 20 carbon atoms in a chain. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$CH=N—OCH$_3$, —CH=CH—N(CH$_3$)—CH$_3$, O—CH$_3$, —O—CH$_2$—CH$_3$, and —CN. Additional examples of heteroalkyl groups include alkyl ethers, secondary and tertiary alkyl amines, amides, alkyl sulfides, and the like. The group may be a terminal group or a bridging group. As used herein, reference to a chain when used in the context of a bridging group refers to the direct chain of atoms linking the two terminal positions of the bridging group.

The term "alcohol" as used herein may be defined as an alcohol that comprises a $C_{1-12}$ alkyl moiety substituted at a hydrogen atom with one hydroxyl group. Alcohols include ethanol, n-propanol, i-propanol, n-butanol, i-butanol, s-butanol, t-butanol, n-pentanol, i-pentanol, n-hexanol, cyclohexanol, n-heptanol, n-octanol, n-nonanol, n-decanol, and the like. The carbon atoms in alcohols can be straight, branched or cyclic.

"Acyl" may be defined as an alkyl-CO— group in which the alkyl group is as described herein. Examples of acyl include acetyl and benzoyl. The alkyl group can be a $C_1$-$C_6$ alkyl group. The group may be a terminal group or a bridging (i.e., divalent) group.

"Alkoxy" refers to an —O-alkyl group in which alkyl is defined herein. Preferably the alkoxy is a $C_1$-$C_6$alkoxy. Examples include, but are not limited to, methoxy and ethoxy. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkynyl" as a group or part of a group may be defined as an aliphatic hydrocarbon group containing a carbon-carbon triple bond, the chain of which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl. The group may be a terminal group or a bridging group.

"Alkylsulfinyl" may be defined as a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Amino" refers to —NH$_2$, and "alkylamino" refers to —NR$_2$, wherein at least one R is alkyl and the second R is alkyl or hydrogen. The term "acylamino" refers to RC(=O)NH—, wherein R is alkyl or aryl. The alkyl group can be, for example, a $C_1$-$C_6$ alkyl group. Examples include, but are not limited to methylamino and ethylamino. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle of 3 to about 30 carbon atoms, often containing 3 to about 9 carbons per ring, such as cyclopropyl, cyclobutyl, cyclopentyl, cyclohexyl, cyclooctyl, and the like. It includes monocyclic systems such as cyclopropyl and cyclohexyl, bicyclic systems such as decalin, and polycyclic systems such as adamantane. The group may be a terminal group or a bridging group.

"Cycloalkenyl" may be defined as a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

Alkyl and cycloalkyl groups can be substituents on the alkyl portions of other groups, such as without limitation, alkoxy, alkyl amines, alkyl ketones, arylalkyl, heteroarylalkyl, alkylsulfonyl and alkyl ester substituents and the like. The group may be a terminal group or a bridging group.

"Cycloalkylalkyl" may be defined as a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, and (2-tetrahydrothiofuranyl)methyl. The group may be a terminal group or a bridging group.

"Halo" refers to a halogen substituent such as fluoro, chloro, bromo, or iodo.

The term "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 18 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, as described above in the definition of "substituted". Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (═O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The abbreviation "$DNQ_d$" as used herein refers to an analog or derivative of DNQ.

Additional groups that can be bridging groups or terminal groups of $R_1$, $R_2$, $R_3$, and $R_4$ are described below.

The term "carbonate ester" may be defined as a functional group having a general structure R'OC(═O)OR, where R' can be the tricyclic core of Formula I and R can be as defined in the definitions of the variables of Formula I.

The term "ester" may be defined as a functional group having a general structure RC(═O)OR', where R' can be the tricyclic core of Formula I and R can be as defined in the definitions of the variables of Formula I, or vice versa.

A "pyridyl" group can be a 2-pyridyl, 3-pyridyl, or 4-pyridyl group.

The term "sulfhydryl" may be defined as a functional group having a general structure —S—H.

The term "sulfinyl" may be defined as a functional group having a general structure R—S(═O)—R', where R' can be the tricyclic core of Formula I and R can be as defined in the definitions of the variables of Formula I, or vice versa.

The term "sulfonyl" may be defined as a functional group having a general structure R—S(═O)$_2$—R', where R' can be the tricyclic core of Formula I and R can be as defined in the definitions of the variables of Formula I, or vice versa.

The term "hexose" may be defined as a monosaccharide having six carbon atoms having the general chemical formula $C_6H_{12}O_6$ and can include aldohexoses which have an aldehyde functional group at position 1 or ketohexoses which have a ketone functional group at position 2. Example aldohexoses include, allose, altrose, glucose, mannose, gulose, idose, galactose, and talose, in either D or L form.

PARP inhibitors are a group of pharmacological inhibitors of the enzyme poly ADP ribose polymerase (PARP). They are developed for multiple indications including the treatment of cancer. Several forms of cancer are more dependent on PARP than regular cells, making PARP an attractive target for cancer therapy. PARP-1 inhibitors are particularly useful in the combination therapies described herein. PARP-1 inhibitors can be purchased from commercial vendors such as Selleck Chemicals. Examples of PARP-1 inhibitors include the inhibitors listed in Table 1 below.

TABLE 1

PARP-1 Inhibitors.

| | PARP1 Inhibitor: | | | | | |
|---|---|---|---|---|---|---|
| | AG-014699 (Rucaparib) | AG14361 | ABT-888 (Veliparib) | *BSI-201 (Iniparib) | AZD2281 (Olaparib) | INO-1001 |
| Formulation: | Normal saline | 1% DMSO | 0.9% NaCl adj. to pH 4.0 | HPBCD | HPBCD | water |
| **Sensitivity Enhancement (change in survival) | | | | | | |
| β-Lapachone | 10 | 5 | 10 | 3 | 10 | 7 |
| Deoxynyboquinone (DNQ) | 100 | 10 | 15 | 4 | 20 | 10 |

*Although BSI-201 was a reported PARP1 inhibitor and did synergize with β-lap or DNQ, using PARP1 knockdown cells we noted additional synergy, which was not observed with the other PARP1 inhibitors. Furthermore, its addition did not prevent PARP1 PAR formation as did all for the other inhibitors. We conclude, therefore that BSI-201 is not a PARP1 inhibitor, but rather a DNA damaging agent and this explains the synergy noted.
**Varying doses (μM) of each of the PARP1 inhibitors were added with varying doses of β-lapachone or DNQ. Reported sensitivity values represent changes in survival of A549 NSCLC cells or MiaPaCa-2 pancreatic cancer cells at nontoxic doses of either β-lapachone (3 μM for A549, 2 μM Mia Paca2 cells) or DNQ (0.02 μM for A549 cells, 0.025 μM for MiaPaca-2 cells) in combination with an optimal dose (i.e., 15 μM) of each PARP1 inhibitor. A value of 10 equals one log kill, and a value of 100 equals two logs kill and so on. PARP1 inhibitors were nonlethal to as high as 100 μM.

Compounds and Methods of the Invention

The invention provides DNQ compounds, beta-lapachone and derivatives thereof, and the use of NQO1 bioactivatable drugs in combination therapy for the treatment of cancer. Examples of DNQ compounds include compounds of Formula (I):

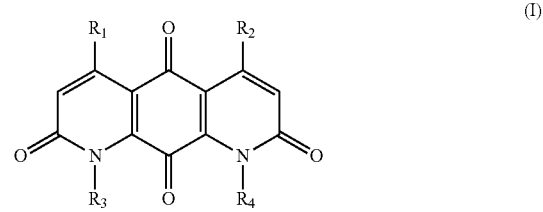

wherein $R_1$, $R_2$, $R_3$, and $R_4$ are each independently —H or —X—R;

each X is independently a direct bond or a bridging group, wherein the bridging group is —O—, —S—, —NH—, —C(=O)—, —O—C(=O)—, —C(=O)—O—, —O—C(=O)—O—, or a linker of the formula —W-A-W—, wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-10, or a direct bond, wherein each R' is independently H, (C$_1$-C$_6$)alkyl, or a nitrogen protecting group; and each A is independently (C$_1$-C$_{20}$)alkyl, (C$_2$-C$_{18}$)alkenyl, (C$_2$-C$_{18}$)alkynyl, (C$_3$-C$_8$)cycloalkyl, (C$_8$-C$_{10}$)aryl, —(OCH$_2$—CH$_2$)$_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a cycloalkyl, heterocycle, or aryl group;

each R is independently alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^y$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;

wherein any alkyl or aryl can be optionally substituted with one or more hydroxy, amino, cyano, nitro, or halo groups;

or a salt or solvate thereof.

In some embodiments, when R$_1$, R$_2$, and R$_3$ are methyl, R$_4$ is not H or methyl. In other embodiments, when R$_1$, R$_3$, and R$_4$ are methyl, the group —X—R of R$_2$ is not —CH$_2$—OAc. In certain embodiments, when R$_1$, R$_3$, and R$_4$ are methyl, the R group of R$_2$ is not acyloxy. In various embodiments, R$_1$-R$_4$ are not each H. In certain embodiments, R$_1$-R$_4$ are not each alkyl, such as unsubstituted alkyl. In some embodiments, R$_1$-R$^4$ are not each methyl.

In one embodiment, R$_1$, R$_2$, R$_3$, and R$_4$ are each (C$_{1-20}$) alkyl groups. In some embodiments, the (C$_{1-20}$)alkyl group is a (C$_{2-20}$)alkyl group, a (C$_{3-20}$)alkyl group, a (C$_{4-20}$)alkyl group, a (C$_{5-20}$)alkyl group, or a (C$_{10-20}$)alkyl group. The alkyl groups can be substituted, for example, with a hydroxyl or phosphate group. The phosphate group can be a phosphonic acid or a phosphonic acid salt, such as a lithium salt, a sodium salt, a potassium salt, or other known salt of phosphonic acids.

A specific value for R$_1$ is H. A specific value for R$_2$ is H. A specific value for R$_3$ is H. A specific value for R$_4$ is H.

A specific value for R$_1$ is methyl. A specific value for R$_2$ is methyl. A specific value for R$_3$ is methyl. A specific value for R$_4$ is methyl. The methyl can be substituted as described above for the term "substituted".

Figure 11:
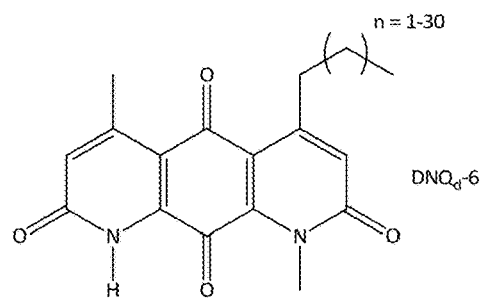
FIG. 11. Formulas of certain DNQ compounds, according to various embodiments of the invention. When n=1-30, n can be specifically any integer from 1 to 30, preferably 1, 2, 3, 4, 5, 6, 7, 8, 9, or 10.
Figure 11:
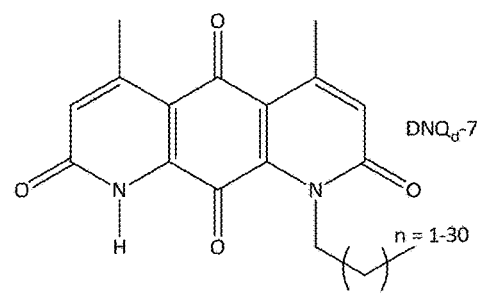
Figure 11:
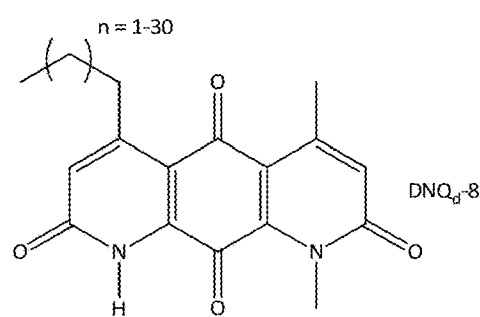
Figure 11:
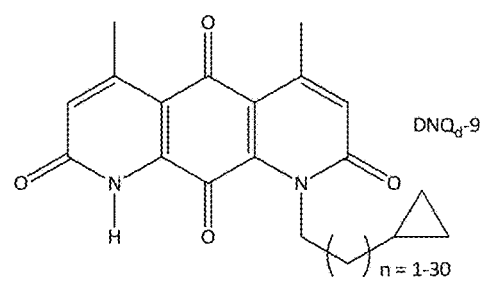
Figure 11:
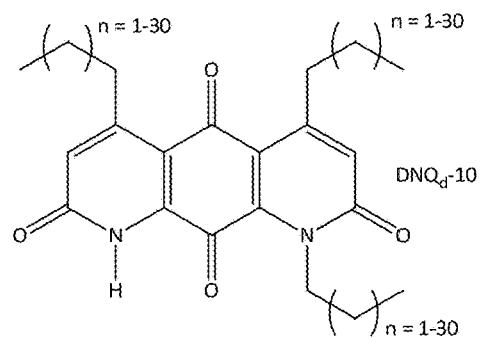
Figure 11:
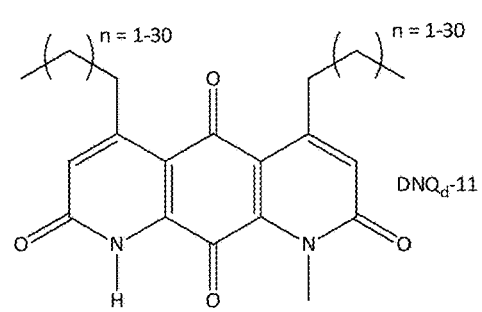
Figure 11:
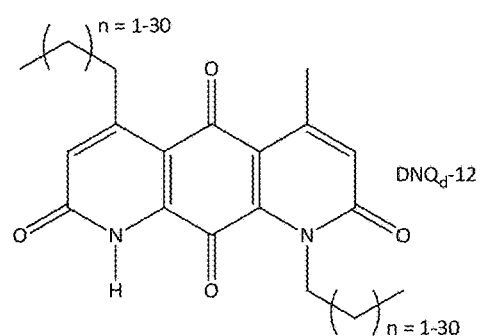
Figure 11:
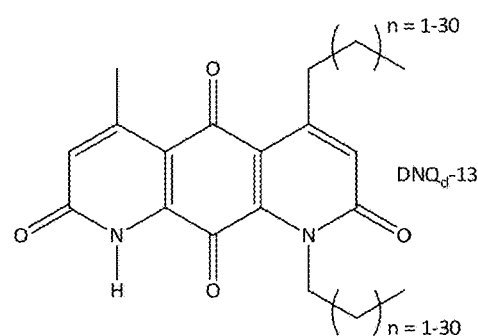
Figure 11:
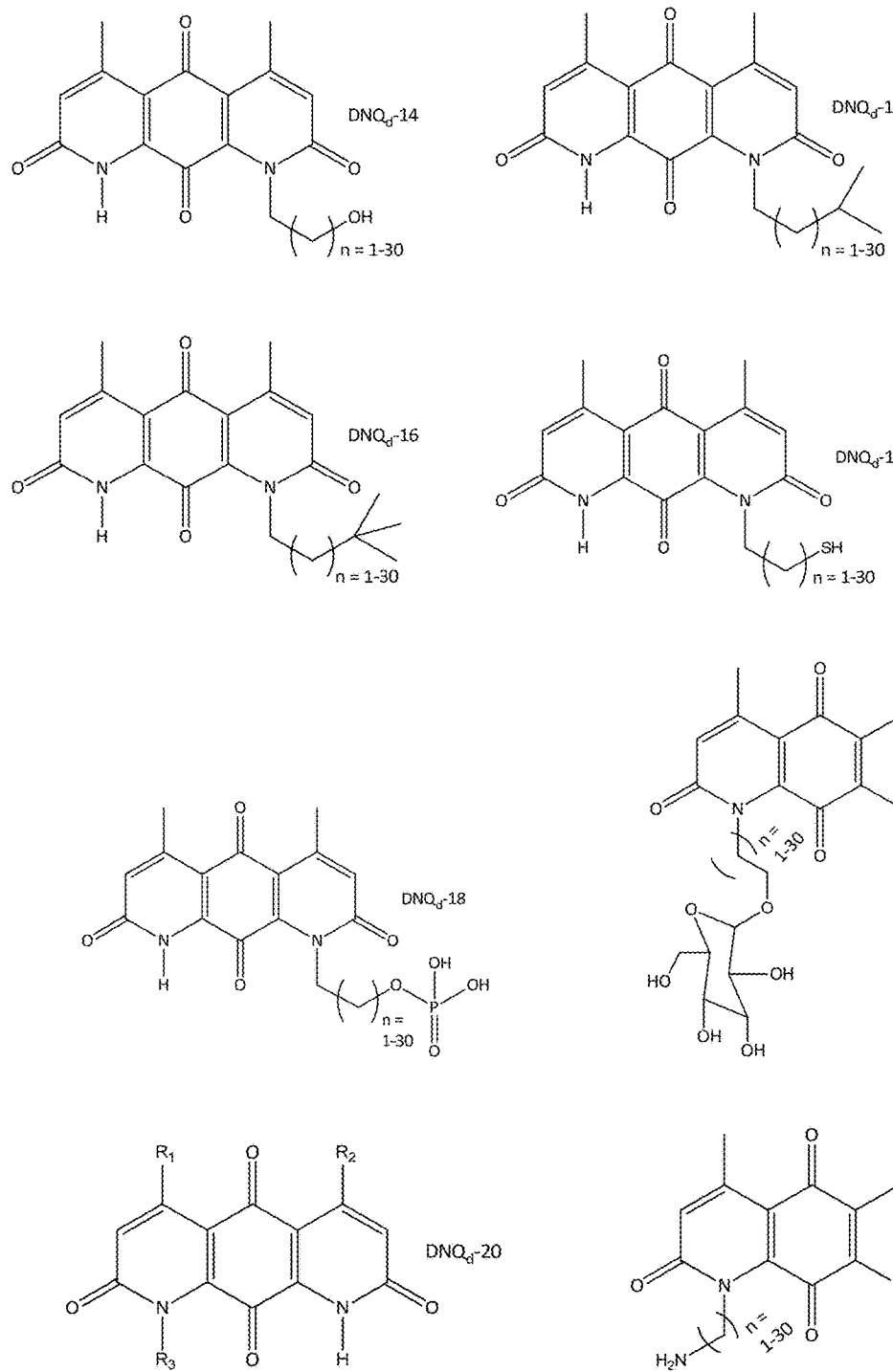
Figure 11:
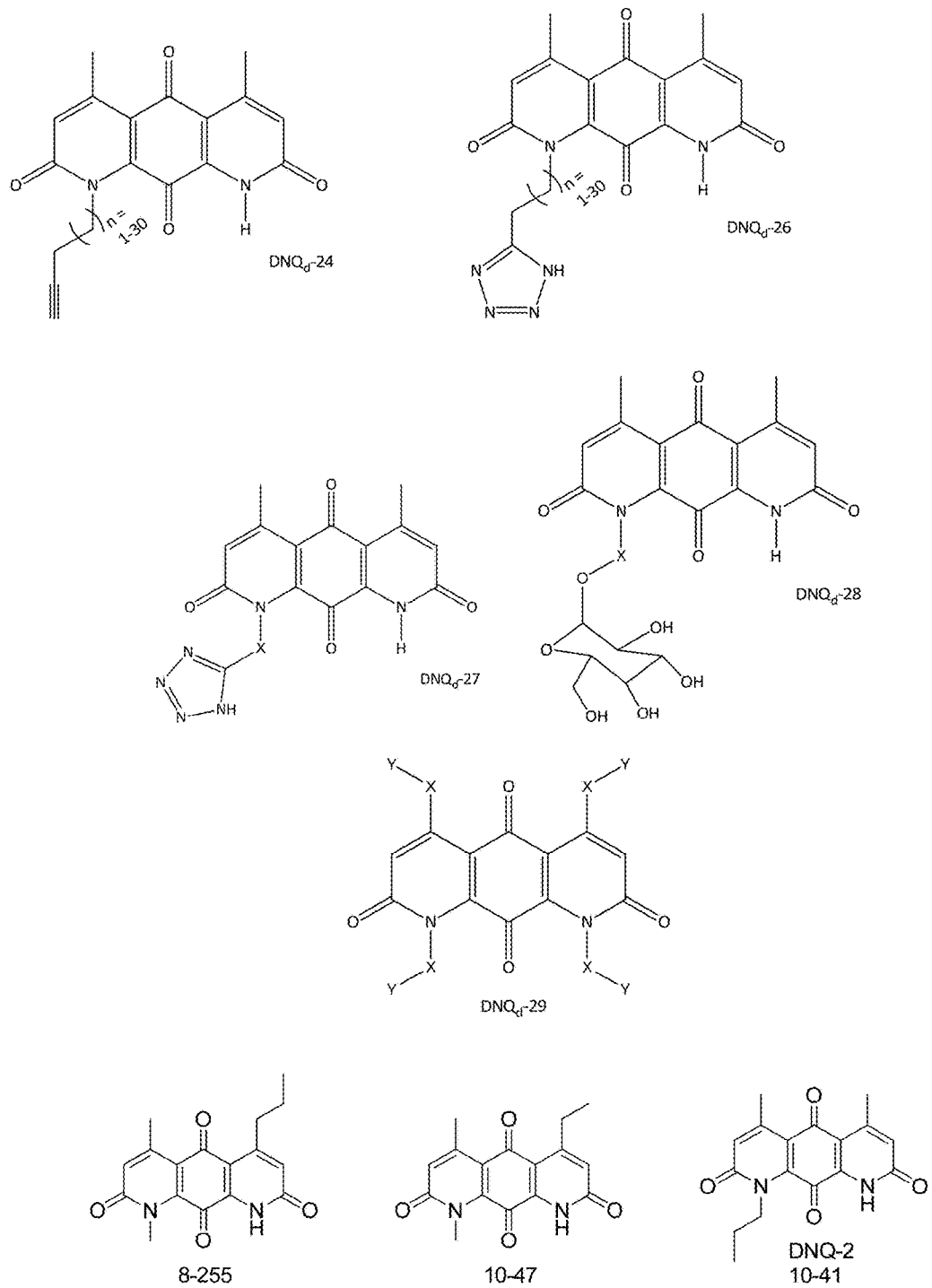
Figure 12:
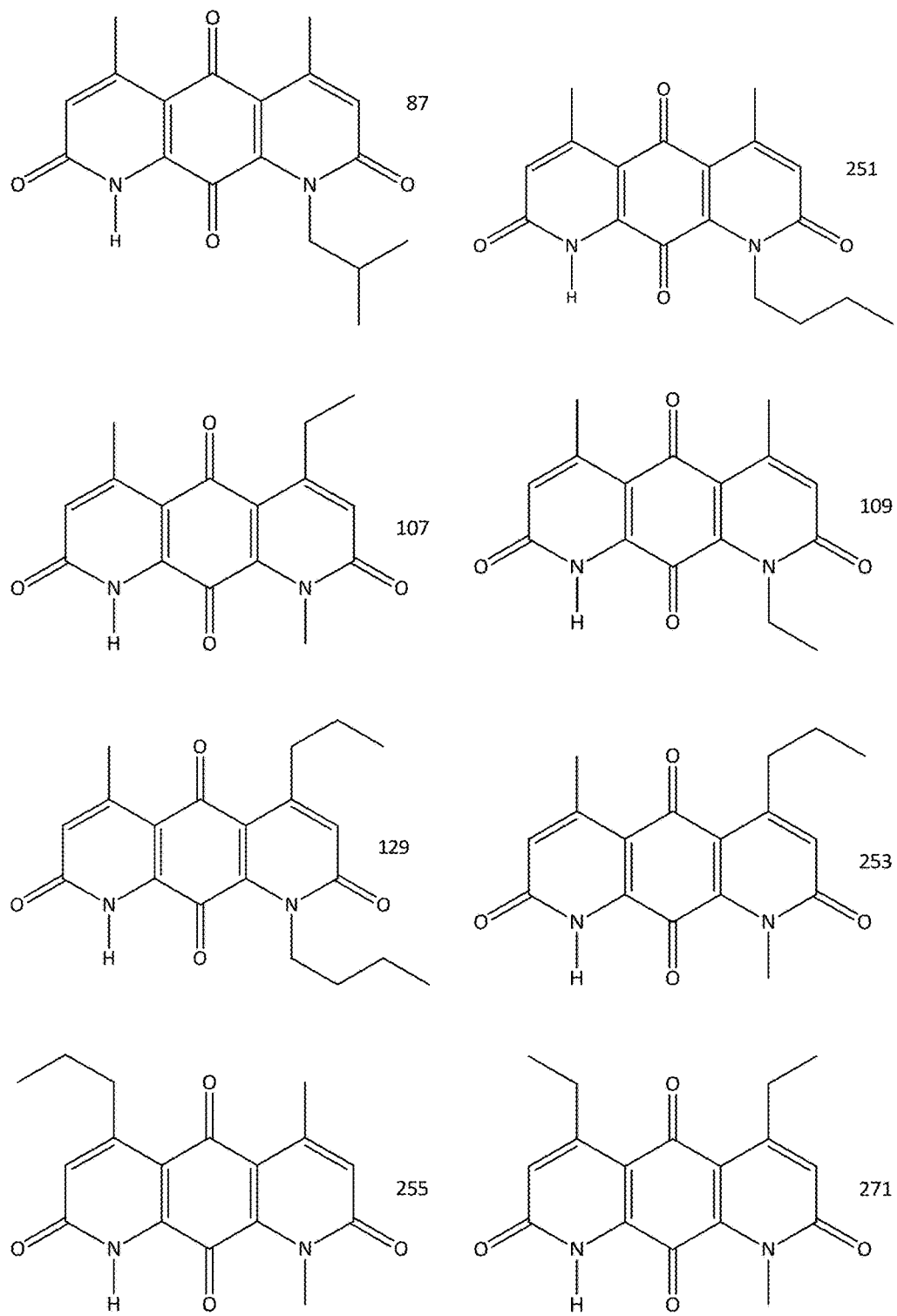
FIG. 12. Examples of specific DNQ compounds, according to various embodiments.
Figure 12:
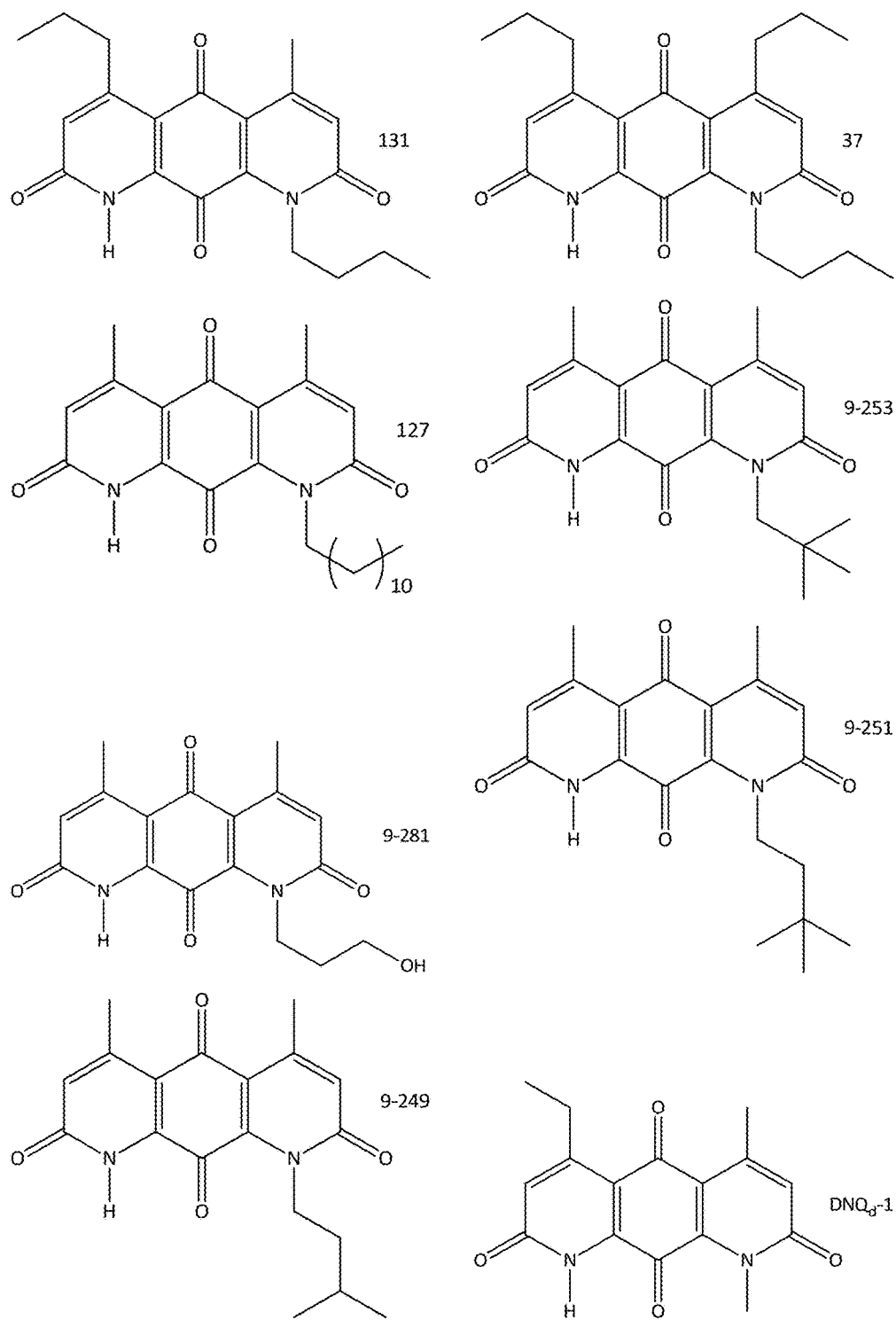
Figure 12:
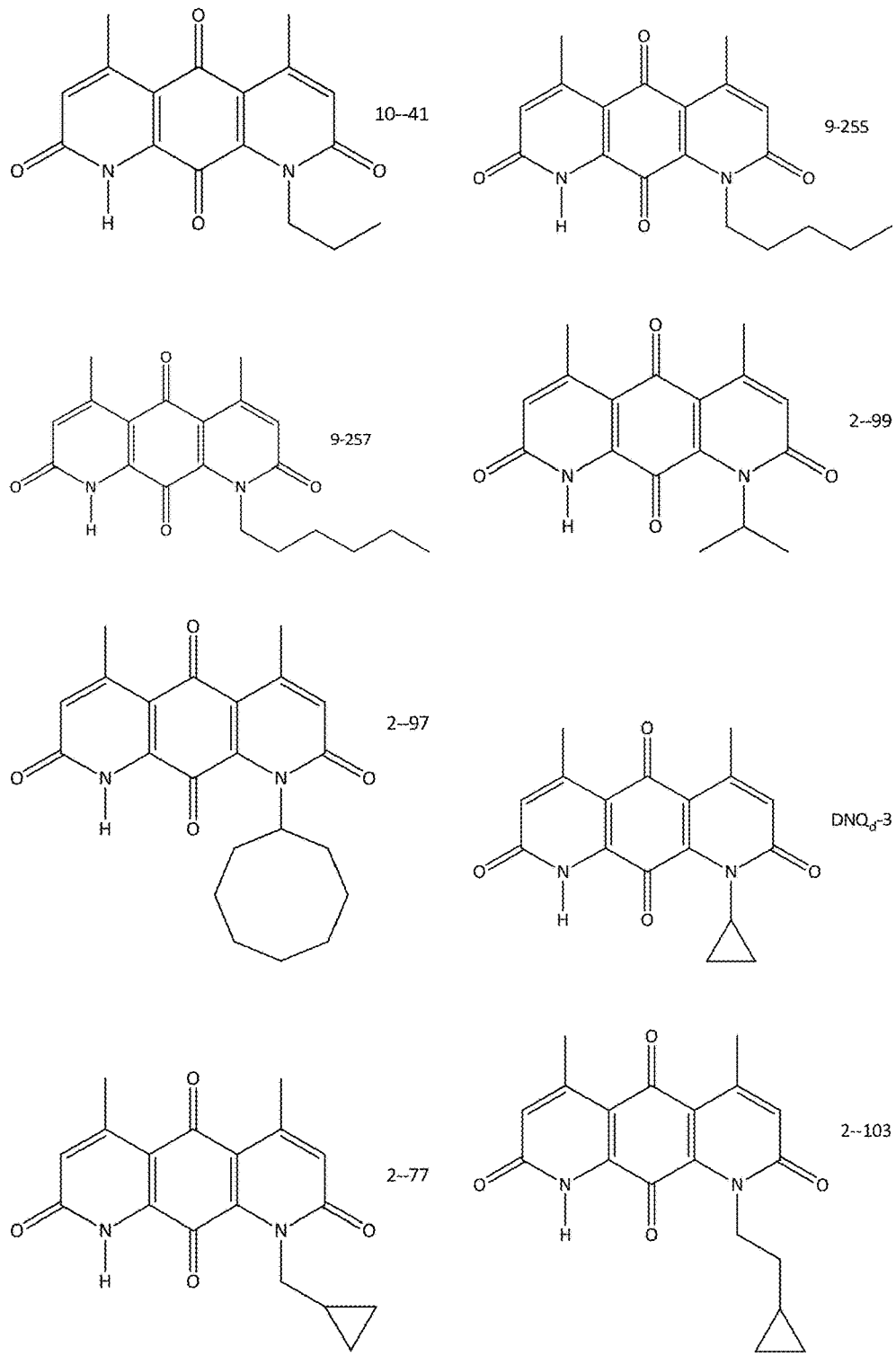
Figure 12:
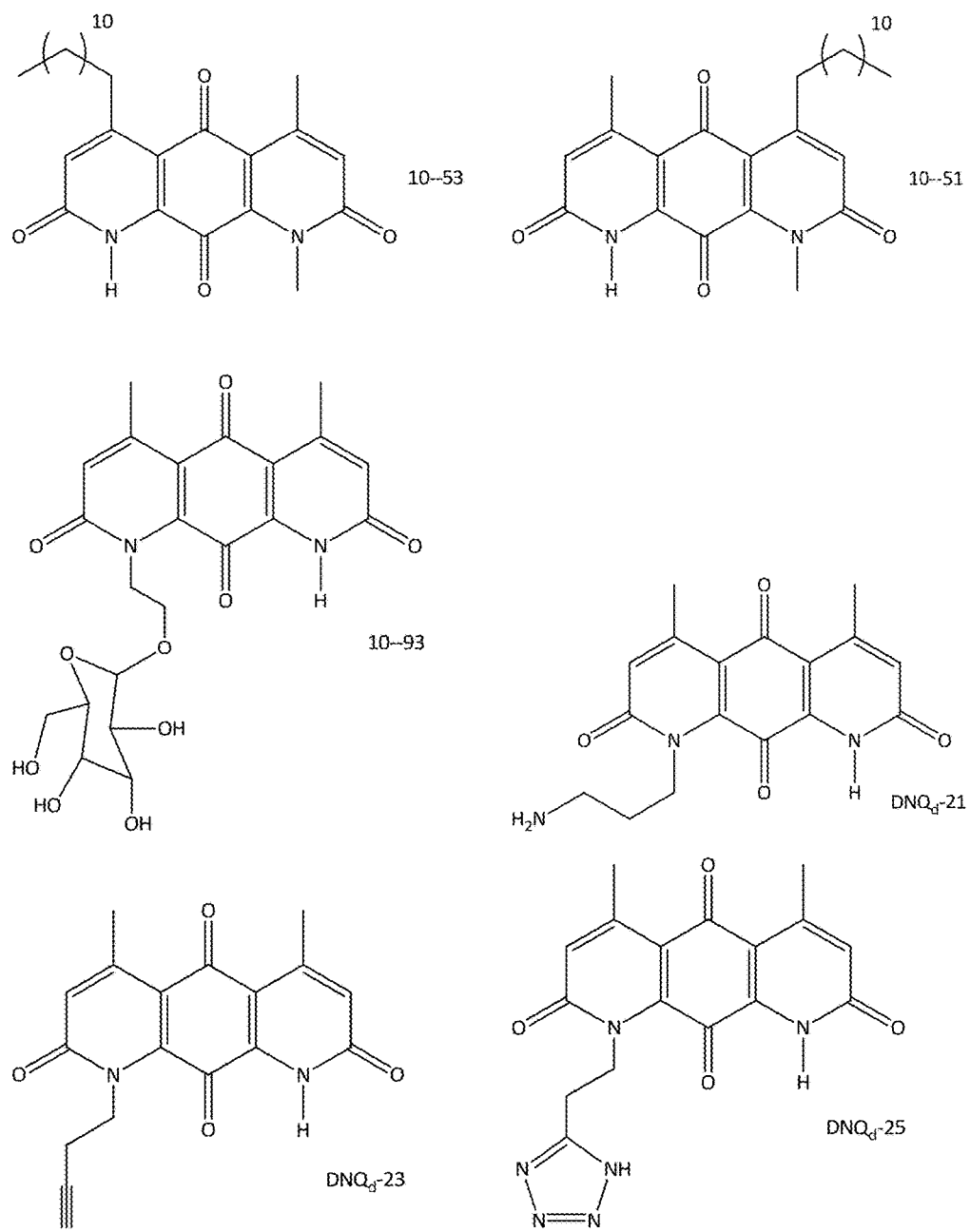
Figure 13A:
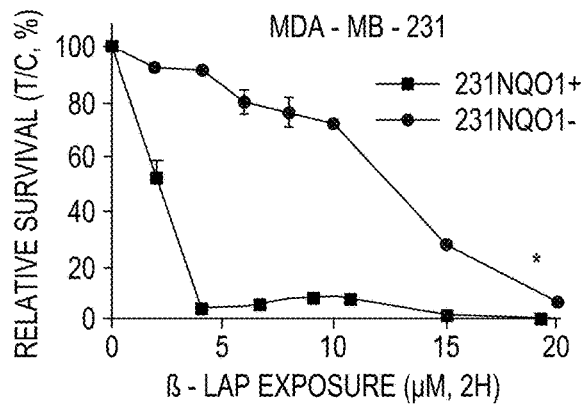
FIG. 13. DNQ87 (IB-DNQ) works at much lower doses versus ß-lapachone and at doses equivalent to the parental DNQ compound. It is effective against breast cancer cells in an NQO1-dependent manner, as well as triple-negative breast cancer cells (A-F, for various cell types).
Figure 13B:
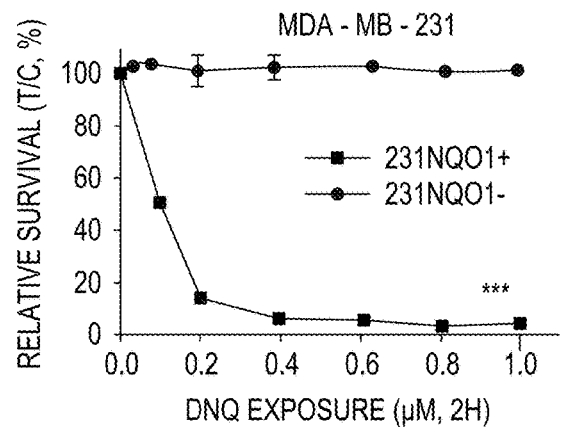
Figure 13C:
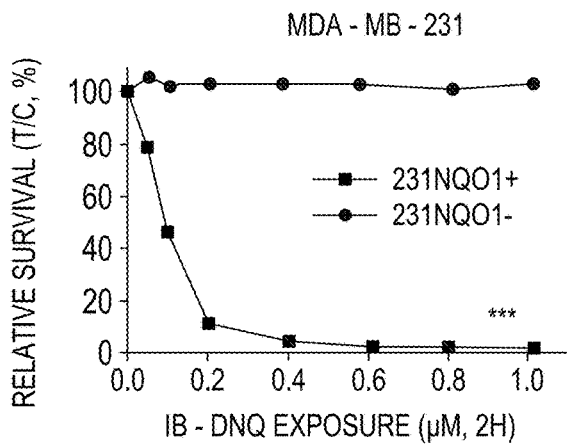
Figure 13D:
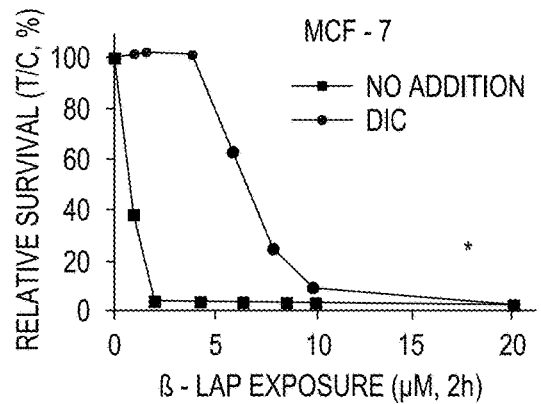
Figure 13E:
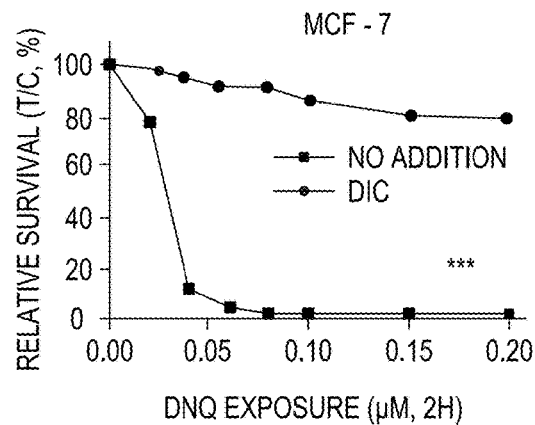
Figure 13F:
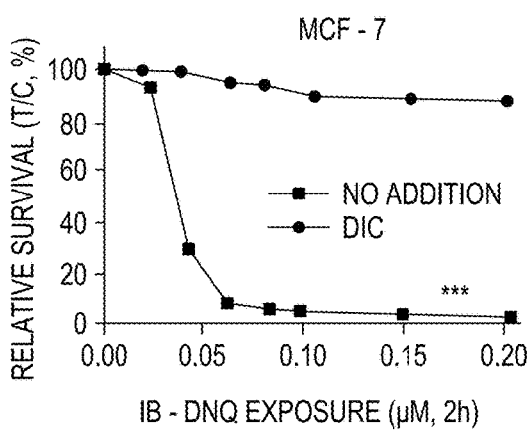
Figure 14A:
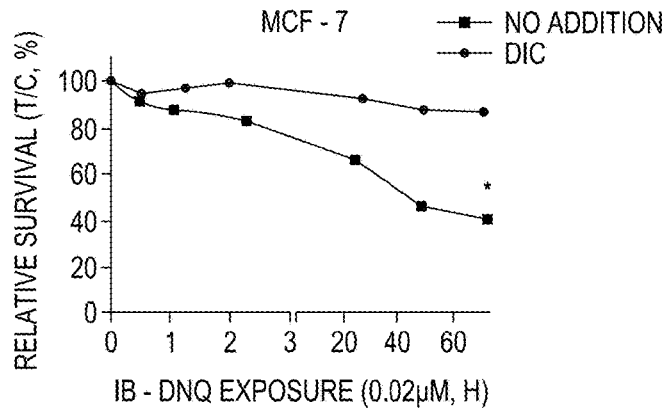
FIG. 14. Efficacy of DNQ87 increases in an NQO1-dependent manner (IB-DNQ exposure at various concentrations, A-H).
Figure 14B:
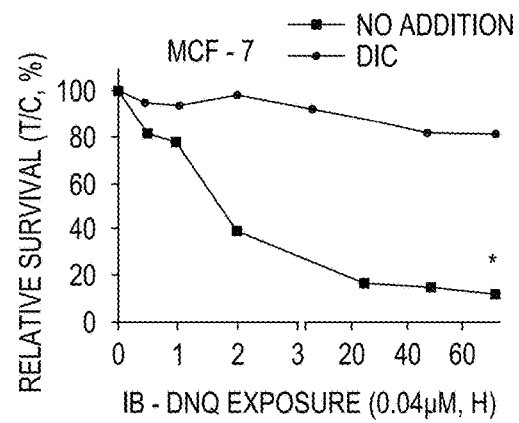
Figure 14C:
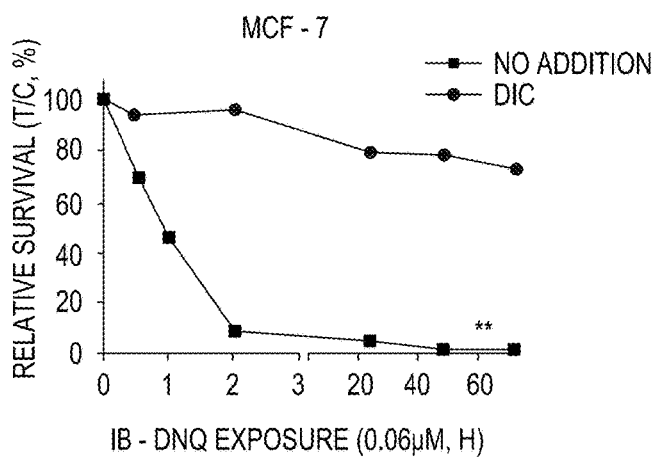
Figure 14D:
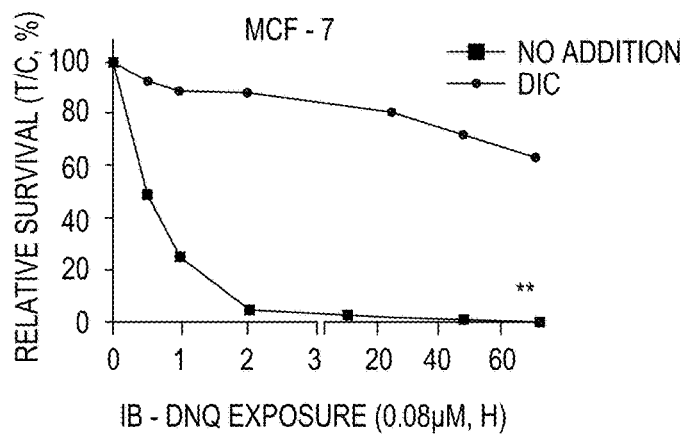
Figure 14E:
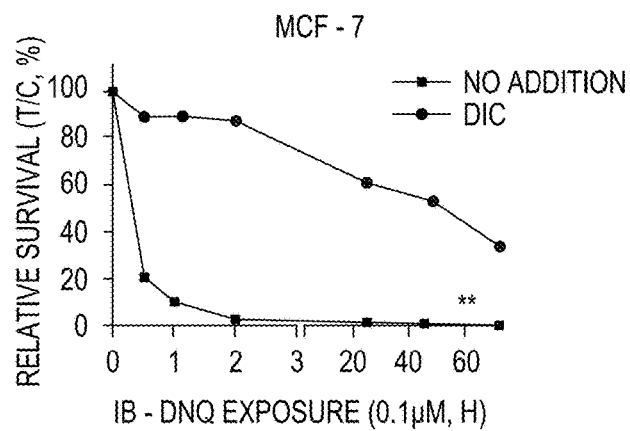
Figure 14F:
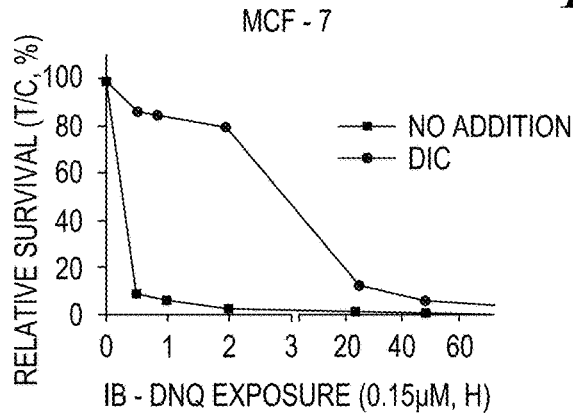
Figure 14G:
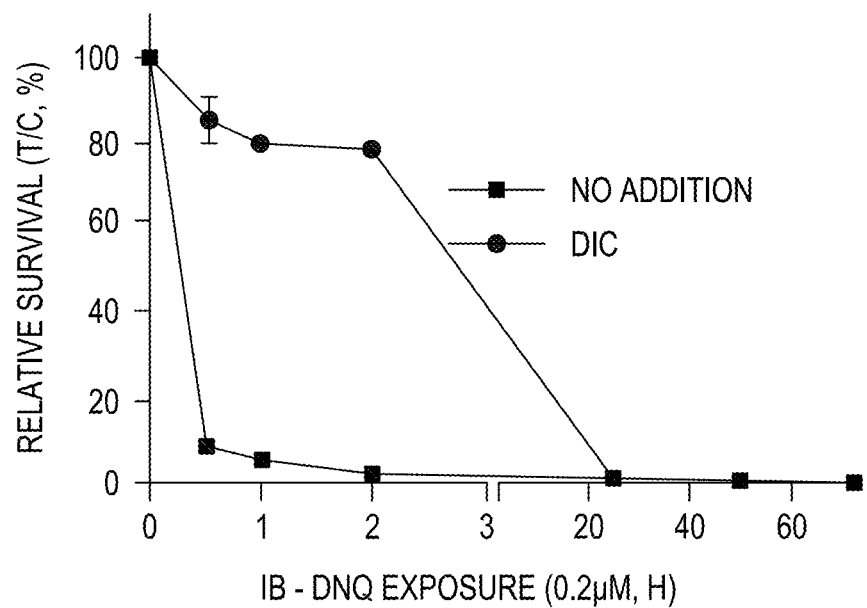
Figure 14H:
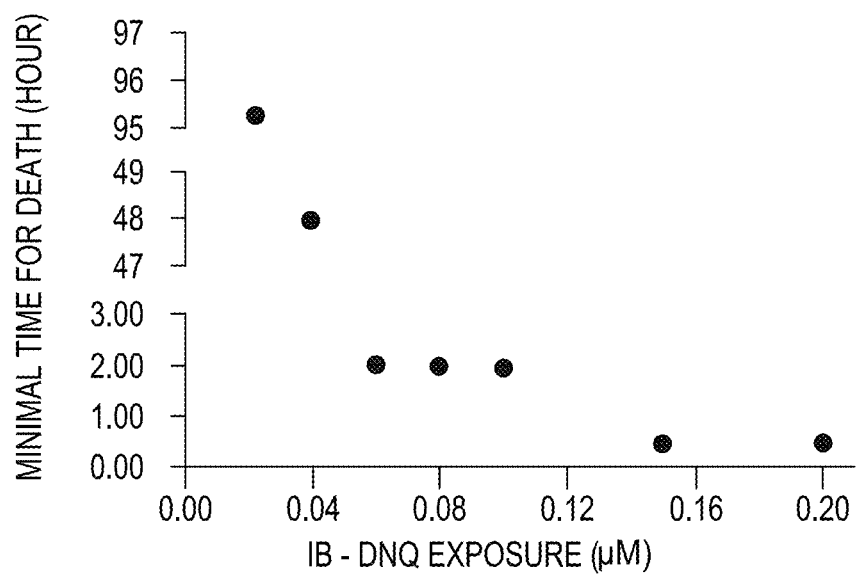
Figure 15A:
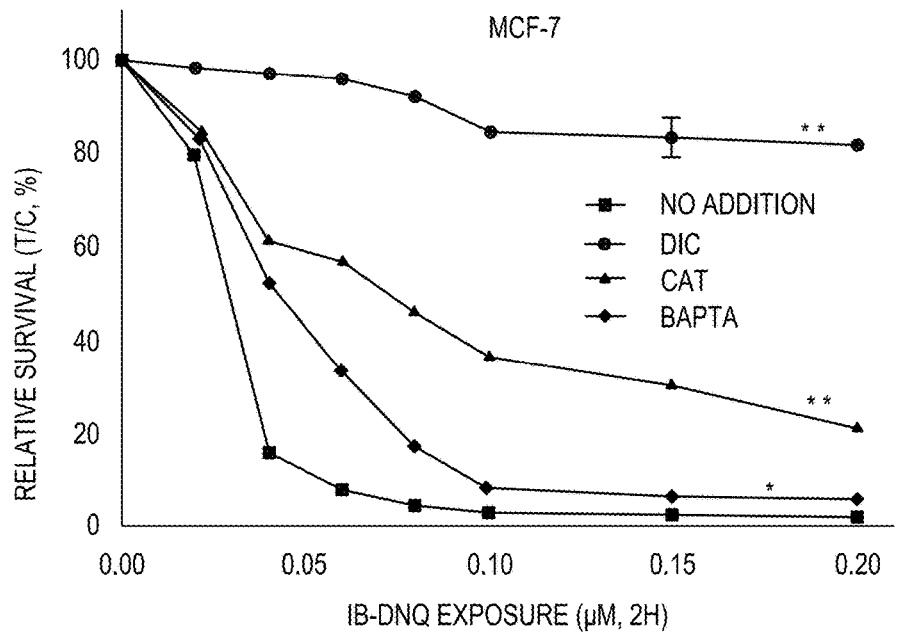
FIG. 15. IB-DNQ Cytotoxicity: "Noncaspase-mediated Cell Death". DNQ87 causes cell death that can be blocked by dicoumarol, catalase, and BAPTA-AM (a calcium chelator) (A), in descending order and consistent with the proposed pathway of cell death caused by NQO1 bioactivatable drugs (B). (C) PARP1 hyperactivation caused by DNQ87 exposure measured by PAR-PARP1 formation, highlighted by μ-calpain-mediated p53 cleavage (C) and atypical cleavage of PARP1 to ~60 kDa proteolytic fragments during cell death (D).
Figure 15B:
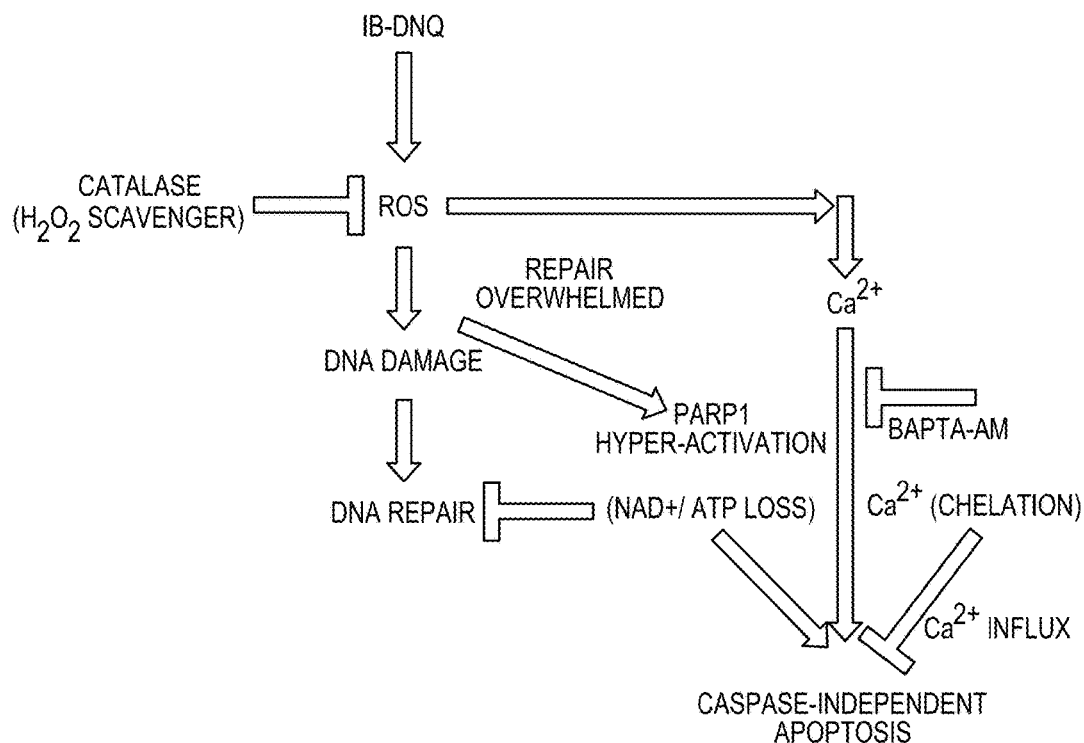
Figure 15C:
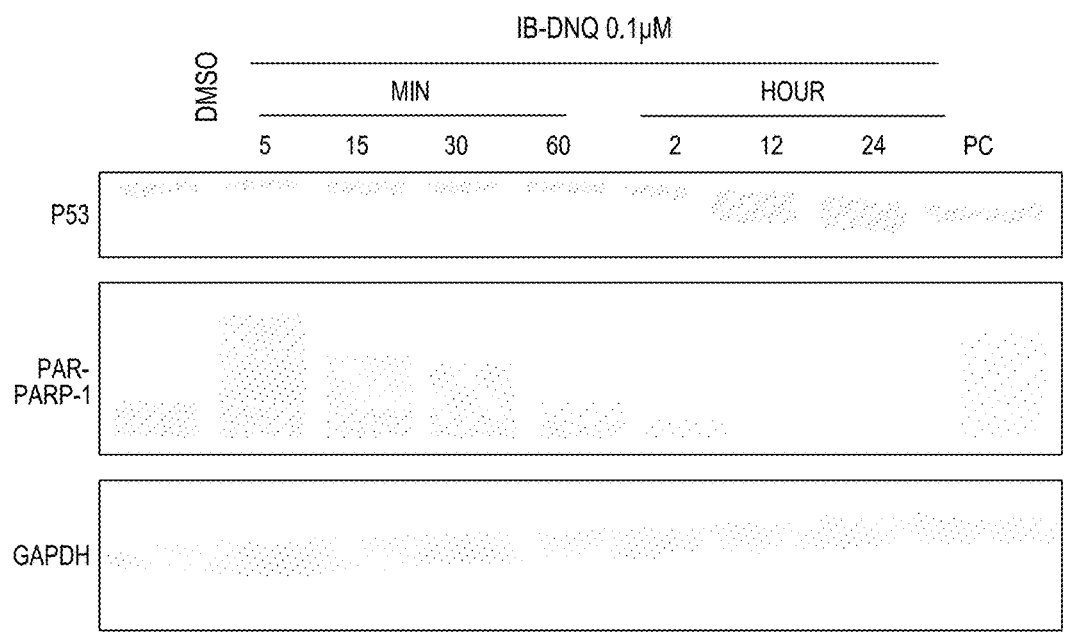
Figure 15D:
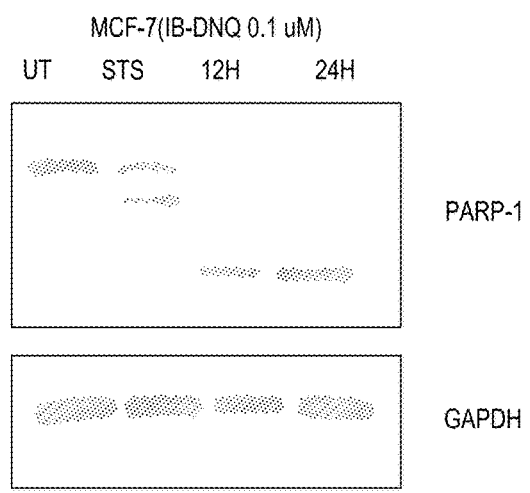
Figure 16A:
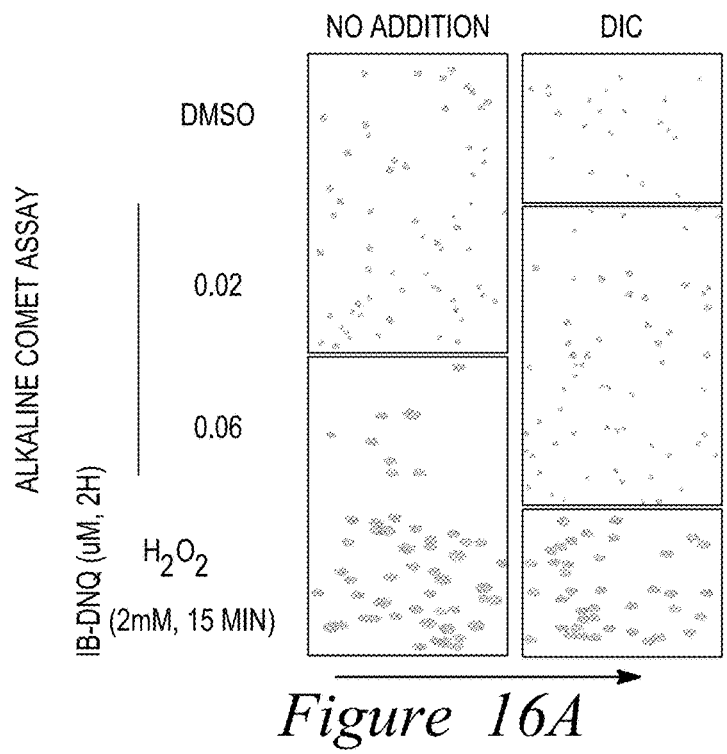
FIG. 16. DNQ87 causes DNA lesions (DNA double strand breaks) in a delayed manner, monitored by gamma-H2AX, phosphorylation of ATM at ser1981, and phosphorylation of DNA-PKcs at site Thr1892 (A-F).
Figure 16B:
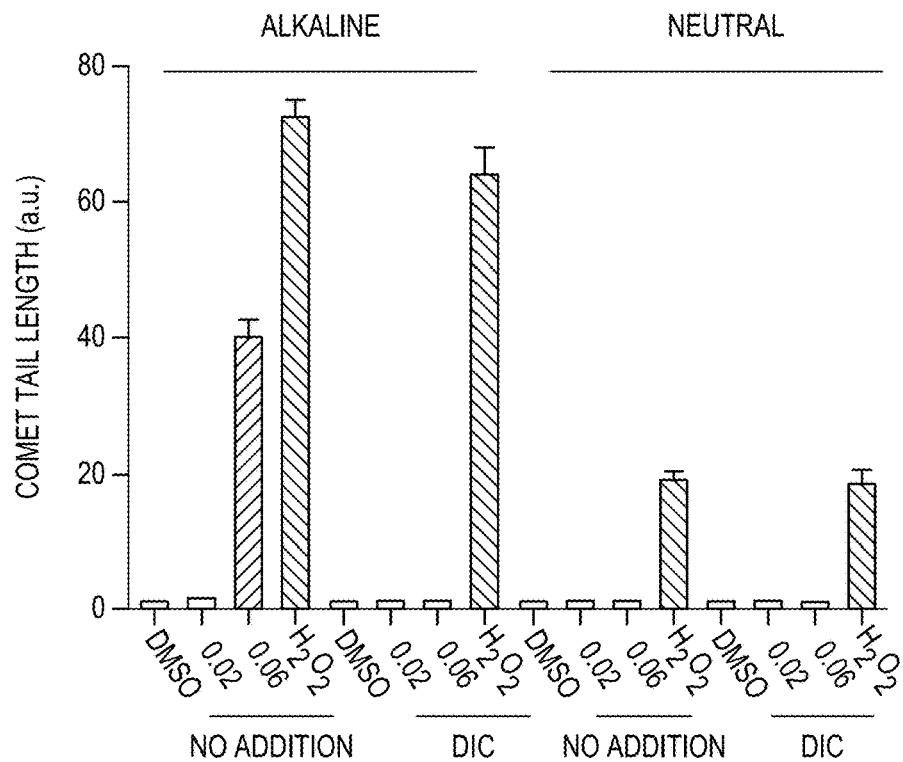
Figure 16C:
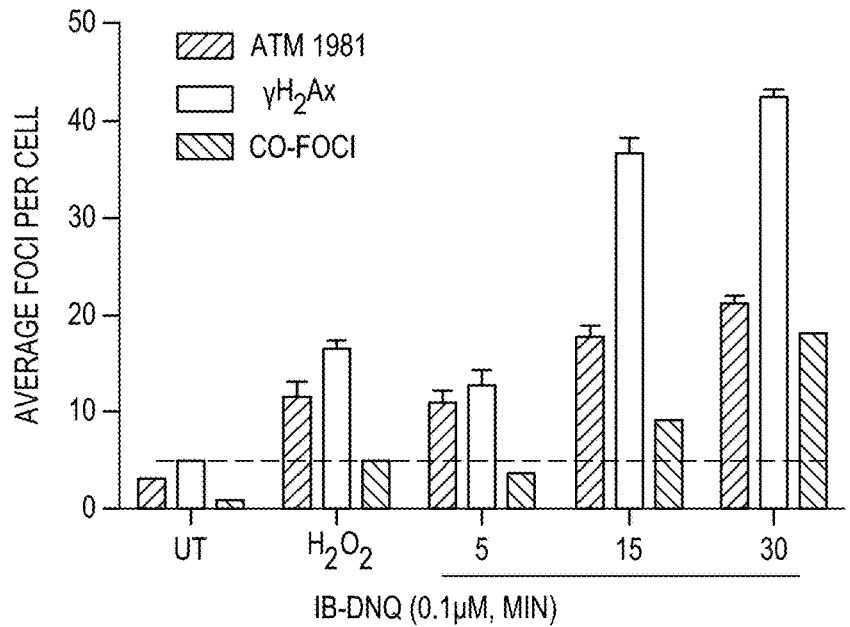
Figure 16D:
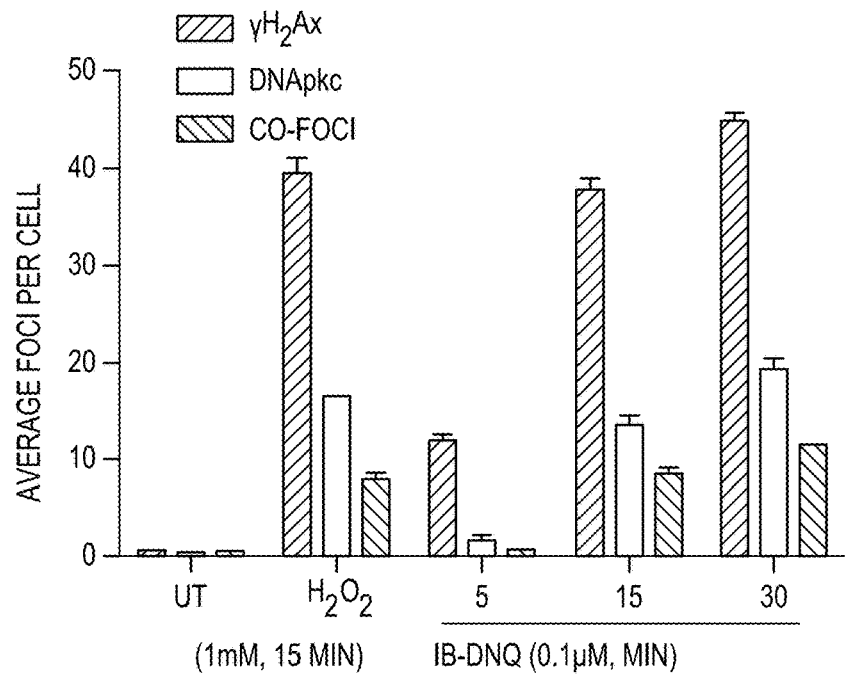
Figure 16E:
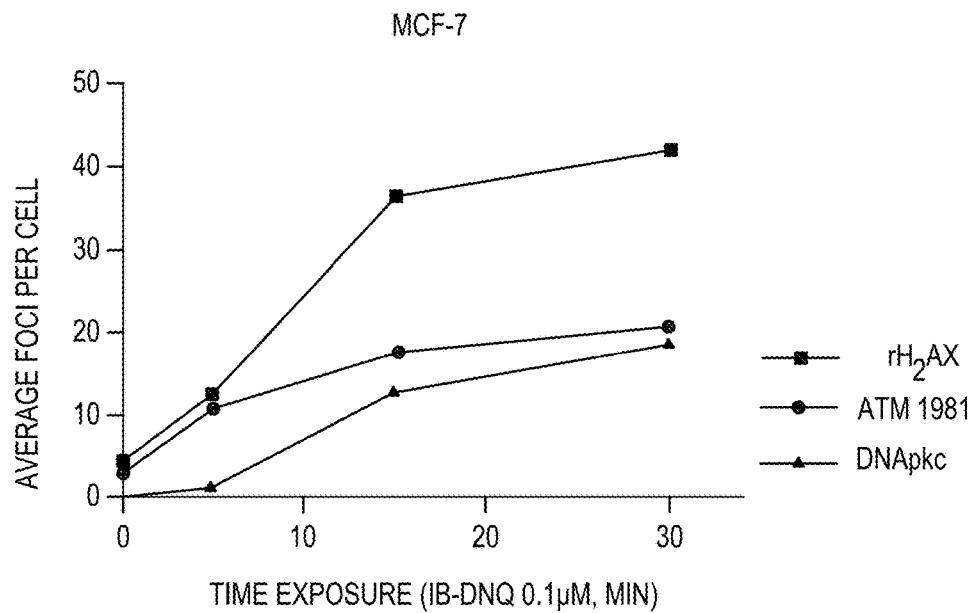
Figure 16F:
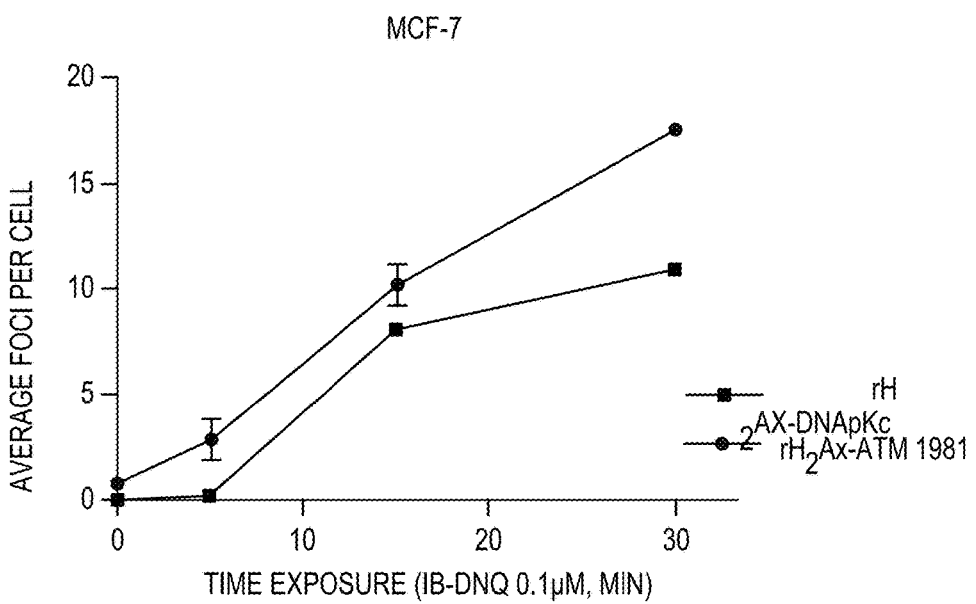

In some embodiments of Formula (I):

R$_1$ and R$_2$ are methyl; R$_3$ is hydrogen; and R$_4$ is 2-methylpropane;

R$_1$ and R$_2$ are methyl; R$_3$ is hydrogen; and R$_4$ is butyl;
R$_1$ and R$_4$ are methyl and R$_3$ is hydrogen; and R$_2$ is ethyl;
R$_1$ and R$_2$ are methyl and R$_3$ is hydrogen; and R$_4$ is ethyl;
R$_1$ is methyl; R$_3$ is hydrogen; R$_2$ is propyl; and R$_4$ is butyl;
R$_1$ and R$_4$ are methyl; R$_2$ is propyl and R$_3$ is hydrogen;
R$_1$ is propyl; R$_2$ and R$_4$ are methyl and R$_3$ is hydrogen;
R$_1$ and R$_2$ are ethyl; R$_3$ is hydrogen; and R$_2$ is methyl;
R$_1$ is propyl; R$_2$ is methyl; R$_3$ is hydrogen; and R$_4$ is butyl;
R$_1$ and R$_2$ are propyl; R$_3$ is hydrogen; and R$_4$ is butyl;
R$_1$ and R$_2$ are methyl; R$_3$ is hydrogen; and R$_4$ is C$_{12}$alkyl;
R$_1$ and R$_2$ are methyl; R$_3$ is hydrogen; and R$_4$ is tert-butyl;
R$_1$ and R$_2$ are methyl; R$_3$ is hydrogen; and R$_4$ is hydroxypropyl;
R$_1$ and R$_2$ are methyl; R$_3$ is hydrogen; and R$_4$ is 3,3-dimethylbutyl [—CH$_2$CH$_2$C(CH$_3$)$_2$CH$_3$];
R$_1$ and R$_2$ are methyl; R$_3$ is hydrogen; and R$_4$ is 3-methybutyl [—CH$_2$CH$_2$CH(CH$_3$)CH$_3$];
R$_2$ and R$_4$ are methyl; R$_3$ is hydrogen; and R$_1$ is ethyl;
R$_1$ and R$_2$ are methyl; R$_3$ is hydrogen; and R$_4$ is propyl;
R$_1$ and R$_2$ are methyl; R$_3$ is hydrogen; and R$_4$ is n-pentyl;
R$_1$ and R$_2$ are methyl; R$_3$ is hydrogen; and R$_4$ is n-hexyl;
R$_1$ and R$_2$ are methyl; R$_3$ is hydrogen; and R$_4$ is isopropyl;
R$_1$ and R$_2$ are methyl; R$_3$ is hydrogen; and R$_4$ is cyclooctyl;
R$_1$ and R$_2$ are methyl; R$_3$ is hydrogen; and R$_4$ is cyclopropyl;
R$_1$ and R$_2$ are methyl; R$_3$ is hydrogen; and R$_4$ is methylcyclopropyl;
R$_1$ and R$_2$ are methyl; R$_3$ is hydrogen; and R$_4$ is ethylcyclopropyl;
R$_1$ is C$_{12}$alkyl; R$_2$ and R$_4$ are methyl; and R$_3$ is hydrogen;
R$_1$ and R$_4$ are methyl; R$_3$ is hydrogen; and R$_2$ is C$_{12}$alkyl;
R$_1$, R$_2$, and R$_3$ are methyl; and R$_4$ is —CH$_2$OPO$_3$Na$_2$;
R$_1$ is —CH$_2$OPO$_3$Na$_2$; R$_2$ and R$_3$ are methyl; and R$_4$ is hydrogen;
R$_1$ and R$_3$ are methyl; R$_2$ is —CH$_2$OPO$_3$Na$_2$; and R$_4$ is hydrogen;
R$_1$ and R$_2$ are methyl; R$_3$ is —CH$_2$OPO$_3$Na$_2$; and R$_4$ is hydrogen;
R$_1$ and R$_2$ are methyl; R$_3$ is —CH$_2$CH$_2$OPO$_3$Na$_2$; and R$_4$ is hydrogen;
R$_1$, R$_2$, and R$_3$ are methyl; and R$_4$ is —CH$_2$OH;
R$_1$ is —CH$_2$OH; R$_2$ and R$_3$ are methyl; and R$_4$ is hydrogen;
R$_1$ and R$_3$ are methyl; R$_2$ is —CH$_2$OH; and R$_4$ is hydrogen;
R$_1$ and R$_2$ are methyl; R$_3$ is —CH$_2$OH; and R$_4$ is hydrogen; or
R$_1$ and R$_2$ are methyl; R$_3$ is —CH$_2$CH$_2$OH; and R$_4$ is hydrogen. Additional specific compounds and formulas of the invention are illustrated in FIGS. 11 and 12.

In certain embodiments of Formula I, R$^1$ is (C$_{1-4}$) alkyl group. In certain instances, R$^1$ is (C$_{1-3}$) alkyl group. In certain instances, R$^1$ is (C$_{1-2}$) alkyl group.

In certain embodiments of Formula I, R$^2$ is (C$_{1-4}$) alkyl group. In certain instances, R$^2$ is (C$_{1-3}$) alkyl group. In certain instances, R$^2$ is (C$_{1-2}$) alkyl group.

In certain embodiments of Formula I, R$^3$ is hydrogen.

In certain embodiments of Formula I, R$^4$ is an optionally substituted (C$_{1-10}$) alkyl group, where the alkyl group is substituted with hydroxyl, halogen, amino, or thiol. In certain instances, R$^4$ is (C$_{1-10}$) alkyl group, (C$_{1-8}$) alkyl group, (C$_{1-6}$) alkyl group, or (C$_{1-4}$) alkyl group. In certain instances, R$^4$ is (C$_{2-6}$) alkyl group. In certain instances, R$^4$ is a substituted (C$_{1-10}$) alkyl group, substituted (C$_{1-8}$) alkyl group, substituted (C$_{1-6}$) alkyl group, or substituted (C$_{1-4}$) alkyl group, where the alkyl group is substituted with hydroxyl, halogen, amino, or thiol. In certain instances, R$^4$ is an alkyl group is substituted with hydroxyl. In certain instances, R$^4$ is an alkyl group is substituted with halogen.

In certain instances, $R^4$ is an alkyl group is substituted with amino. In certain instances, $R^4$ is an alkyl group is substituted with thiol.

In certain embodiments of Formula I, $R^1$ and $R^2$ are independently ($C_{1-4}$) alkyl groups; $R^3$ is hydrogen; and $R^4$ is an optionally substituted ($C_{1-10}$) alkyl group, where the alkyl group is substituted with hydroxyl, halogen, amino, and thiol.

In certain embodiments of Formula I, $R^1$ and $R^2$ are independently ($C_{1-2}$) alkyl groups; $R^3$ is hydrogen; and $R^4$ is an optionally substituted ($C_{1-10}$) alkyl group, where the alkyl group is substituted with hydroxyl, halogen, amino, and thiol.

In certain embodiments of Formula I, $R^1$ and $R^2$ are independently ($C_{1-2}$) alkyl groups; $R^3$ is hydrogen; and $R^4$ is ($C_{1-10}$) alkyl group. In certain embodiments of Formula I, $R^1$ and $R^2$ are independently ($C_{1-2}$) alkyl groups; $R^3$ is hydrogen; and $R^4$ is ($C_{1-8}$) alkyl group. In certain embodiments of Formula I, $R^1$ and $R^2$ are independently ($C_{1-2}$) alkyl groups; $R^3$ is hydrogen; and $R^4$ is ($C_{1-6}$) alkyl group. In certain embodiments of Formula I, $R^1$ and $R^2$ are independently ($C_{1-2}$) alkyl groups; $R^3$ is hydrogen; and $R^4$ is ($C_{1-4}$) alkyl group. In certain embodiments of Formula I, $R^1$ and $R^2$ are independently ($C_{1-2}$) alkyl groups; $R^3$ is hydrogen; and $R^4$ is ($C_{2-6}$) alkyl group. In certain embodiments of Formula I, $R^1$ and $R^2$ are independently ($C_{1-2}$) alkyl groups; $R^3$ is hydrogen; and $R^4$ is a substituted ($C_{1-6}$) alkyl group, where the alkyl group is substituted with hydroxyl, halogen, amino, and thiol. In certain embodiments of Formula I, $R^1$ and $R^2$ are independently ($C_{1-2}$) alkyl groups; $R^3$ is hydrogen; and $R^4$ is a substituted ($C_{1-4}$) alkyl group, where the alkyl group is substituted with hydroxyl, halogen, amino, and thiol.

In certain embodiments, a compound of Formula I is Compound 87 or a salt or solvate thereof:

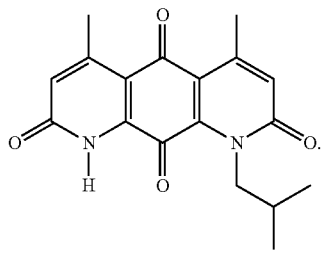 [SMILES: Cc1cc(=O)[nH]c2c1C(=O)c1c(C)cc(=O)n(CC(C)C)c1C2=O]

In certain embodiments, a compound of Formula I is Compound 9-253 or a salt or solvate thereof:

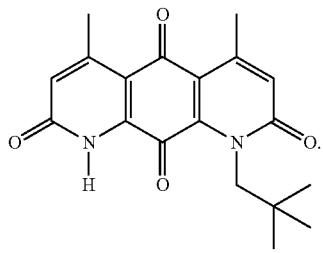 [SMILES: Cc1cc(=O)[nH]c2c1C(=O)c1c(C)cc(=O)n(CC(C)(C)C)c1C2=O]

In certain embodiments, a compound of Formula I is Compound 9-251 or a salt or solvate thereof:

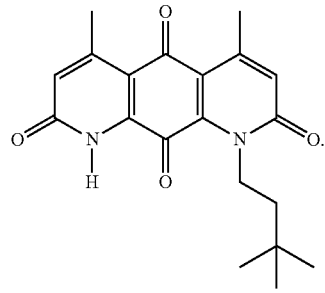 [SMILES: Cc1cc(=O)[nH]c2c1C(=O)c1c(C)cc(=O)n(CCC(C)(C)C)c1C2=O]

In certain embodiments, a compound of Formula I is Compound 10-41 or a salt or solvate thereof:

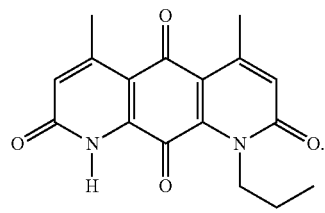 [SMILES: CCCn1c2c(c(C)cc1=O)C(=O)c1c(C)cc(=O)[nH]c1C2=O]

In certain embodiments, a compound of Formula I is Compound 109 or a salt or solvate thereof:

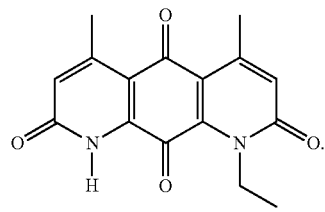 [SMILES: CCn1c2c(c(C)cc1=O)C(=O)c1c(C)cc(=O)[nH]c1C2=O]

In certain embodiments, a compound of Formula I is Compound 107 or a salt or solvate thereof:

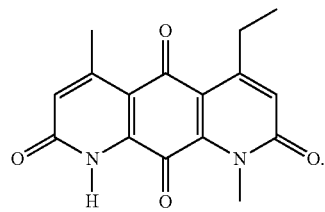 [SMILES: CCc1cc(=O)n(C)c2c1C(=O)c1c(C)cc(=O)[nH]c1C2=O]

In certain embodiments, a compound of Formula I is Compound 9-281 or a salt or solvate thereof:

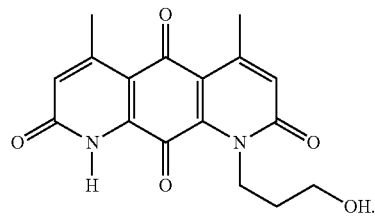 [SMILES: Cc1cc(=O)[nH]c2c1C(=O)c1c(C)cc(=O)n(CCCO)c1C2=O]

In certain embodiments, a compound of Formula I is Compound 9-249 or a salt or solvate thereof:

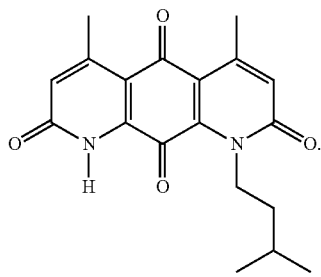 [SMILES: Cc1cc(=O)[nH]c2c1C(=O)c1c(C)cc(=O)n(CCC(C)C)c1C2=O]

In certain embodiments, a compound of Formula I is Compound 9-255 or a salt or solvate thereof:

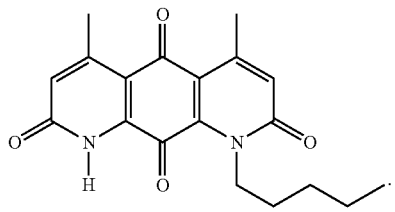 [SMILES: CCCCCn1c2c(c(C)cc1=O)C(=O)c1c(C)cc(=O)[nH]c1C2=O]

In certain embodiments, a compound of Formula I is Compound 9-257 or a salt or solvate thereof:

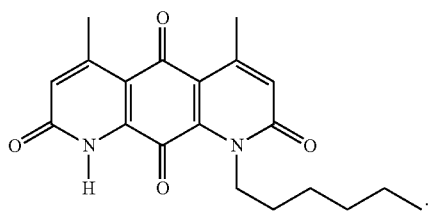 [SMILES: CCCCCCn1c2c(c(C)cc1=O)C(=O)c1c(C)cc(=O)[nH]c1C2=O]

The invention also provides a pharmaceutical composition comprising a compound of Formula (I) and a pharmaceutically acceptable diluent, excipient, or carrier. The carrier can be water, for example, in the presence of hydroxypropyl-β-cyclodextrin (HPβCD). The solubility of the compound can be increase by about 100 times, about 200 times, about 500 times, about 1000 times, about 2000 times, or about 3000 times, compared to the compounds solubility in water without HPβCD. Additional DNQ compounds and methods are described by International Application No. PCT/US12/59988 (Hergenrother et al.).

As to any of the above formulas or groups that contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents of the compounds described herein may be present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above. In some embodiments, recursive substituents are present only to the extent that the molecular mass of the compound is about 400 to about 1600, about 450 to about 1200, about 500 to about 100, about 600 to about 800. In other embodiments, recursive substituents are present only to the extent that the molecular mass of the compound is less than 2000, less than 1800, less than 1600, less than 1500, less than 1400, less than 1200, less than 1000, less than 900, less than 800, less than 750, less than 700, or less than about 600.

Patients with solid tumors having elevated NQO1 levels can be treated through the administration of an effective amount of a pharmaceutically active form of DNQ and/or $DNQ_d$ (DNQ compounds). DNQ and $DNQ_d$ compounds can be, for example, a compound defined by one of the formulas of FIG. 11, or a compound illustrated in FIG. 12. In FIG. 11 where n=1-30, the value of n can be 1 or any integer from 1 up to about 30. Thus, the range 1-30 includes each individual integer from 1 to 30 and any ranges from any one to any second number from 1 to 30. In each range described herein, a portion of the range may also be excluded from the embodiment defined. For example, in various embodiments, a variable n can be 6-24, and another n variable of the same formula can be 1-24.

In FIG. 11 for $DNQ_d$-20, $R_1$, $R_2$, and $R_3$ can be as defined for Formula I above. In various embodiments, $R_1$, $R_2$, and $R_3$ can also each independently be $C_{1-20}$ alkyl, or each of $R_1$, $R_2$ or $R_3$ can be independently be linked to the anomeric position of a hexose, optionally through a linker, such as a linker of formula W-A-W— or a $(C_1-C_{10})$alkylene group.

In FIG. 11 for $DNQ_d$-27 and $DNQ_d$-28, X can be a linker of formula —W-A-W— or a divalent bridging group such as a divalent alkyl, alkenyl, alkynyl, heteroalkyl, acycloalkyl, cycloalkenyl, heterocycloalkyl, heterocycloalkenyl, cycloalkylalkyl, heterocycloalkylalkyl, cycloalkylheteroalkyl, heterocycloalkylheteroalkyl, alkoxy, alkoxyalkyl, alkenyloxy, alkynyloxy, cycloalkylkoxy, heterocycloalkyloxy, amino, alkylamino, aminoalkyl, acylamino, arylamino, sulfonylamino, sulfinylamino, alkoxycarbonyl, alkylaminocarbonyl, sulfonyl, alkylsulfonyl, alkylsulfinyl, arylsulfonyl, arylsulfinyl, aminosulfonyl, or acyl, each of which may be optionally substituted.

In FIG. 11 for $DNQ_d$-29, each X can independently be a linker of formula —W-A-W— or a divalent bridging group as described above for $DNQ_d$-27 and $DNQ_d$-28; and each Y can independently be:

(1) Hydroxyl, (11) Acetate, (21) Nitroso,
(2) Aldehyde, (12) Amino, (22) Pyridyl,
(3) Carboxyl, (13) Azide, (23) Sulfhydryl,
(4) Haloformyl, (14) Azo, (24) Sulfonic acid,
(5) Hydroperoxy, (15) Cyano, (25) Sulfonate,
(6) Phenyl, (16) Isocyanato, (26) Isothiocyanato,
(7) Benzyl, (17) Nitrate, (27) Phosphine,
(8) Alkyl, (18) Isonitrile, (28) Phosphate, (9) Alkenyl, (19) Nitrosooxy, (29) Halo, or

(10) Alkynyl, (20) Nitro, (30) Hexose.

The invention also provides methods of treating a patient that has tumor cells having elevated NQO1 levels. The methods can include administering to a patient having tumor cells with elevated NQO1 levels a therapeutically effective amount of a compound of Formula (I), or a composition described herein. The invention further provides methods of treating a tumor cell having an elevated NQO1 level comprising exposing the tumor cell to a therapeutically effective amount of a compound or composition described herein, wherein the tumor cell is treated, killed, or inhibited from growing. The tumor or tumor cells can be malignant tumor cells. In some embodiments, the tumor cells are cancer cells, such as Non-Small-Cell Lung Carcinoma.

The methods of the invention may be thus used for the treatment or prevention of various neoplasia disorders including acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. Accordingly, the compositions and methods described herein can be used to treat bladder cancer, brain cancer (including intracranial neoplasms such as glioma, meninigioma, neurinoma, and adenoma), breast cancer, colon cancer, lung cancer (SCLC or NSCLC) ovarian cancer, pancreatic cancer, and prostate cancer.

Methods of Making the Compounds of the Invention

The invention also relates to methods of making the compounds and compositions of the invention. The compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, La rock, R. C., Second Edition, John Wiley & Sons, New York (1999).

A number of exemplary methods for the preparation of the compositions of the invention are provided below. These methods are intended to illustrate the nature of such preparations are not intended to limit the scope of applicable methods. Additional methods and useful techniques are described in WO 2013/056073 (Hergenrother et al.).

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product. Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group. The particular removable blocking group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of Formula (I) can also be protecting groups, as described herein.

Suitable hydroxyl protecting groups are known to those skilled in the art and disclosed in more detail in T. W.

Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Salts and Solvates

Pharmaceutically acceptable salts of compounds described herein are within the scope of the invention and include acid or base addition salts which retain the desired pharmacological activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. $Na^+$, $Li^+$, $K^+$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Examples of suitable salts of the compounds described herein include their hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates.

Pharmaceutical Compositions

The following describes information relevant to pharmaceutical and pharmacological embodiments and is further supplemented by information in the art available to one of ordinary skill. The exact formulation, route of administration and dosage can be chosen by an individual physician or clinician in view of a patient's condition (see e.g., Fingl et al., in *The Pharmacological Basis of Therapeutics*, 1975, Ch. 1).

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995) and elsewhere in the art.

The compounds can be administered to a patient in combination with a pharmaceutically acceptable carrier, diluent, or excipient. The phrase "pharmaceutically acceptable" refers to those ligands, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" includes any and all solvents, dispersion media, diluents, coatings, surfactants, antioxidants, preservatives (e.g., antibacterial agents, antifungal agents), isotonic agents, absorption delaying agents, salts, buffers, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference). Except insofar as any conventional carrier is incompatible with the active ingredient, its use in the chemotherapeutic or pharmaceutical compositions is contemplated.

A $DNQ_d$ or DNQ compound may be combined with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, *Remington's Pharmaceutical Sciences*, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

When administered to a subject, effective amounts will depend, of course, on the particular cancer being treated; the genotype of the specific cancer; the severity of the cancer; individual patient parameters including age, physical condition, size and weight, concurrent treatment, frequency of treatment, and the mode of administration. These factors are well known to the physician and can be addressed with no more than routine experimentation. In some embodiments, it is preferred to use the highest safe dose according to sound medical judgment.

In certain embodiments, pharmaceutical compositions may comprise, for example, at least about 0.1% of a $DNQ_d$ or DNQ compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

Actives described herein such as $DNQ_d$ or DNQ compounds may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, triethylamine, histidine or procaine.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are optionally provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose (HPC); or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose.

The composition should be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Formulation of DNQ Compounds for In Vivo Administration

The aqueous solubility of DNQ at pH 7.4 in phosphate buffered saline (PBS) was measured by LC-MS. DNQ was sonicated for 30 minutes in PBS then undissolved solid was removed by filtration through a 0.45 µm syringe filter and the filtrate was analyzed by LC-MS ($\lambda$=275 nm, ESI-TOF in negative mode). The optimal sonication time was determined by sonicating DNQ for 1, 5, 10, and 30 minutes. While the concentration of DNQ in solution increased substantially between 1, 5, and 10 minutes, there was only a minor difference between 10 and 30 minutes. During the 30 minute sonication the water bath warmed to 45° C. (samples were cooled to room temperature before filtration). A calibration curve was generated from 1-100 µM by dissolving DNQ in methanol to a concentration of 500 µM and making dilutions of this stock in 80:20 water: methanol. The calibration curve (measure by UV absorbance) was linear over this range; 1 µM was approximately the limit of detection. The solubility of DNQ in PBS was measured to be 115 µM. The solution was very pale yellow.

Because of the poor aqueous solubility of DNQ we investigated the use of 2-hydroxypropyl-beta-cyclodextrin (HPβCD), a common excipient, to improve the solubility of DNQ. In the absence of HPβCD, the solubility of DNQ increases significantly in strongly basic solutions and DNQ precipitates when the pH is returned to neutral. However, in the presence of a sufficient amount of HPβCD, DNQ does not precipitate when the pH is returned to neutral. This same neutral solution of DNQ in HPβCD cannot be made directly (i.e. without pH adjustment). This indicates that DNQ compounds deprotonate in base and this deprotonated molecule forms a tight complex with HPβCD which is stable enough to prevent protonation as the pH decreases. The only proton on DNQ that might reasonably be deprotonated in aqueous base is the N—H. Although the acidity of the N—H bond of DNQ has not been measured, it has been measured for a derivative of DNQ and found to have a pKa of 8.0.

The protocol for formulating DNQ compounds in HPβCD is as follows: the DNQ compound is slurried in a 20% solution of HPβCD in pH 7.4 PBS and the pH is then increased by the addition of 10 M NaOH to induce dissolution of the DNQ compound. The pH is returned to pH 7.5-8.0 by the careful addition of 1 M HCl. A 3.3 mM solution of the DNQ compound can be made by this method which is stable at least 24 hours. This represents a 30-fold increase in solubility of DNQ over PBS alone. We initially chose a 20% HPβCD solution. However, we have found that β-lap was formulated as a 40% solution of HPβCD for human clinical trials and our experience with DNQ indicates that the concentration of DNQ increases linearly with that of HPβCD; thus a 40% HPβCD solution would permit the creation of a 6.6 mM solution of DNQ and other DNQ compounds.

Combination Therapy

Active ingredients described herein (e.g., compounds of Formula (I)) can also be used in combination with other active ingredients. Such combinations are selected based on the condition to be treated, cross-reactivities of ingredients and pharmaco-properties of the combination. For example, when treating cancer, the compositions can be combined with other anti-cancer compounds (such as paclitaxel or rapamycin).

It is also possible to combine a compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Combination therapy is further described by U.S. Pat. No. 6,833,373 (McKearn et al.), which includes additional active agents that can be combined with the compounds described herein, and additional types of cancer and other conditions that can be treated with a compound described herein.

Accordingly, it is an aspect of this invention that a $DNQ_d$ or DNQ can be used in combination with another agent or therapy method, preferably another cancer treatment. A $DNQ_d$ or DNQ may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the active agent(s). In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the active agent(s). In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the active agent(s). In some situations, it may be desirable to extend the time period for treatment significantly, however, where several weeks (e.g., about 1, about 2, about 3, about 4, about 6, or about 8 weeks or more) lapse between the respective administrations.

Administration of the chemotherapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described active agent(s). These therapies include but are not limited to chemotherapy, radiotherapy, immunotherapy, gene therapy and surgery.

Chemotherapy

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib hydrochloride), antibodies to EGFR, GLEEVEC™ (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, teniposide, 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux™ (cetuximab), Liposomal, Thiotepa, Altretamine, Melphalan, Trastuzumab, Lerozole, Fulvestrant, Exemestane, Fulvestrant, Ifosfomide, Rituximab, C225, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, paclitaxel, gemcitabine, navelbine, farnesyl-protein transferase inhibitors, transplatinum, 5-fluorouracil, vincristine, vinblastine and methotrexate, or any analog or derivative variant of the foregoing.

Radiotherapy.

Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (e.g., 3 to 4 wks), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy.

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Surgery.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following Examples are intended to illustrate the above invention and should not be construed to narrow its scope. One skilled in the art will readily recognize that the Examples suggest many other ways in which the invention could be practiced. It should be understood that numerous variations and modifications may be made while remaining within the scope of the invention. The invention may be further understood by the following non-limiting examples.

Abbreviations used in the Schemes and Examples may include the following:
A549=adenocarcinomic human alveolar basal epithelial cells
ATP=adenosine triphosphate
β-lap=β-lapachone
DHE=dihydroethidium
DNQ=Deoxynyboquinone
$DNQ_d$=Any analog or derivative of deoxynyboquinone
ELISA=enzyme-linked immunosorbent assay
h=hour(s)
H596=[NCI-H596] human lung adenosquamous carcinoma cell line
HT1080=primate fibrosarcoma cell line
$LD_{50}$=lethal dose having 50% probability of causing death
$LD_{90}$=lethal dose having 90% probability of causing death
$LD_{100}$=lethal dose having 100% probability of causing death
MCF-7=human breast adenocarcinoma cell line
MDA-MB-231=human breast cancer cell line
MIA-PaCa2=Pancreatic cancer cell line
mins=minute(s)
NADH=nicotinamide adenine dinucleotide
NQO1=NAD(P)H:quinone oxidoreductase 1
NSCLC=non-small-cell lung cancer cells
OCR=oxygen consumption rates
p53=a tumor suppressor protein
PC-3=human prostate cancer cell line
ROS=reactive oxygen species
±SE=standard error
siRNA=small interfering ribonucleic acid
shRNA=small hairpin ribonucleic acid
μM=micromolar
nM=nanomolar
μmol=micromole

EXAMPLES

Example 1. Base Excision Repair Inhibition Synergistically Enhances β-Lapachone-Mediated Cell Death for Tumor-Selective Therapy of Pancreatic Cancer Blocking DNA base excision (BER) or SSB repair processes with PARP1 inhibitors can dramatically increase efficacy, and significantly lower required doses, of NQO1 bioactivatable drugs against NQO1+ over-expressing cancers such as pancreatic cancers. To demonstrate these methods, experiments were performed to mechanistically show that inhibiting BER or SSB repair synergizes with NQO1 bioactivatable drugs against NQO1+ vs. NQO1- or shRNA knockdown pancreatic cancer cells in vitro. Additionally, experiments were performed to optimize MeOX or PARP1 inhibitors to enhance NQO1 bioactivatable drug efficacy in vivo. The combination therapy can thus be used as a tumor-specific approach using DNA repair inhibitors (e.g., BER and PARP1 inhibitors).

This example demonstrates the tumor-specific efficacy of NQO1 bioactivatable drugs against pancreatic, as well as other NQO1-overexpressing cancers; and demonstrates 'tumor-specificity' for PARP1 inhibitors outside current, limited, 'synthetic lethal' approaches for cancer therapy.

The synergistic effects of adding methoxyamine (MeOX) with β-lap against NQO1 over-expressing pancreatic cancer cells were examined. MeOX+β-lap synergy resulted in: a, enhanced lethality of sub-lethal doses of β-lap, reducing the shoulder (Dq), increasing the lethality rate (Do), and inducing apoptosis (TUNEL+) in NQO1+, but not in NQO1-, MIA PaCa-2 pancreatic cells; b, increased DNA lesion formation only in tumor cells; c, dramatic losses in ATP levels, with little recovery; and d, dramatic suppression of glycolysis. Thus, MeOX enhances PARP1 hyperactivation and synergistic cell killing by β-lap. Similar results were noted in shRNA-XRCC1 knockdown cells. However, Ogg1 knockdown cells were rendered resistant to ß-lap. Mechanistically, the data indicate that PARP1 detects MeOX-AP modified sites or SSBs, allowing PARP1 hyperactivation and synergistic cell death. Because MeOX is a nontoxic agent, the combination of agents can provide therapies for the treatment of pancreatic, as well as other NQO1 overexpressing solid cancers.

Figure 2A:
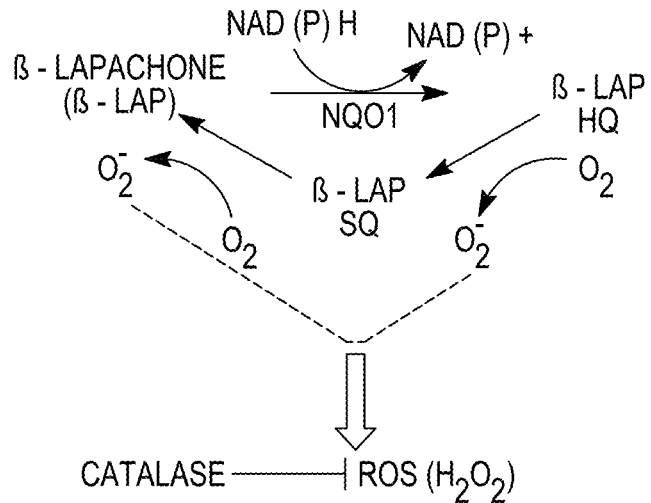
FIG. 2. NQO1:Catalase ratios in pancreatic cancer vs. normal tissue are a major determinant of efficacy for NQO1 bioactivatable drugs, ß-lap and DNQ. (A) Pancreatic cancer cells express elevated NQO1, but lower Catalase levels. Metabolism of ß-lap results in extensive $H_2O_2$ production that easily overwhelms low tumor Catalase levels. (B) In contrast, normal pancreatic tissue expresses low NQO1 and abundant Catalase levels and are, therefore, protected from NQO1 bioactivatable drugs. Patient sample enzyme assays have validated these NQO1:Catalase ratios.
Figure 2B:
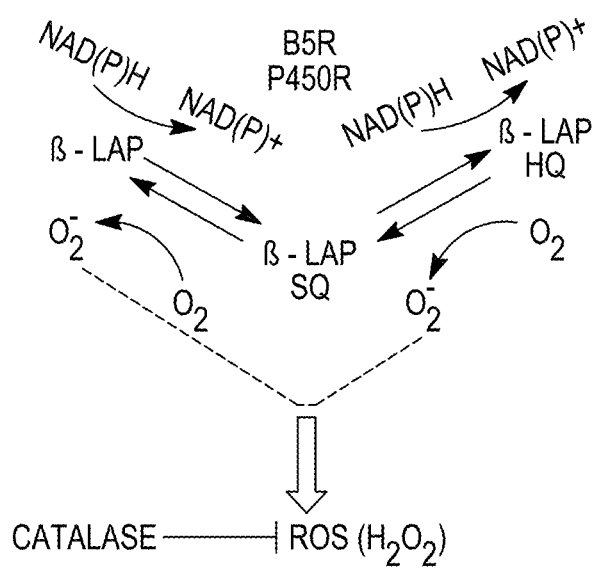
Figure 3A:
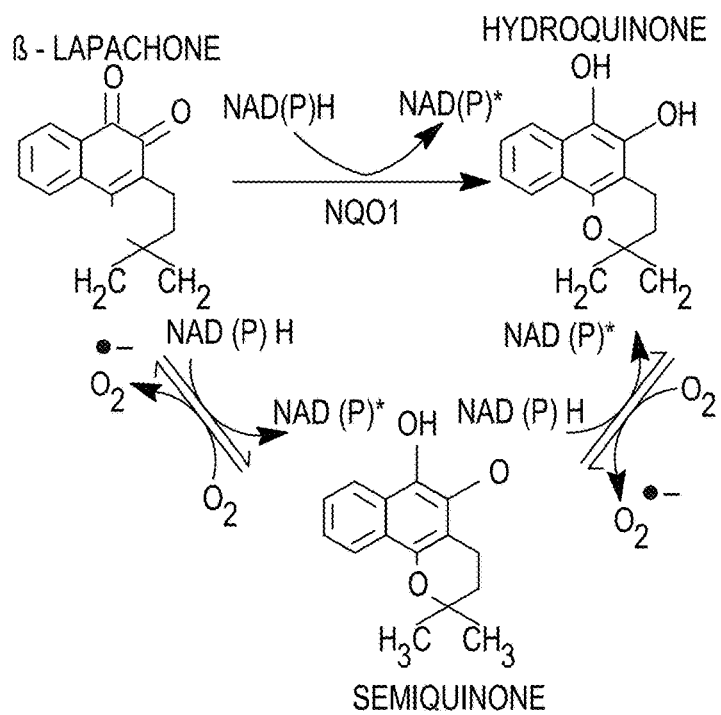
FIG. 3. Functional inhibition of NQO1 by shRNA-NQO1 knockdown protects from cell death after β-lap exposures. (A) Mechanism of β-lap redox cycling; DNQ and its derivatives can follow an analogous mechanism. (B) NQO1 protein levels and enzyme activities in Mia Paca-2 parental, knockdown (17-1, 17-3, and 17-7), and Non-Silencing (NS, Mia Paca-2 shSCR) clones. (C) Long-term relative survival assays of Mia Paca-2 parental and NQO1 knockdown cells with β-lap or β-lap plus dicumoral (DIC) for 2 hour exposures at the indicated doses. (D) Survival of NQO1 knockdown clones (17-1, 17-3, 17-7) exposed to β-lap (6 μM, 2 h) was significantly rescued by low doses of DIC (μM, 2 h) compared to doses required to rescue Mia Paca-2 NS clones (*** p<0.001). (E) β-Lap dosage for $LD_{50}$ of Mia Paca-2 knockdown clones and different pancreatic cancer cell lines (BXPC3, Capan1, ASPC1, HS766T, Capan2, and CFPAC1) ($R^2$=0.9053). (F) β-Lap lethality in various pancreatic cancer cells, with or without dicoumarol (DIC, 50 μM) or BAPTA-AM (5 μM, 1 h) treatments.
Figure 3B:
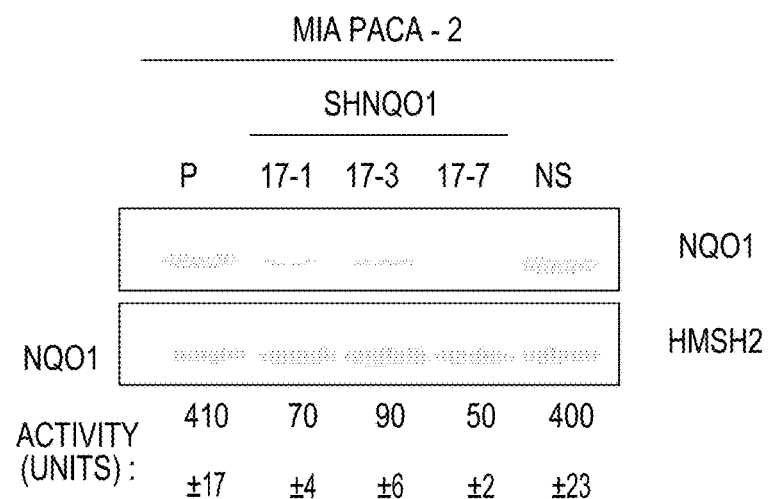
Figure 3C:
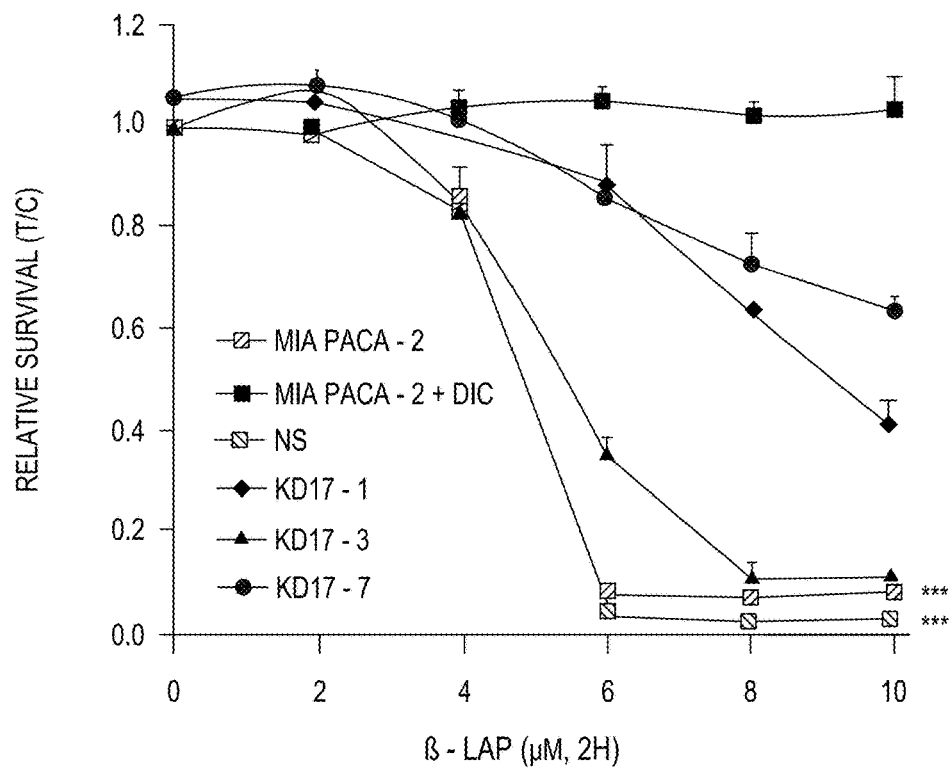
Figure 3D:
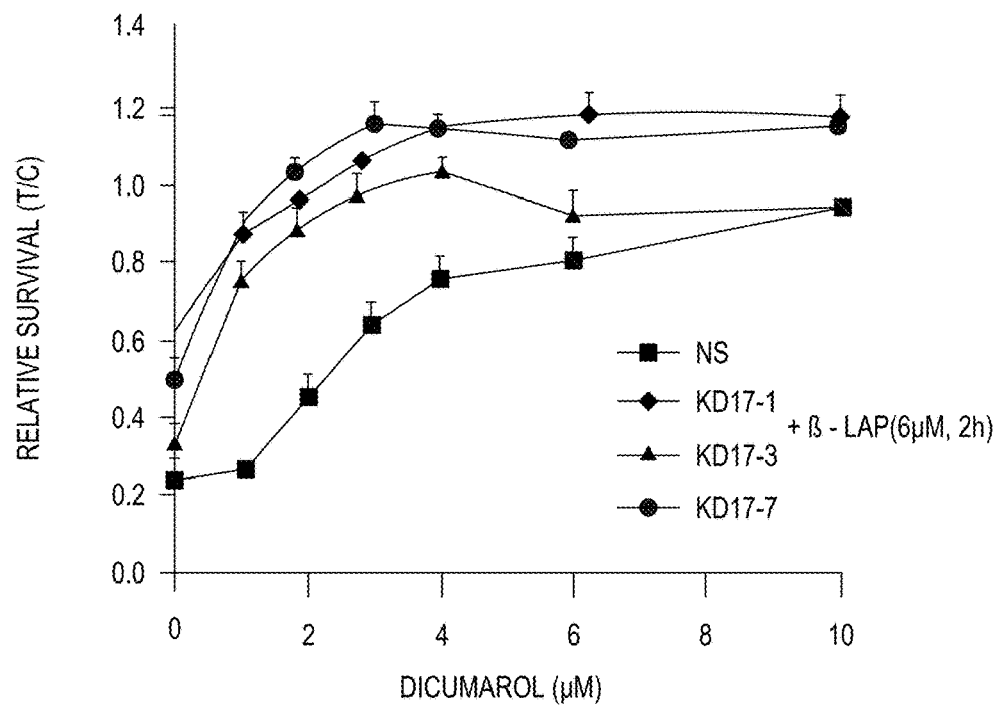
Figures 3E, 3F:
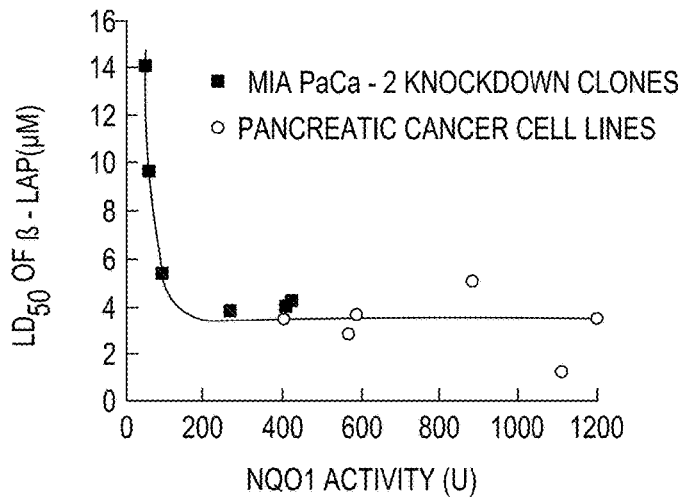

FIG. 1 shows the expression of NQO1 and Catalase in pancreatic tumor vs. associated normal tissue. Catalase is thus significantly over-expression in normal vs. tumor tissue. NQO1:Catalase ratios in pancreatic cancer vs. normal tissue are a major determinant of efficacy for NQO1 bioactivatable drugs such as ß-lap and DNQ (FIG. 2). Particularly in the presence of a high NQO1:Catalase ratio, NQO1 bioactivatable drugs kill by tumor-specific DNA damage, inducing PARP1 hyperactivation and unique programmed necrotic cell death. Tumor-specific lethality is independent of p52 status, Bax/bak loss, oncogene activation status, cell cycle status, and hypoxia.

Figure 4A:
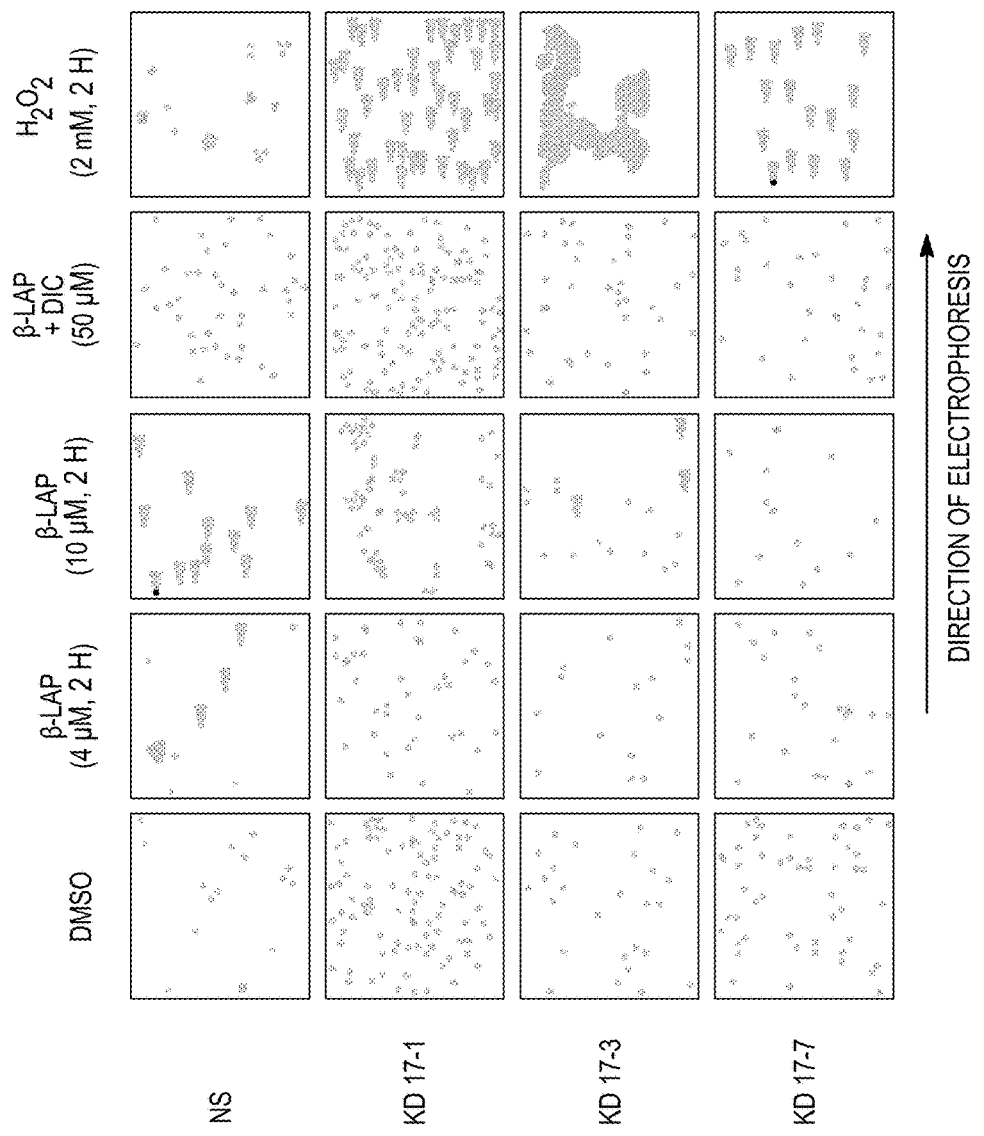
FIG. 4. β-Lap-induced DNA damage is significantly decreased by NQO1 shRNA-knockdown. (A) NS and shRNA-NQO1 knockdown Mia Paca-2 clones (17-1, 17-3, 17-7 and NS) were exposed to β-lap, +50 μM DIC and assessed for DNA damage using comet assays. Cells were also exposed to 2 mM $H_2O_2$ for 2 hours as positive controls. (B) Comet tail lengths were measured using Image J software (a.u., arbitrary unit) (***, p<0.001). (C) ß-Lap treatment causes extensive 8-oxoguanine (8-OG) base damage in Mia Paca-2 pancreatic cancer cells. Thus, ß-lap causes SSBs and extensive base damage.
Figure 5A:
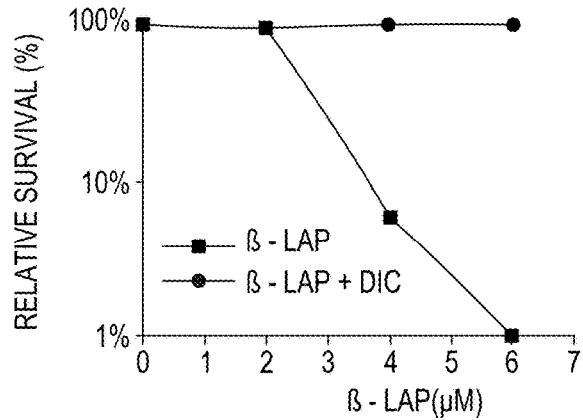
FIG. 5. Metabolic changes after β-lap or DNQ treatments. Mia Paca-2 cells were treated with β-lap (6 μM) (A), DNQ or a DNQ derivative (DNQ87) (C, D)+/−DIC (50 μM) and survival was monitored. Mia PaCa-2 cells exposed to ß-lap+/−DIC were also assessed for changes in ATP (B), glucose consumption (E) and lactate production in the media (F) at the indicated times.
Figure 5B:
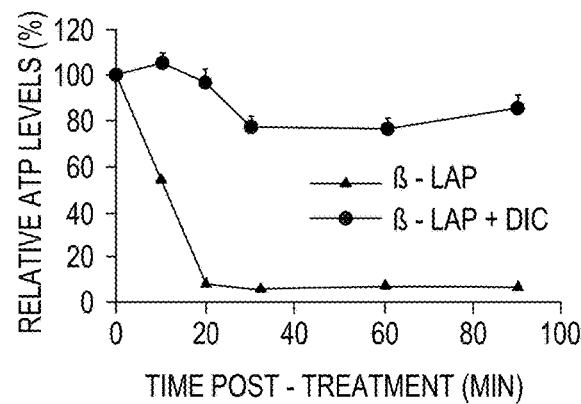
Figure 5C:
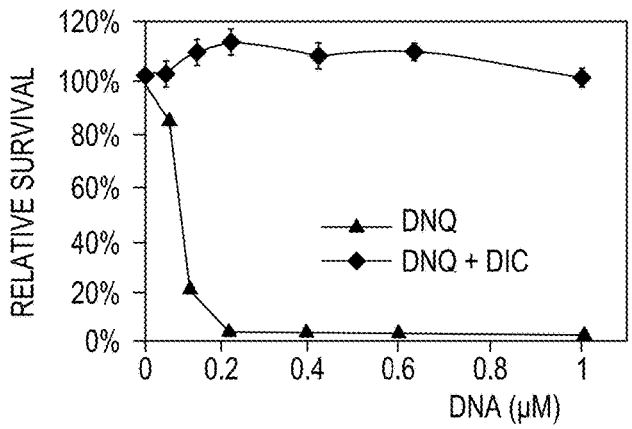
Figure 5D:
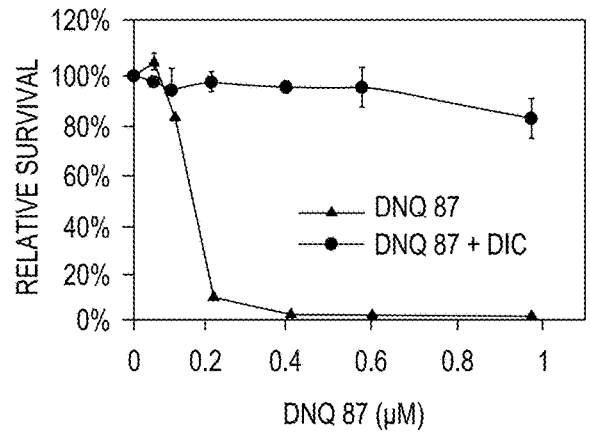
Figure 5E:
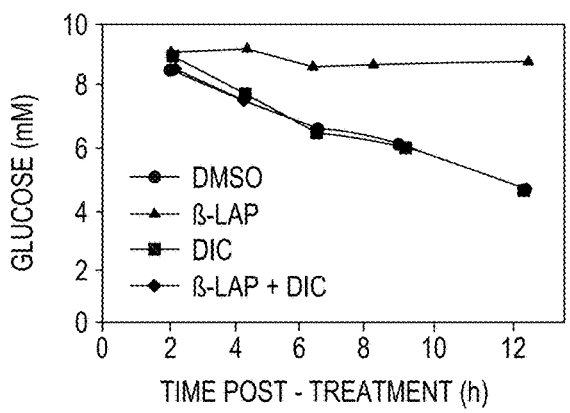
Figure 5F:
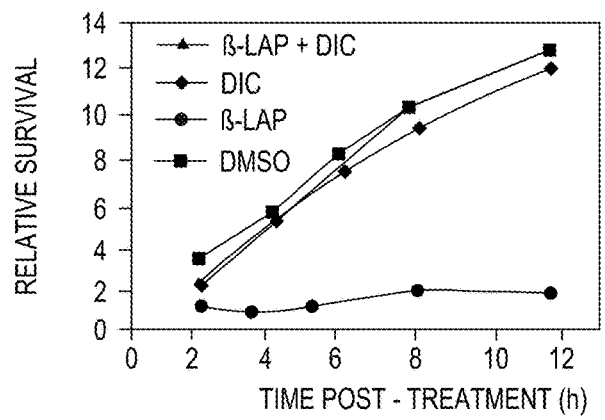

NQO1 is a principal determinant of ß-lap cytotoxicity, and functional inhibition of NQO1 by shRNA-NQO1 knockdown protects from cell death after β-lap exposures (FIG. 3). ß-Lap-induced DNA damage is NQO1-dependent, tumor-specific, and is significantly decreased by NQO1 shRNA-knockdown (FIG. 4). Also, NQO1 bioactivatable drugs cause dramatic suppression of glycolysis and loss of ATP that can inhibit DNA repair (FIG. 5).

Figure 6A:
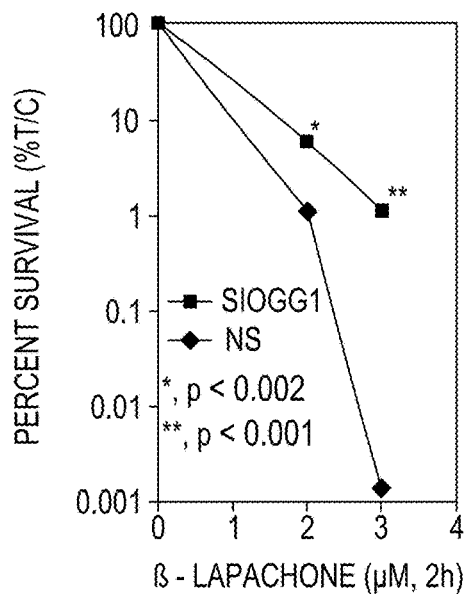
FIG. 6. siRNA-mediated knockdown of the Ogg1 glycosylase renders ß-lap-treated pancreatic cancer cells resistant to ß-lapachone. Two separate experiments are shown. Mia-Paca2 pancreatic cancer cells were exposed to siRNA-scrambled (NS) or siRNA-specific for Ogg1 (siOGG1) for 24 hours, then cells were treated with ß-lapachone for 2 hours at the indicated doses. Survival, measured by colony forming ability assays were then performed and graphed with ß-lapachone doses used, as illustrated in (A) and (B).
Figure 6B:
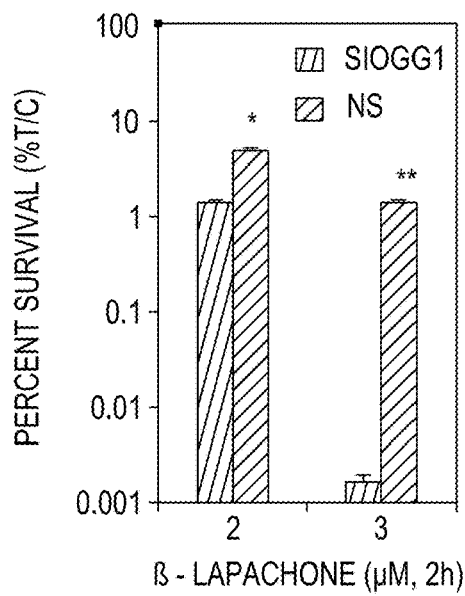
Figure 7:
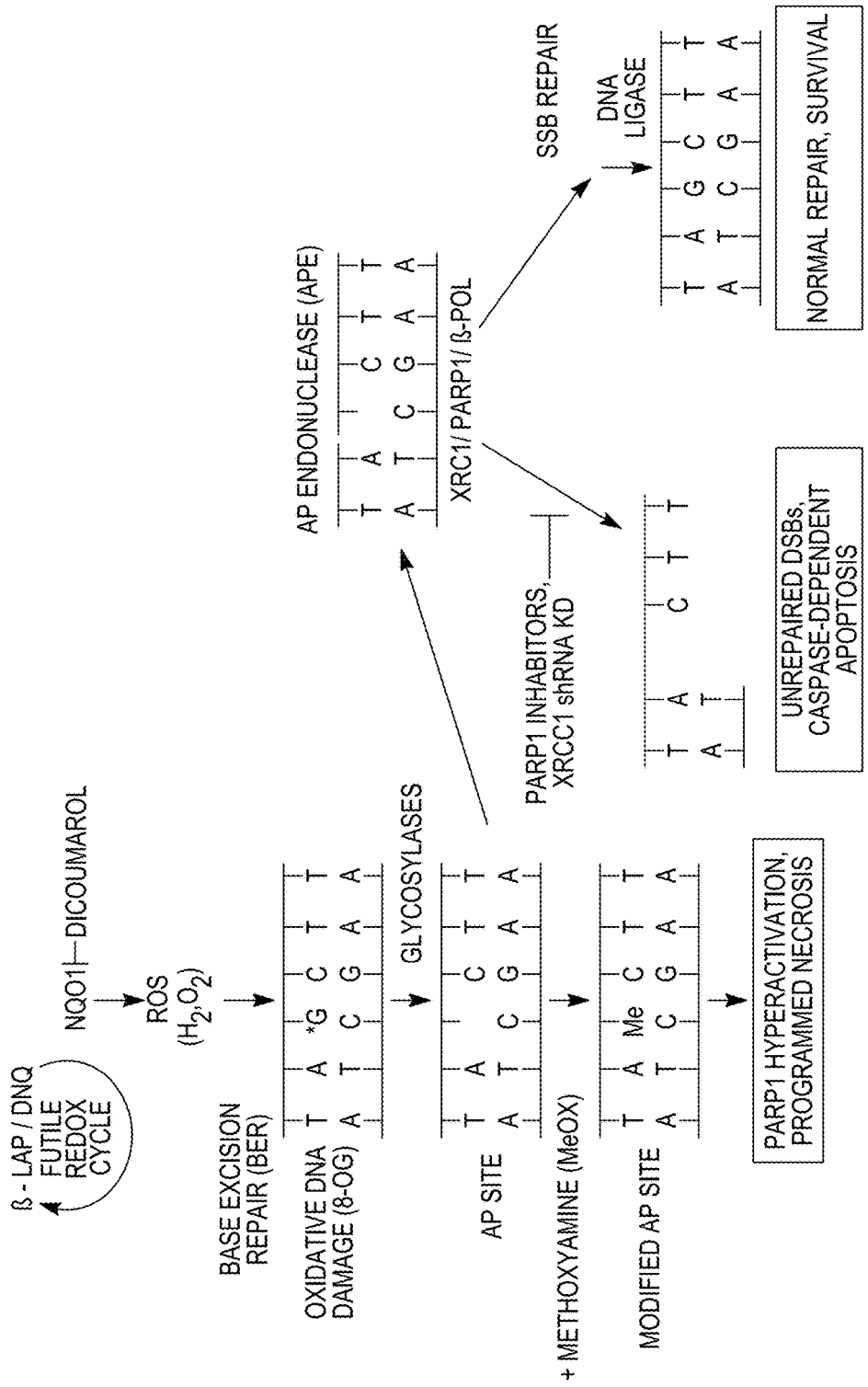
FIG. 7. NQO1 bioactivatable drugs cause SSBs and base lesions in a tumor-specific manner, thus they can be used to make DNA repair inhibitors tumor-selective.
Figure 8A:
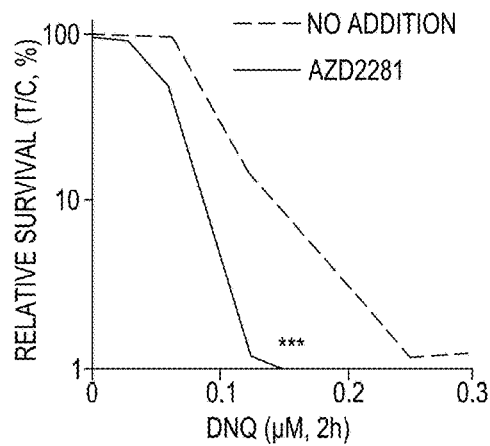
FIG. 8. PARP1 inhibitors synergize with NQO1 bioactivatable drugs. (A-D) Mia Paca-2 cells were pre-incubated with various PARP1 inhibitors (10 μM) then with deoxynyboquinone (DNQ), as indicated, for 2 hours with inhibitors. (E-H) AG014699 enhances ß-lap. Relative survival was then assessed using a 7-day DNA assay (Huang et al., *Cancer Res.*, 2012, 72(12), 3038-3047) (***, p<0.001).
Figure 8B:
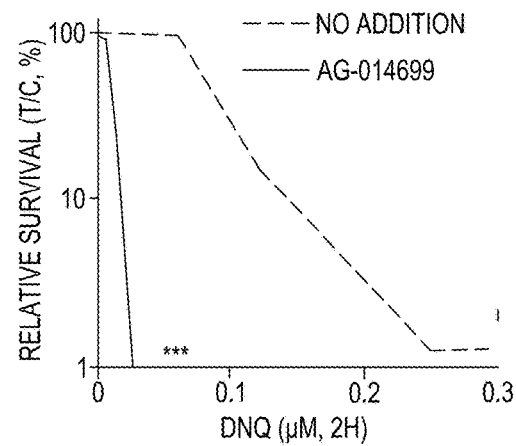
Figure 8C:
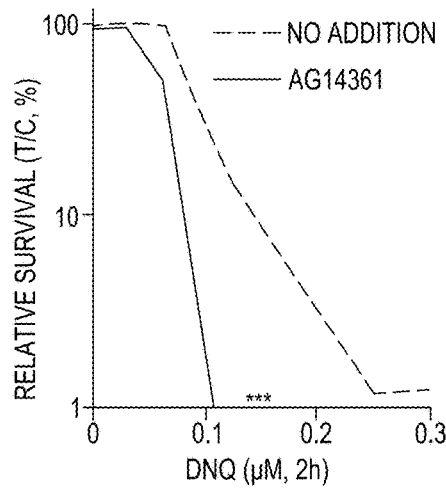
Figure 8D:
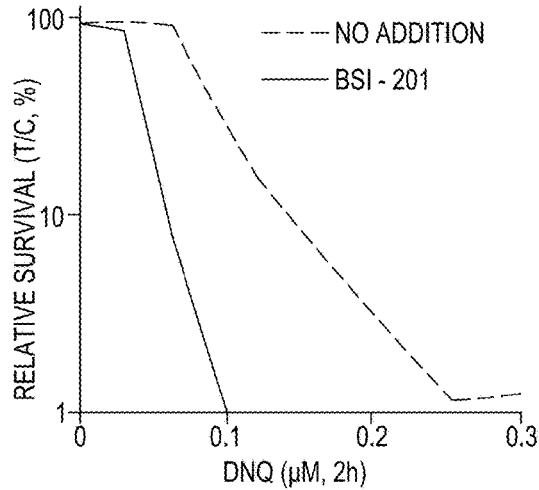
Figure 8E:
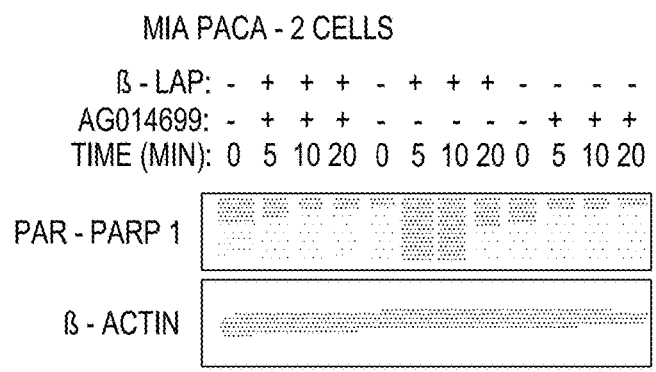
Figure 8F:
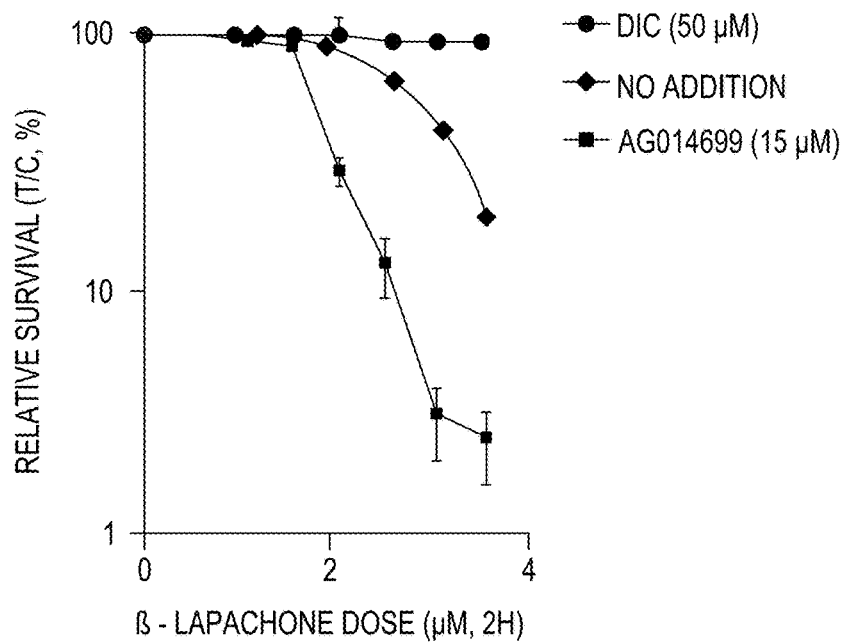
Figure 8G:
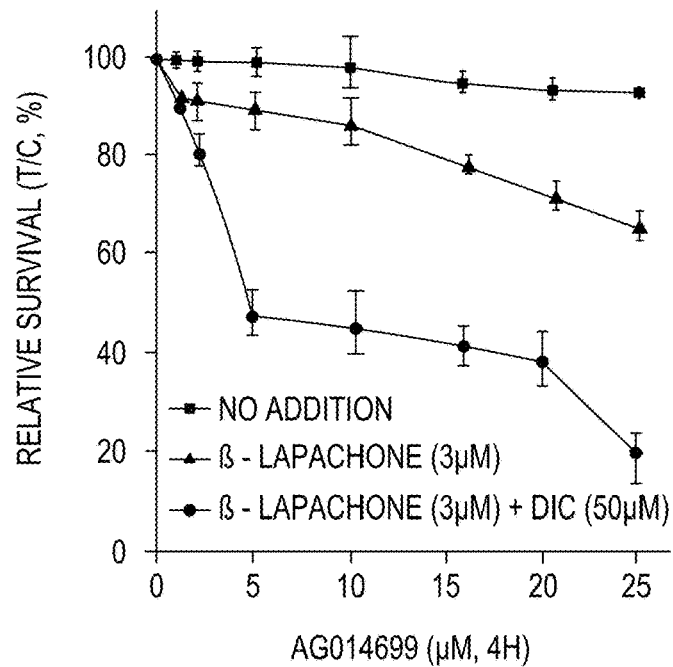
Figure 8H:
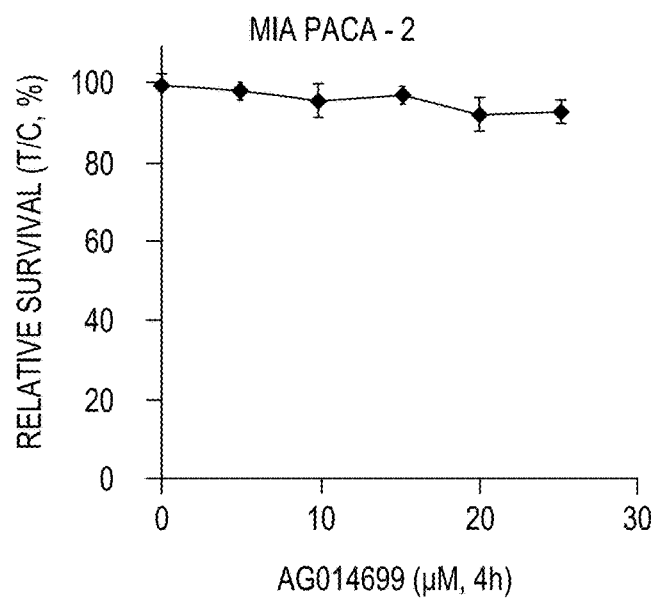
Figure 9A:
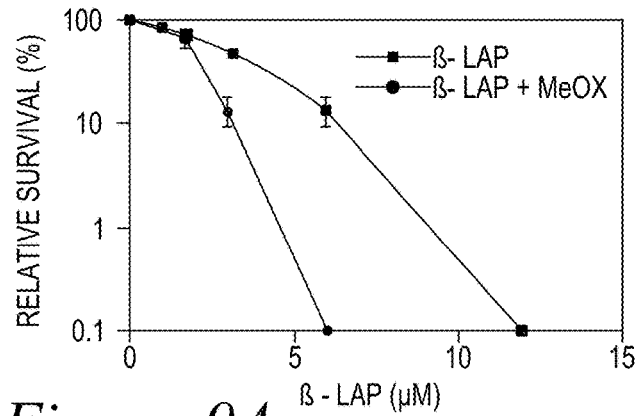
FIG. 9. Methoxyamine (MeOX) enhances β-lap-induced NQO1-driven lethality. Mia Paca-2 cells were treated with indicated doses of β-lap+/−MeOX (12 mM), or β-lap alone for 2 hours. Endpoints examined: (A) Colony forming assays show synergy of MeOX+ß-lap; (B) MeOX treatment modifies AP sites induced by β-lap in Mia Paca-2 cells; (C) MeOX enhances β-lap-induced ATP loss; (D) MeOX blocks ATP recovery after sublethal β-lap doses; (E) β-lap+MeOX co-treatment enhances γH2AX foci formation. MeOX+a sublethal β-lap dose (2 μM) was equivalent to a lethal β-lap dose (6 μM); and (F) MeOX (6 mM)+β-lap (2 μM) induced significantly greater apoptosis (TUNEL+ cells) in an NQO1-dependent manner than β-lap (4 μM) alone. Dicoumarol (DIC, 50 μM, 2 h) blocked synergy.
Figure 9B:
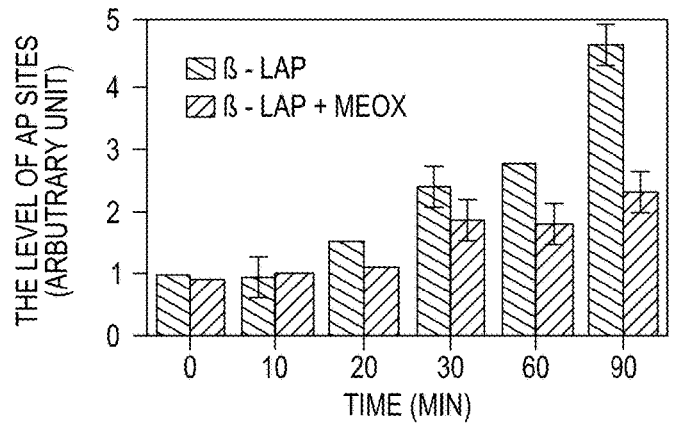
Figure 9C:
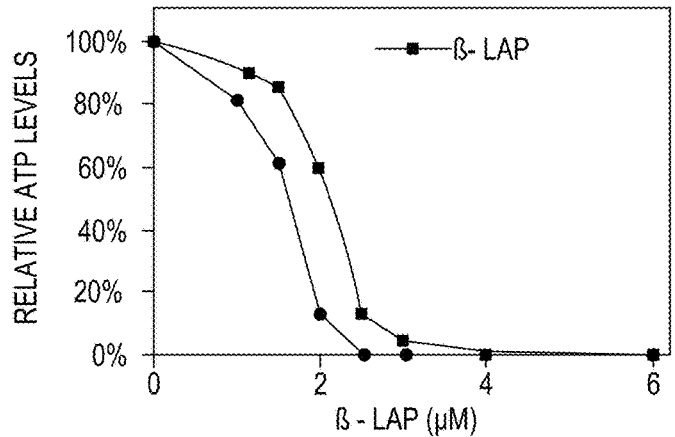
Figure 9D:
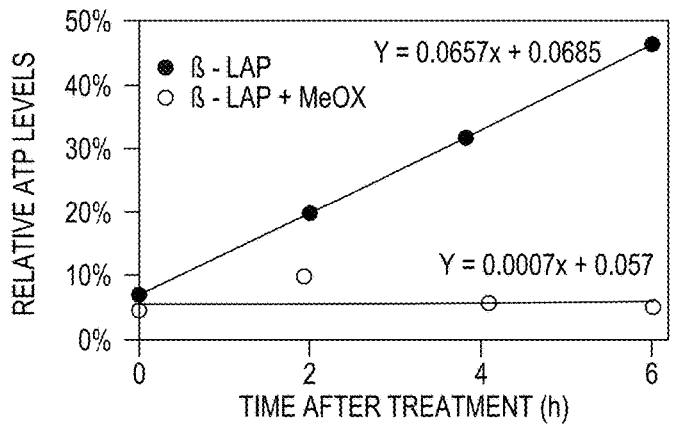
Figure 9E:
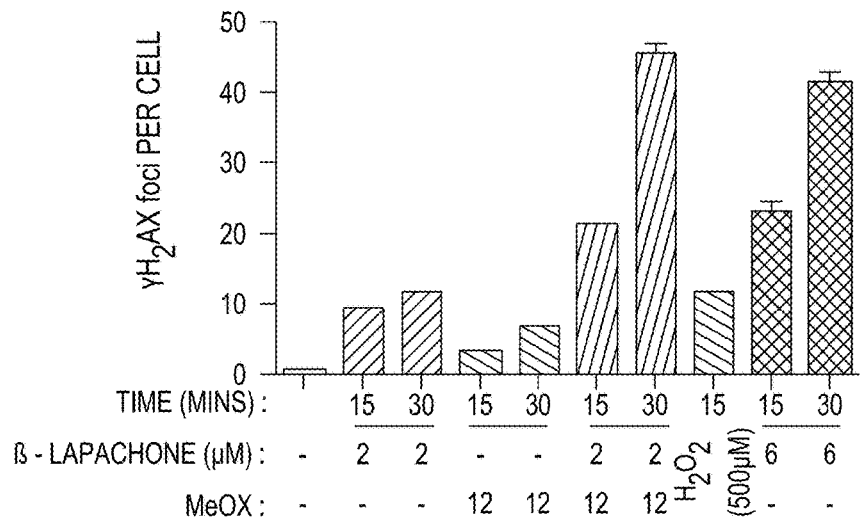
Figure 9F:
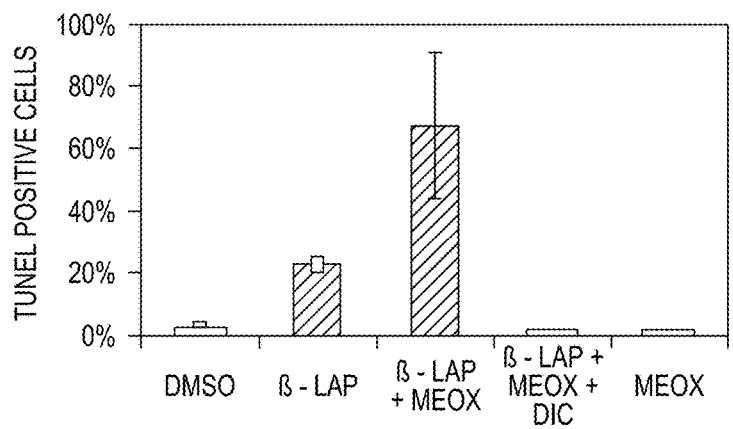
Figure 10A:
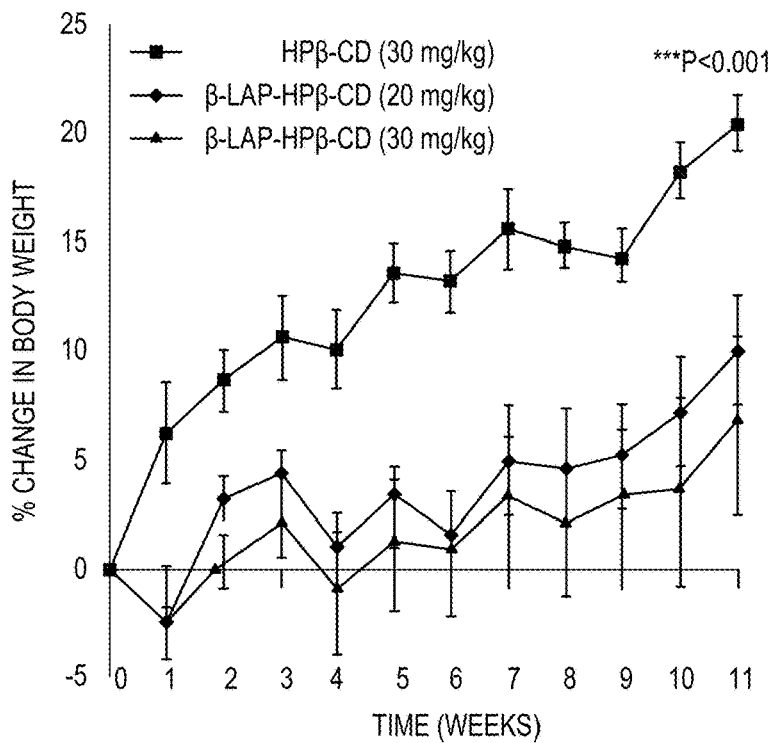
FIG. 10. β-Lapachone has significant antitumor efficacy against MIA PaCa-2 tumor xenografts. (A) Body weight changes of mice bearing orthotopic MIA PaCa-2 tumors. (B) Kaplan-Meier survival for pancreatic antitumor efficacy experiments described in (A). Log-rank analyses were performed comparing survival curves (*p<0.0001) for HPβ-CD vs. β-lap-HPβ-CD at 20 or 30 mg/kg, iv. Results are combined survival data from three similar experiments. (C) Bioluminescent images (BLI) of mice bearing spleen-implanted pancreas cancers before and after treatment with HPβ-CD or β-lap-HPβ-CD (Arq761) at 20 or 30 mg/kg, iv. (D) Quantification of pancreatic tumor burden. BLI (photons per second) were determined before and 12 days post-therapy with HPβ-CD or β-lap-HPβ-CD at 20 or 30 mg/kg, iv. Results are means, +SE (n=5). Student's t tests (*p<0.005) were performed comparing HPβ-CD vs. β-lap-HPβ-CD at 20 or 30 mg/kg, iv. V, Vehicle (HPβ-CD).
Figure 10B:
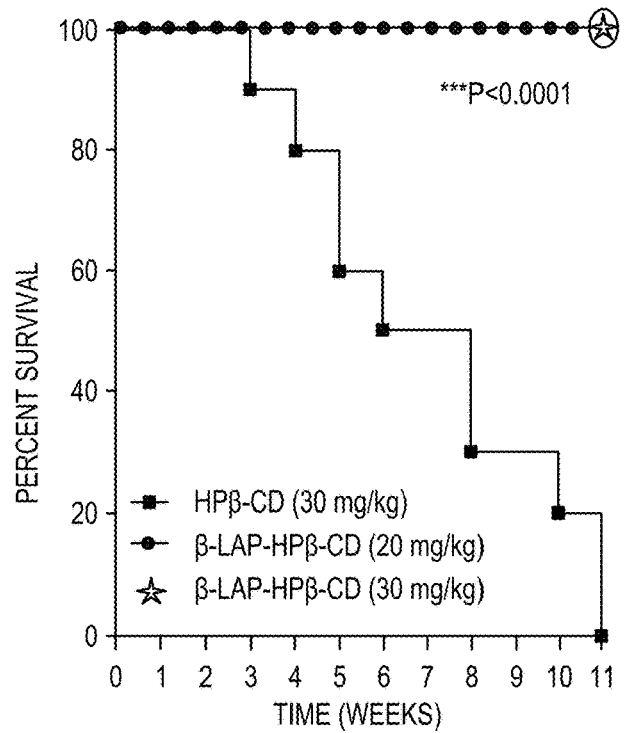
Figure 10C:
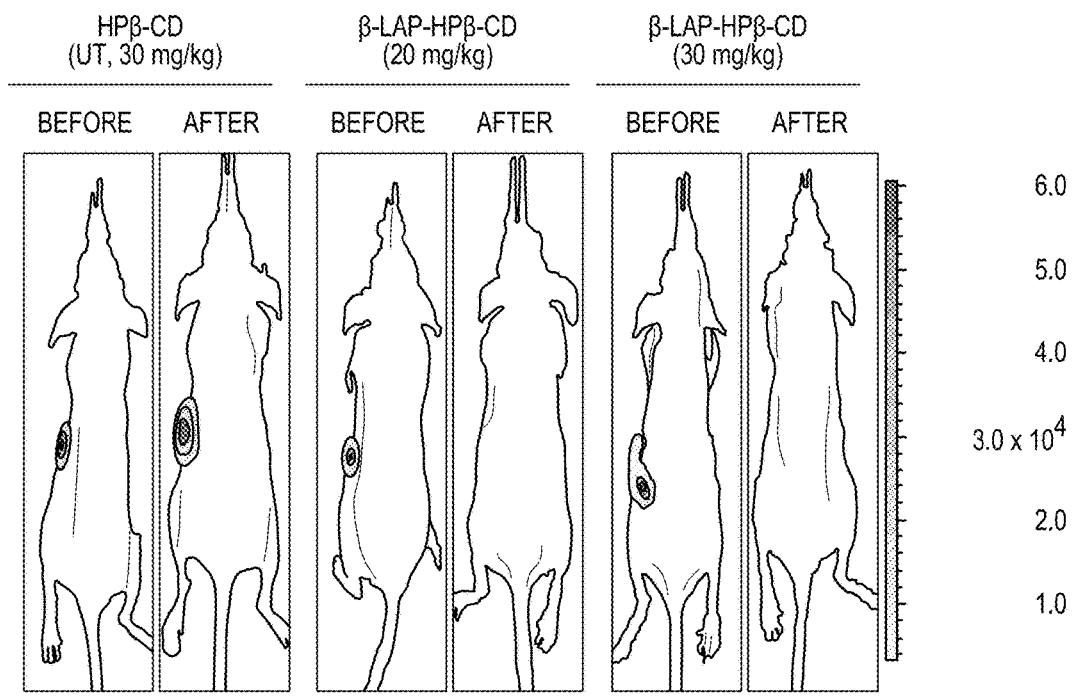
Figure 10D:
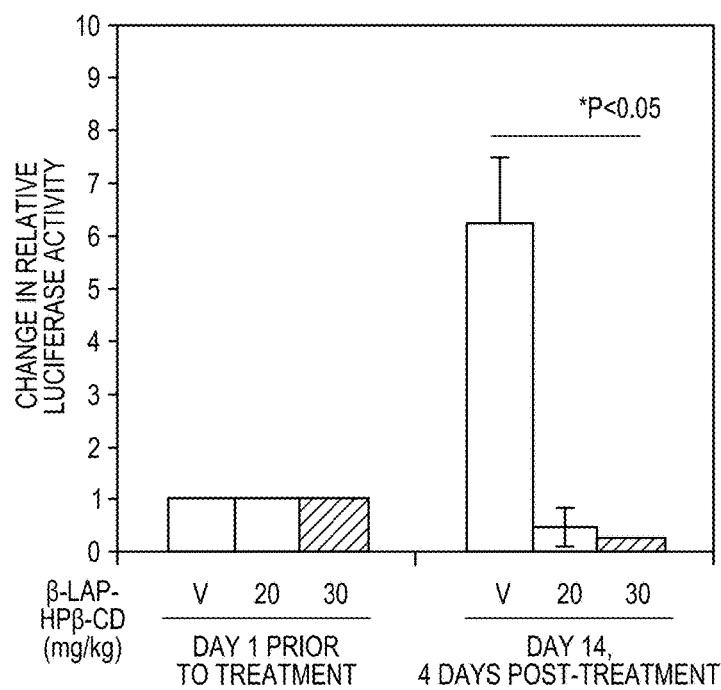

Altering BER or SSB repair can enhance NQO1 bioactivatable drug efficacy in a tumor-selective manner. siRNA-mediated knockdown of the Ogg1 glycosylase renders ß-lap-treated pancreatic cancer cells resistant to ß-lapachone (FIG. 6), however NQO1 bioactivatable drugs cause SSBs and base lesions in a tumor-specific manner, thus they can be used to make DNA repair inhibitors tumor-selective (FIG. 7). PARP1 inhibitors synergize with NQO1 bioactivatable drugs for enhanced efficacy in NQO1+ cancer cells, such as pancreatic cancer cells (FIG. 8). Also, NQO1 bioactivatable lethality is enhanced by MeOX, with accompanying metabolic effects (FIG. 9). Furthermore, β-Lapachone has significant antitumor efficacy against MIA PaCa-2 tumor xenografts, as illustrated by the preclinical study data shown in FIG. 10.

Accordingly, this examples and its supporting data show that NQO1 bioactivatable drugs induce DNA base damage and single strand DNA breaks, and that inhibiting Base Excision Repair (BER) enhances ß-lap-mediated pancreas cancer-selective lethality. Additionally, inhibiting PARP1 activity enhances ß-lap efficacy against NQO1+ pancreas cancers. Finally, use of NQO1 bioactivatable drugs, such as compounds of the formulas of FIG. 11 and the specific compounds of FIG. 12, provides for tumor-selective use of DNA repair inhibitors, and NQO1 bioactivatable drugs cause dramatic effects such as the suppression of glucose metabolism.

Example 2. DNQ Compound and β-Lapachone Data and Therapy

IB-DNQ (DNQ-87; FIG. 12) works at much lower doses versus ß-lapachone and at doses equivalent to the parental DNQ compound. As shown in FIG. 13, it is effective against breast cancer cells in an NQO1-dependent manner, as well as triple-negative breast cancer cells. Unlike ß-lapachone (ß-lap), efficacy of DNQ87 increases in an NQO1-dependent manner and the therapeutic window is larger (FIG. 14). As shown in FIG. 15, DNQ87 causes cell death that can be blocked by dicoumarol, catalase, and BAPTA-AM (a calcium chelator) (A), in descending order and consistent with the proposed pathway of cell death caused by NQO1 bioactivatable drugs (B). (C) PARP1 hyperactivation caused by DNQ87 exposure measured by PAR-PARP1 formation, highlighted by μ-calpain-mediated p53 cleavage (C) and atypical cleavage of PARP1 to ~60 kDa proteolytic fragments during cell death (D). DNQ87 also causes DNA lesions (DNA double strand breaks) in a delayed manner, monitored by gamma-H2AX, phosphorylation of ATM at ser1981, and phosphorylation of DNA-PKcs at site Thr1892 (FIG. 16). These data also indicate that DSB repair inhibitors could also be used to enhance DNQ87 lethality. Importantly alkaline elution shows extensive DNA base lesions and DNA single strand breaks, whereas the same cells assessed by neutral comet assays shows no DNA lesions.

Figure 17:
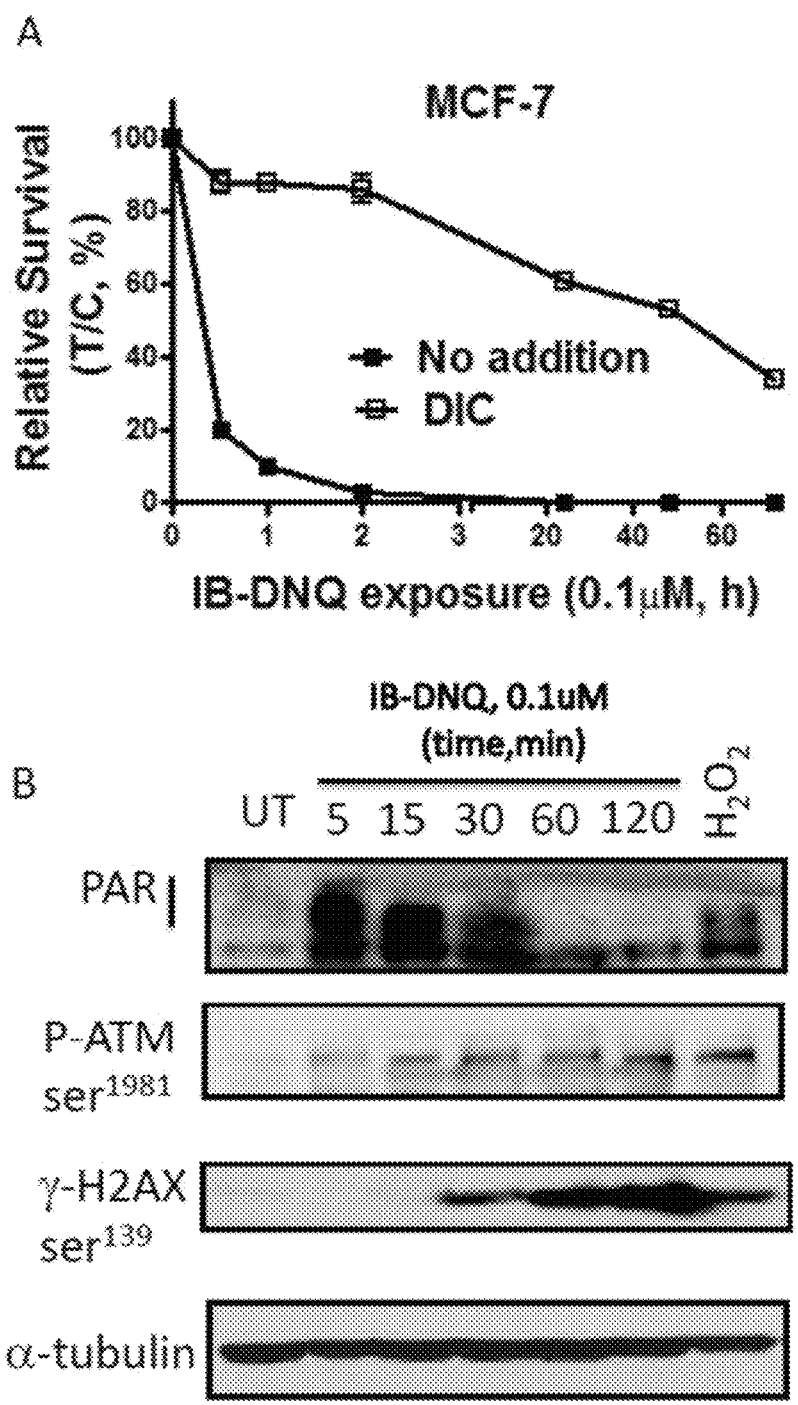
FIG. 17. SSB-PARP1-DSB Temporal Sequence. MCF-7 breast cancer cells were exposed to DNQ87 (IB-DNQ), with or without dicoumarol (DIC, 50 μM) and survival (A) or temporal sequence of PAR-PARP1 (PAR) formation, as well as phosphorylations if H2AX (g-H2AX), ATM were monitored at specific sites indicated and monitored using alpha-tubulin levels for loading.
Figure 18:
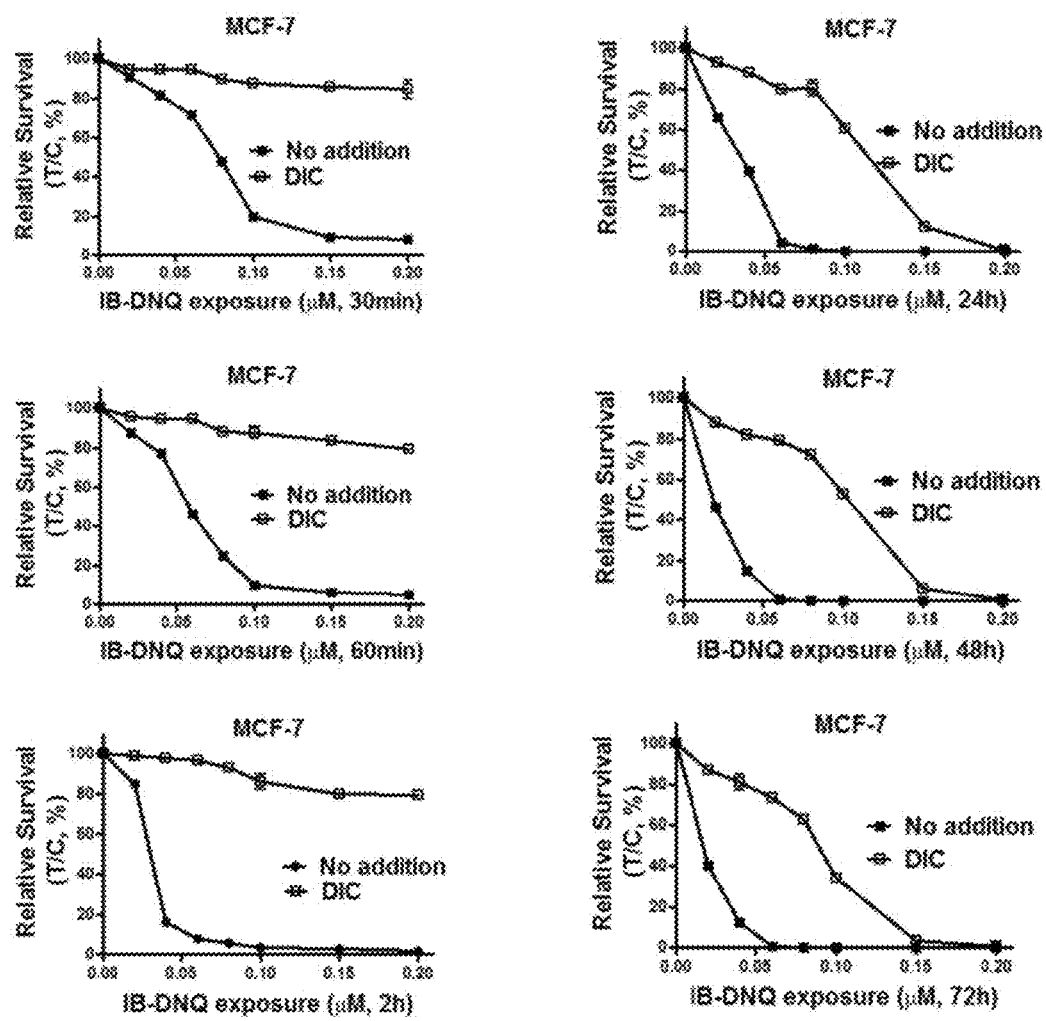
FIG. 18. The therapeutic window of DNQ87 using dicoumarol to mimic low levels of NQO1 in normal tissue compared to using dicoumarol to mimic normal tissue in NQO1 overexpressing MCF-7 human breast cancer cells (at time points 30 minutes, 60 minutes, 2 hours, 24 hours, 48 hours, and 72 hours).
Figure 19:
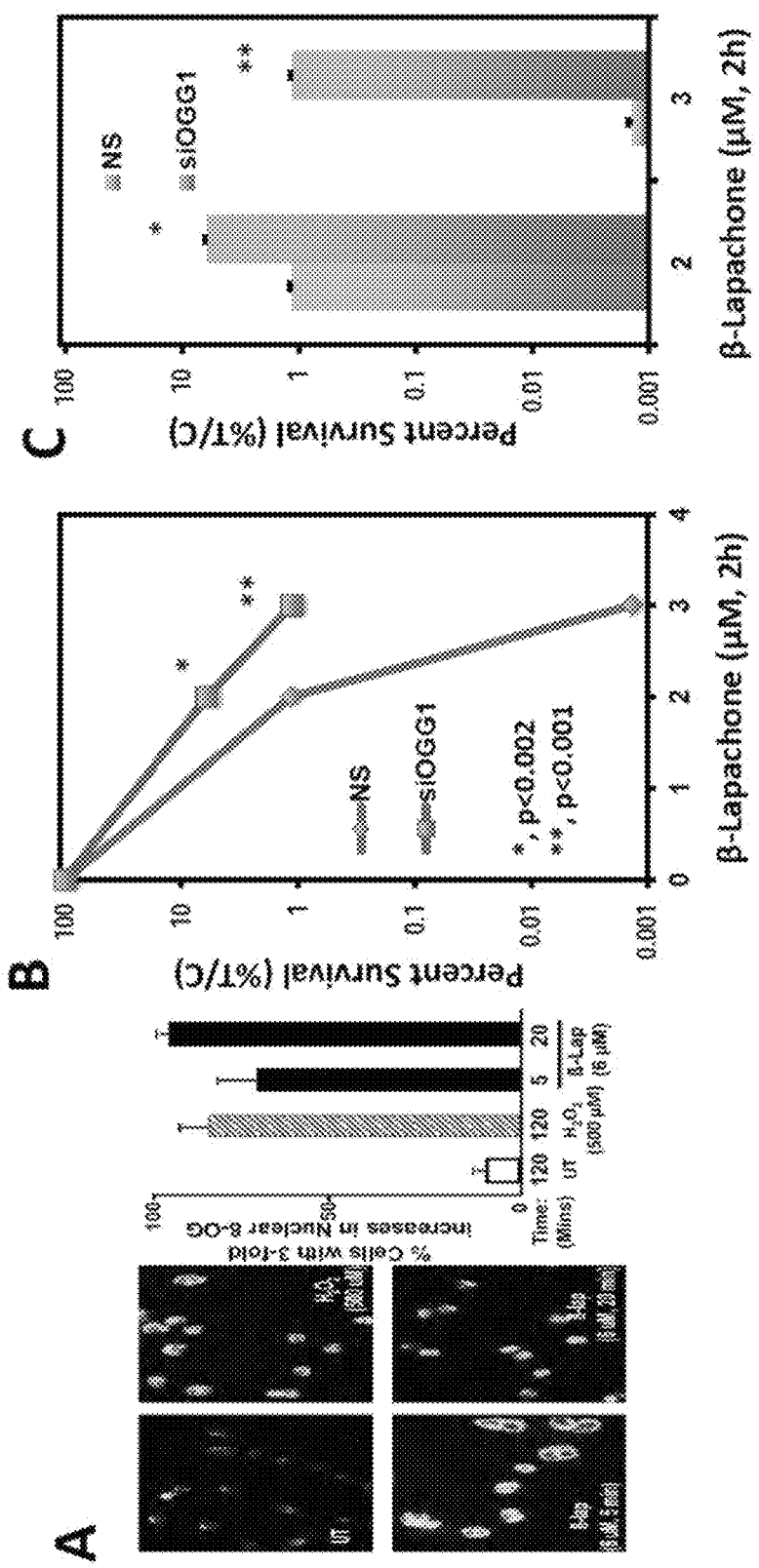
FIG. 19. Exposure to NQO1 bioactivatable drugs causes extensive 8-oxoguanine levels. A) R-lapachone exposure causes extensive formation of 8-oxoguanine. B,C) Two separate experiments are shown. Mia-Paca2 pancreatic cancer cells were exposed to siRNA-scrambled (NS) or siRNA-specific for Ogg1 (siOGG1) for 24 hours, then cells were treated with ß-lapachone for 2 hours at the indicated doses. Survival, measured by colony forming ability assays were then performed and graphed with ß-lapachone doses used.

DSB formation, monitored by P-ATM and P-H2AX are delayed in NQO1 overexpressing human breast cancer cells, and only occur after PARP1 hyperactivation. IB-DNQ (DNQ-87; FIG. 12) causes massive $H_2O_2$ formation leading to DNA base and single strand breaks that are quickly recognized by PARP1, which protects the DNA and stimulates base excision and DNA single strand break repair. Only when PARP1 is exhausted through its hyperactivation are DNA double strand breaks noted (see FIG. 17). FIG. 18 shows the therapeutic window of DNQ87 using dicoumarol to mimic normal tissue in NQO1 overexpressing MCF-7 human breast cancer cells. As illustrated by FIG. 19, exposure to NQO1 bioactivatable drugs causes extensive 8-oxoguanine levels, levels equivalent to 500 μM $H_2O_2$ exposures. Knockdown of the glycosylase, Ogg1, which preferentially detects 8-oxo-guanine (8-OG), results in dramatic resistance to NQO1 bioactivatable drugs, such as ß-lapachone. A) ß-lapachone exposure causes extensive formation of 8-oxoguanine. B,C) Two separate experiments are shown. Mia-Paca2 pancreatic cancer cells were exposed to siRNA-scrambled or siRNA-specific for Ogg1 for 24 hours, then cells were treated with ß-lapachone for 2 hours at the indicated doses. Survival, measured by colony forming ability assays were then performed and graphed with ß-lapachone doses used.

NQO1 expressing cells create high levels of $H_2O_2$ that are not scavenged by catalase, due to its lowered levels in cancer cells. In contrast, normal tissues have low NQO1 levels and if $H_2O_2$ is created by exposure to the drug, elevated levels of Catalase scavenges the obligate ROS for this agent. Normal tissues are therefore protected (see FIG. 2). Knowledge of DNA damage created by DNQ, ß-lapachone or their respective analogs allows new and non-obvious strategies for enhanced lethality. Conversely, DNA repair inhibitors fail commonly because they lack tumor-selectively. The NQO1-dependent DNA lesions created exclusively in specific solid tumors, results in specific DNA base damage (e.g., 8-oxyguanine), which through futile DNA repair processes results in PARP1 hyperactivation. Knowledge of this damage results in two separate strategies to enhance the tumor-specific lethalities of NQO1 bioactivatable drugs: (A) using DNA apurinic/apyrimidinic (AP site) modifying agents, such as methoxyamine (MeOX), which is currently in clinical trials; and (B) use of PARP1 inhibitors, which prevents its hyperactivation, but also prevents repair of DNA single strand and then DNA double strand breaks caused by futile BER repair and DNA replication in cancer cells. Since we previously have obtained data showing that PARP1 hyperactivation is required for lethality by NQO1 bioactivatable drugs, inhibiting PARP1 activity to achieve synergy is a surprising result. Cells die by enhanced PARP1 hyperactivation and programmed cell death by the mechanism in (A) using MeOX, while cells die by normal apoptosis in the strategy outlined in B using PARP1 inhibitors (see FIG. 7).

Figure 20:
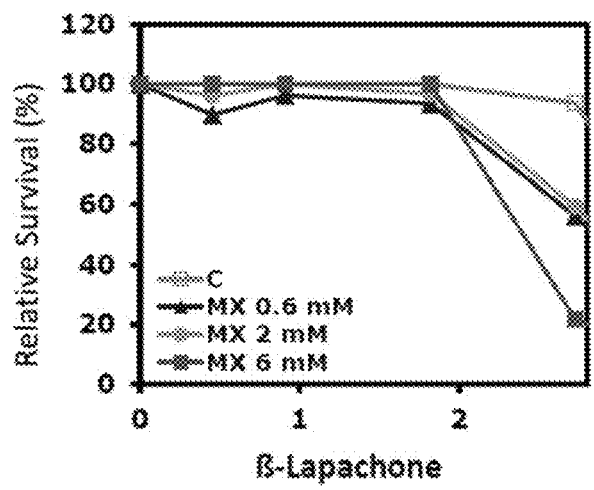
FIG. 20. Determination of lethal vs. sublethal doses of methoxyamine (MeOX or MX, as indicated); A, MeOX with β-lapachone; B, MeOX; C, MeOX.
Figure 20:
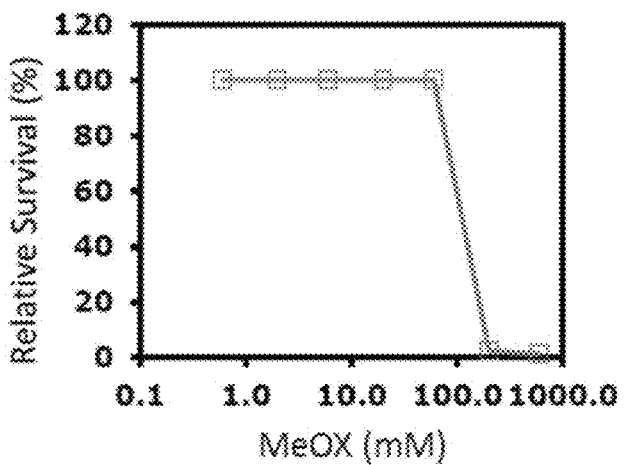
Figure 20:
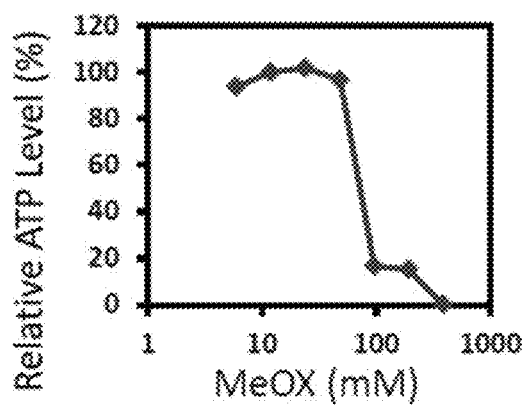
Figure 21A:
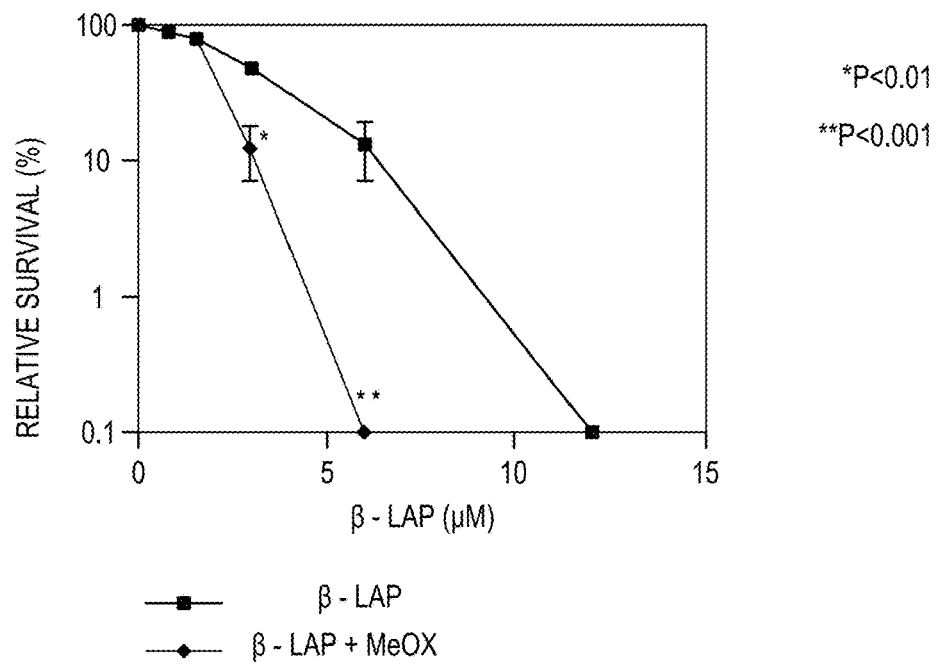
FIG. 21. Inhibition of BER mediated by Methoxyamine (MeOX) (A, B) or by XRCC1 shRNA knockdown (C) enhances the lethal effects of β-lap as measured using colony forming ability assays; (D), surviving fraction shown.
Figure 21B:
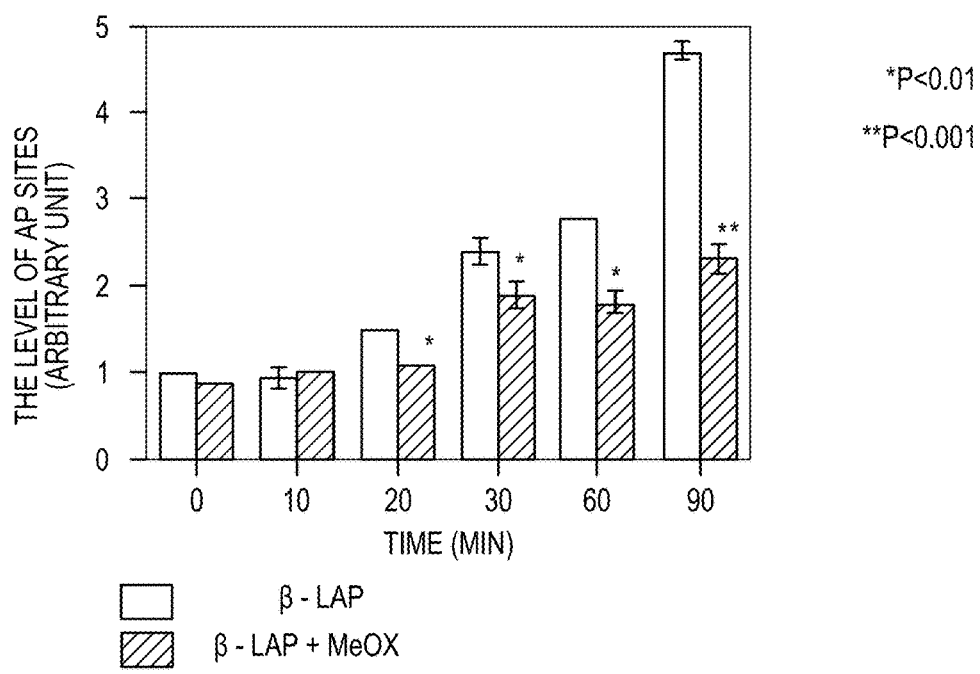
Figure 21C:
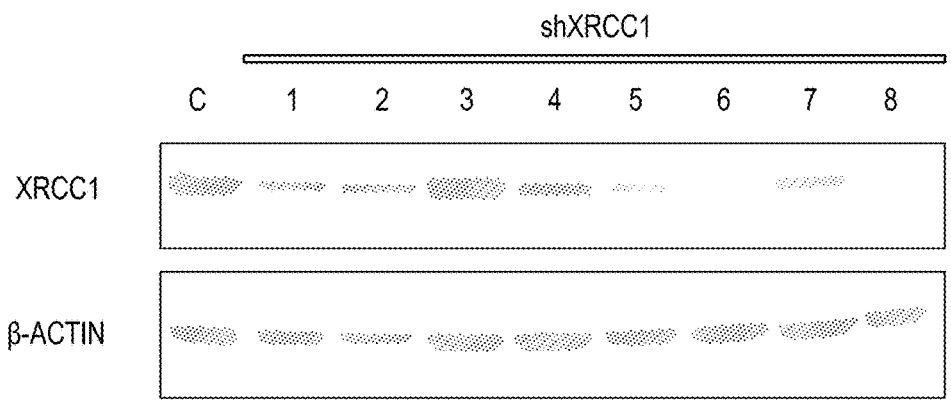
Figure 21D:
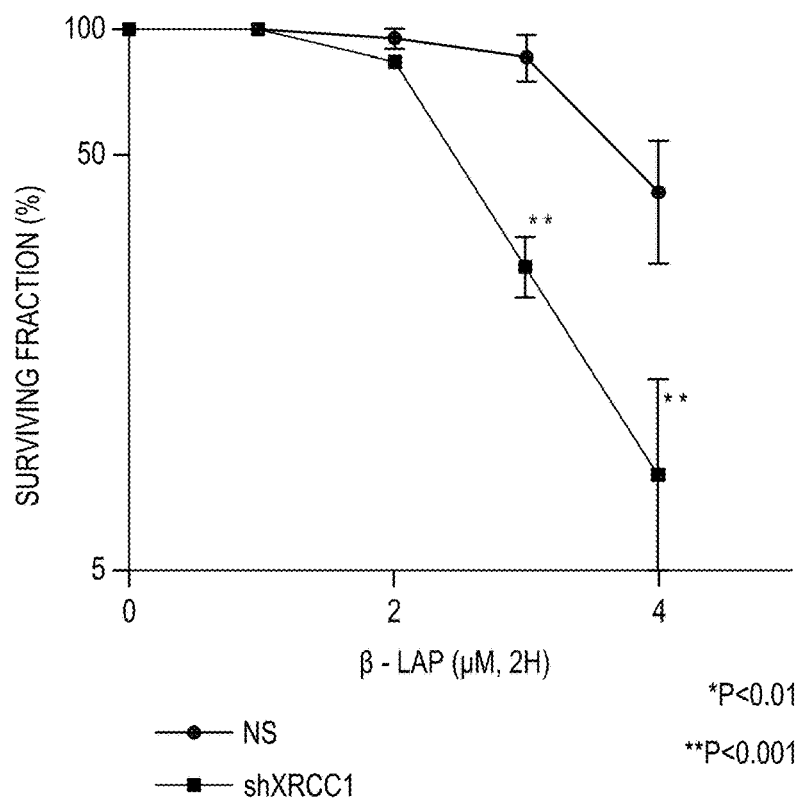

As shown in FIG. 20, methoxyamine enhances ß-lapachone-induced lethality. A, Addition of nonlethal doses of methoxyamine (MX or MeOX) to cells exposed to ß-lapachone results in synergistic lethality of Mia Paca2 pancreatic cancer cells. B and C, Methoxyamine (MeOX) is an AP-site modifying chemical that is nontoxic to >100 mM as measured by relative survival and ATP loss. Optimal concentrations in combination with NQO1 bioactivatable drugs are between 6-12 mM. FIG. 21 illustrates Proof of Principle studies. A. Methoxyamine (MeOX) augments ß-lapachone (ß-lap)-induced lethality in MiaPaca2 pancreatic cancer cells. B. Addition of MeOX modifies AP sites and therefore decreases signal of AP site formation in ß-lap+MeOX exposed cells. MeOX dose was 12 mM, ß-lap Dose was 6 µM. C,D. XRCC1 is a scaffolding protein that enables base excision repair (BER). Elimination of XRCC1 causes elevated AP sites and DNA single strand breaks, at which PARP1 can bind and become activated/hyperactivated. Knockdown of XRCC1 (C) enhances the lethality of ß-lapachone treatment.

Figure 22A:
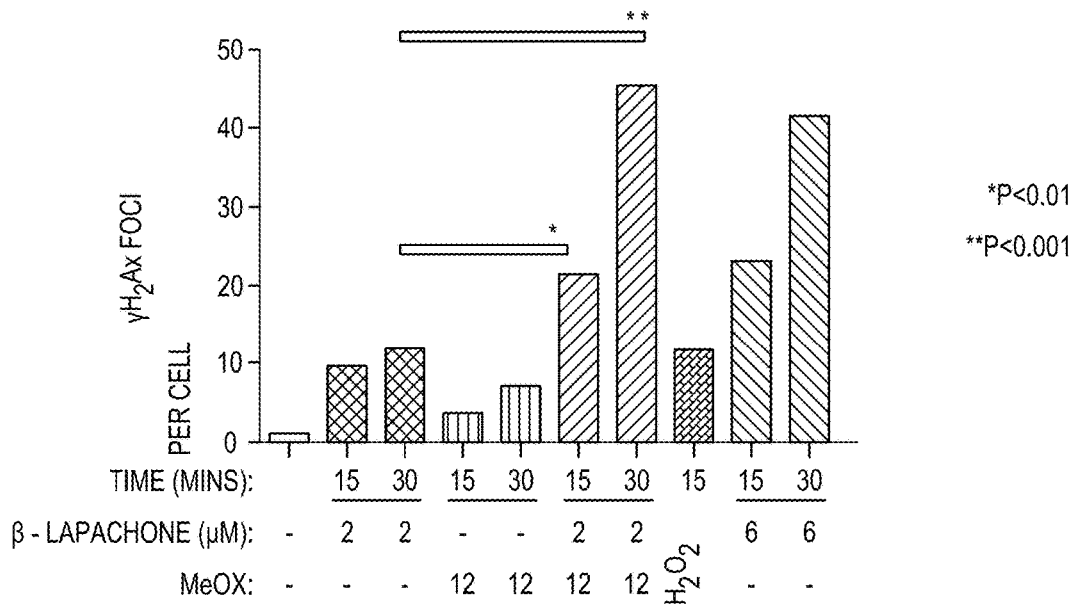
FIG. 22. Combined treatment of BER inhibitors and β-lap increases DNA damage (A) and cell death monitored by TUNEL assays (B), consistent with programmed necrosis.
Figure 22B:
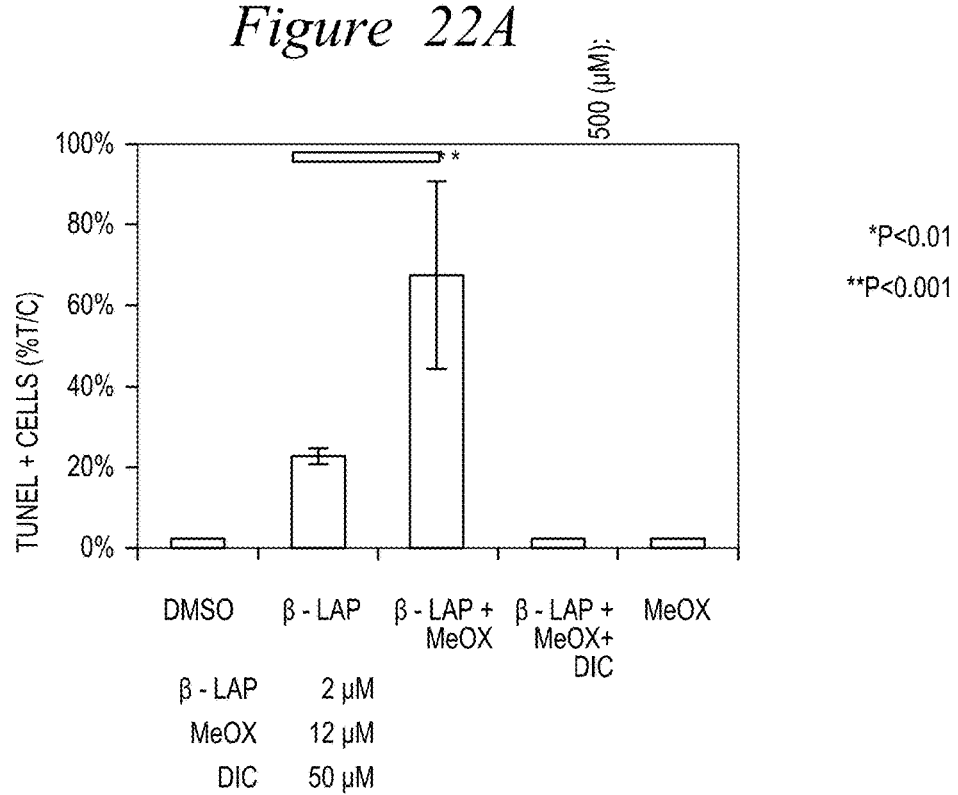
Figure 23A:
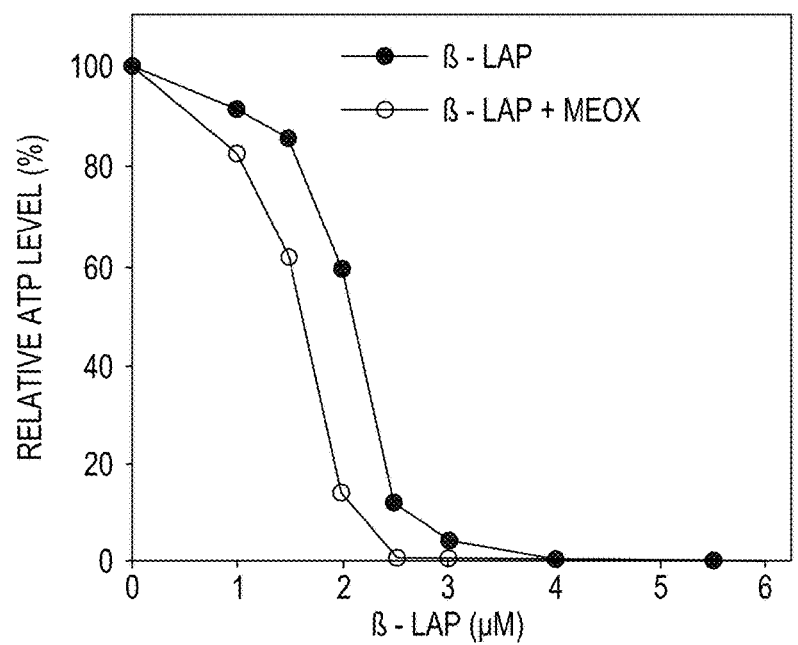
FIG. 23. Inhibition of BER pathway enhances β-lap induced ATP loss and represses its recovery (A-D).
Figure 23A:
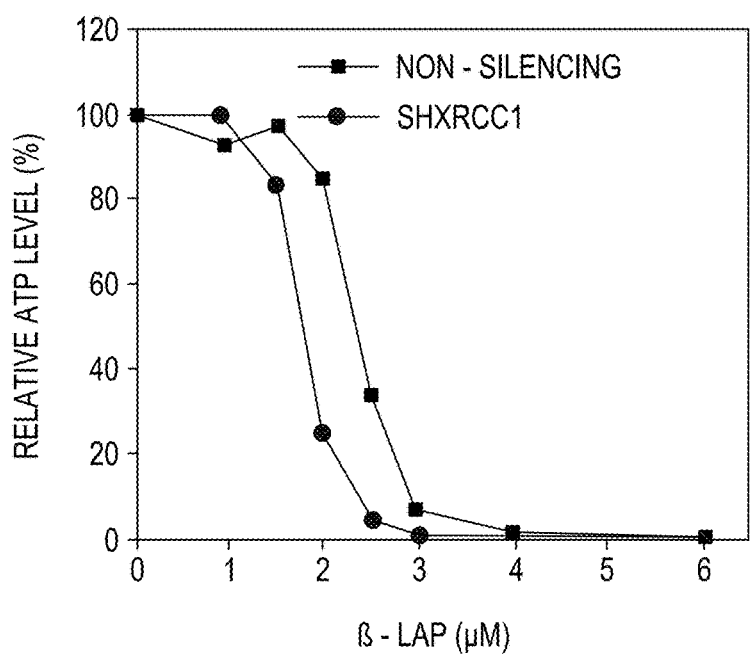
Figure 23B:
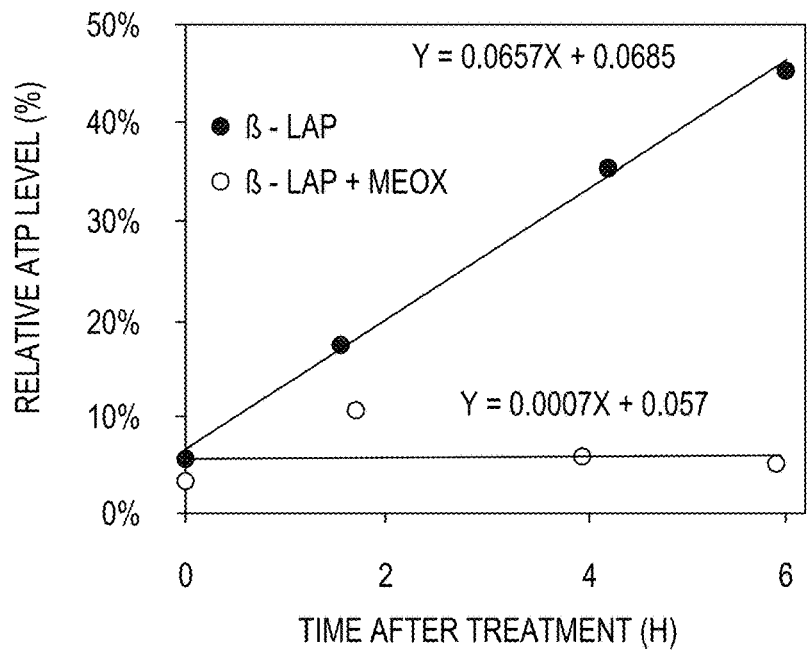
Figure 23B:
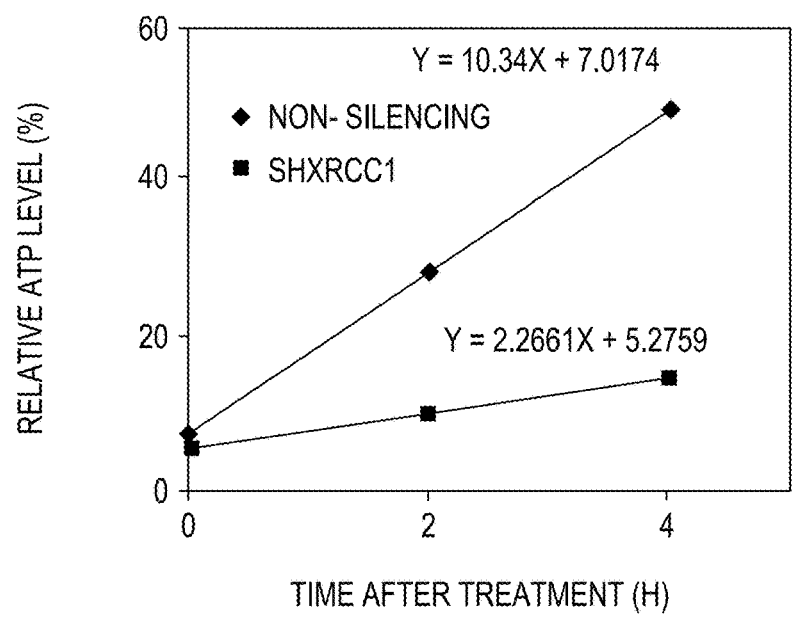
Figure 23C:
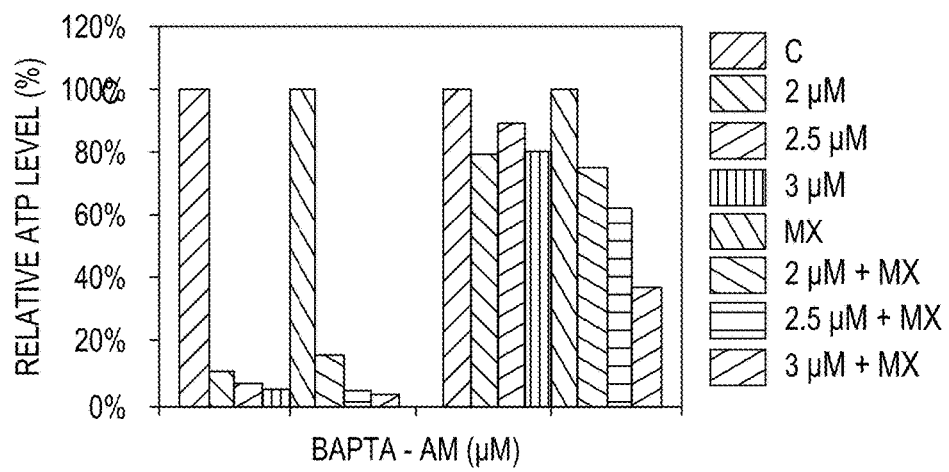
Figure 23D:
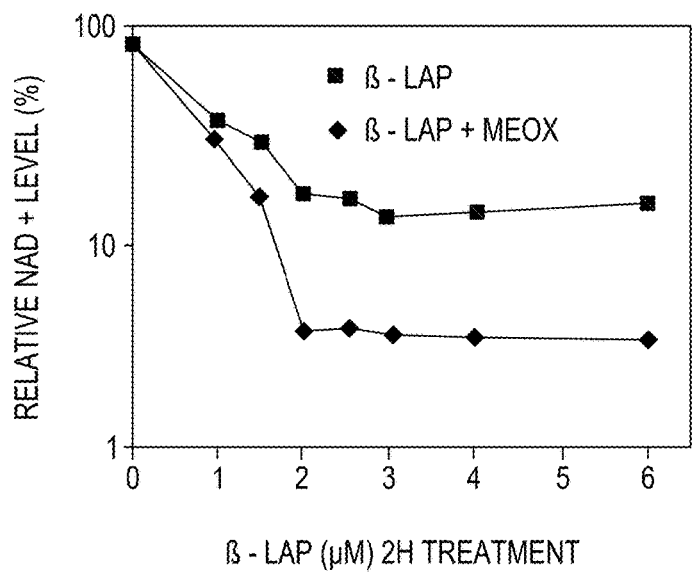
Figure 24A:
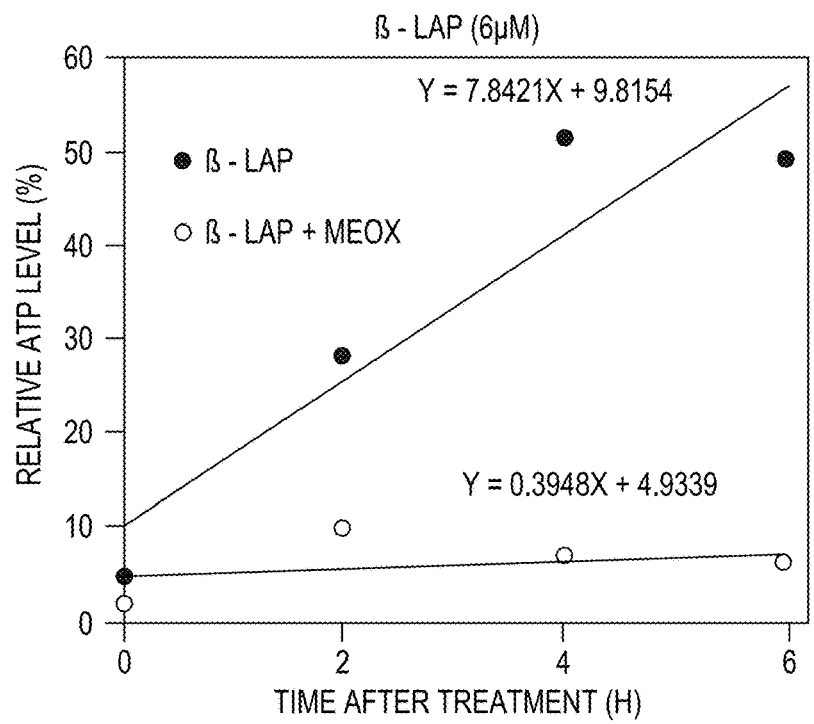
FIG. 24. MeOX suppresses ATP loss recovery after lethal (6 μM or 4 μM) or sublethal (3 μM or 2.5 μM) β-lap treatments 0.
Figure 24B:
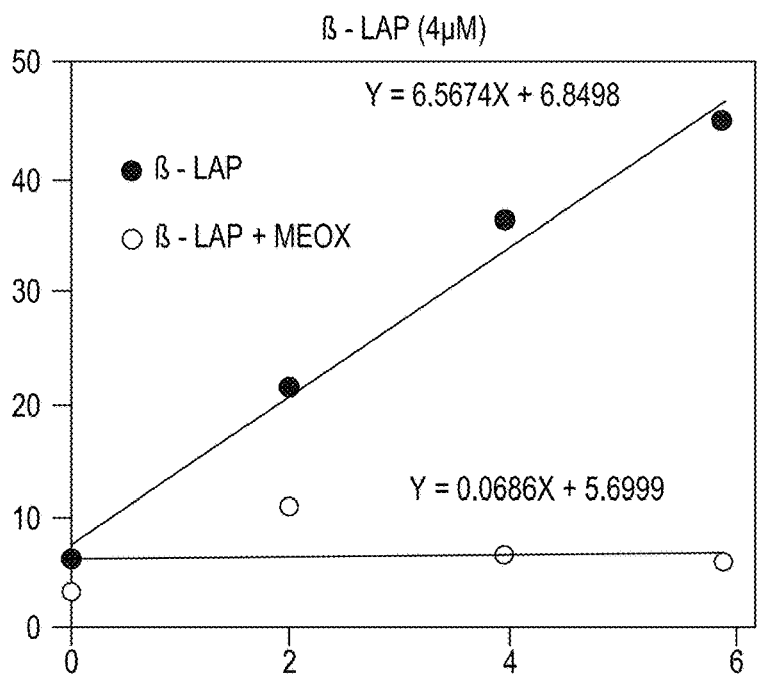
Figure 24C:
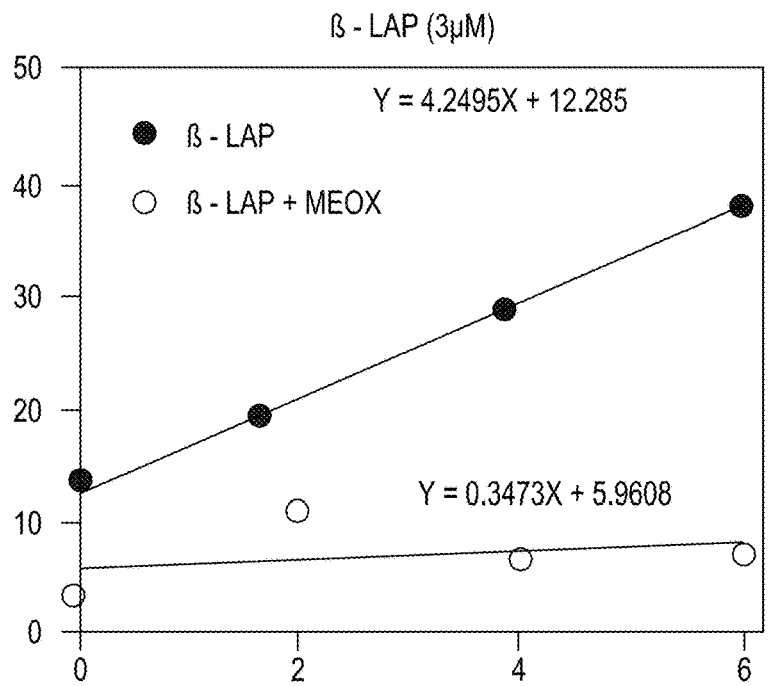
Figure 24D:
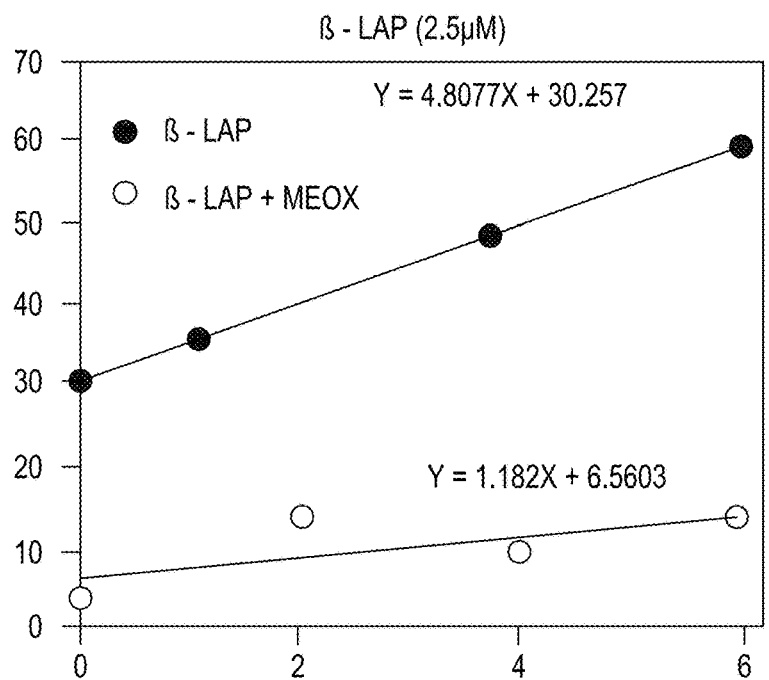

As shown in FIG. 22, addition of nontoxic doses of methoxyamine (MeOX) greatly enhances DNA damage in Mia PaCa-2 cells exposed to sublethal doses of ß-lapachone (2 µM). A) DNA double strand breaks (DSBs), monitored by gamma-H2AX, are greatly enhanced by the addition of nontoxic doses of methoxyamine (MeOX). MeOX, 12 mM; Dicoumarol, NQO1 inhibitor, 50 µM; ß-lapachone doses, indicated or 2 µM. For Mia Paca2 cells, 2-2.5 µM is sublethal, 6 µM is lethal. $H_2O_2$ dose was 500 µM, 2 h. All treatments were 2 h in duration. Cells were treated 2× with MeOX, as a 2 h pretreatment and then for 2 h in combination with ß-lap where applicable.

Methoxyamine pre- and co-treatments prevent ATP recovery responses in Mia PaCa-2 pancreatic cancer cells exposed to NQO1 bioactivatable drugs, such as ß-lapachone (ß-lap) (FIG. 23). A, ATP recovery responses are prevented by MeOX and XRCC1 knockdown, presumably by enhanced PARP1 hyperactivation. B, MeOX addition to ß-lap-treated Mia PaCa2 cells prevents ATP recovery. C, BAPTA-AM, a calcium chelator, prevents MeOX synergistic ATP loss. BAPTA-AM was used at 6 µM. D, Addition of MeOX enhances NAD+ loss, consistent with enhanced PARP1 hyperactivation.

Addition of Methoxyamine (MeOX) prevents ATP recovery responses in ß-lap-treated Mia PaCa2 cells at lethal and sublethal doses (FIG. 24). Lethal doses of ß-lapachone were 6 and 4 µM, whereas 3.0 and 2.5 µM are sublethal doses of ß-lapachone (ß-lap).

Figure 25:
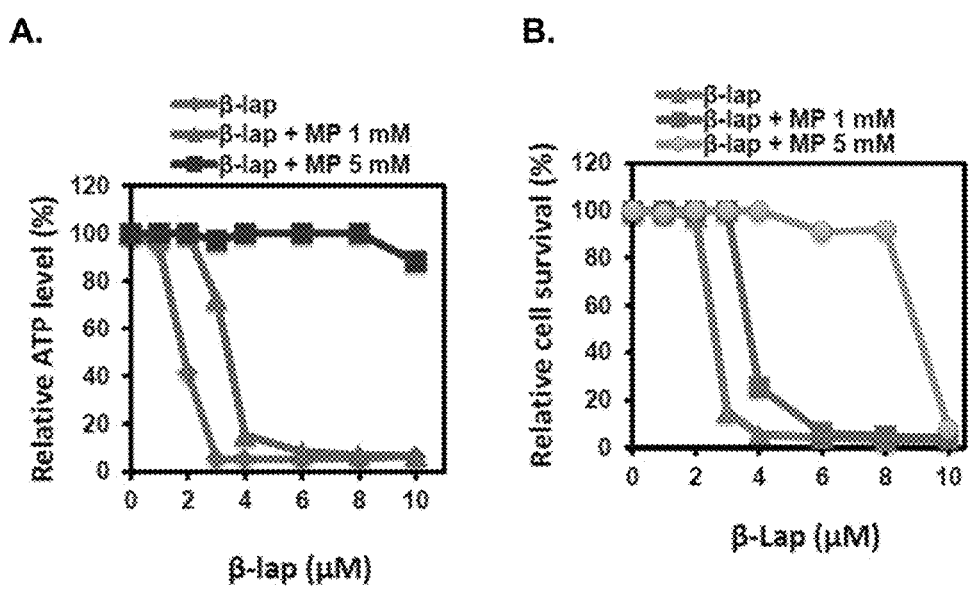
FIG. 25. Methyl pyruvate (MP) suppresses β-lapachone-induced cell death; (A) relative ATP level; (B) relative cell survival.

Methyl pyruvate (MP) suppresses ß-lapachone-induced cell death (FIG. 25). While the effects could be due to recovery of the TCA cycle, MP is also an outstanding oxygen free radical (reactive oxygen species, ROS) scavenger.

Figure 26:
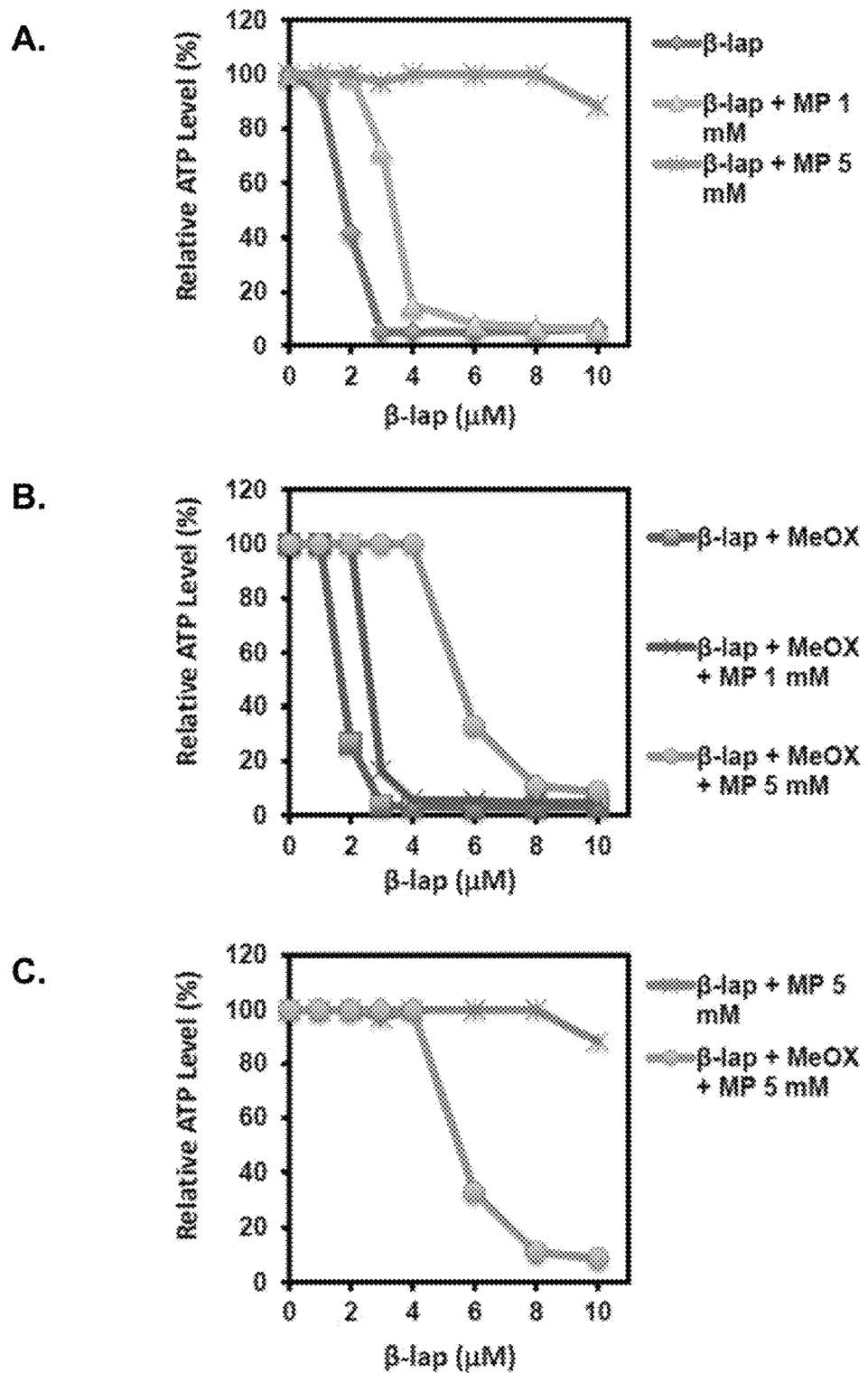
FIG. 26. MeOX attenuates methyl pyruvate effect in protecting cells; (A) β-lap control and addition of MP; (B) β-lap and MeOX, and (C) β-lap and MP or β-lap and MeOX.

Addition of Methoxyamine attenuates MP effects, presumably because less initial ROS ($H_2O_2$) is required to create unrepairable (and MeOX-modified) AP sites (FIG. 26). ß-Lap doses indicated, MP used at 1 or 5 mM, and MeOX was used at 12 mM.

Figure 27A:
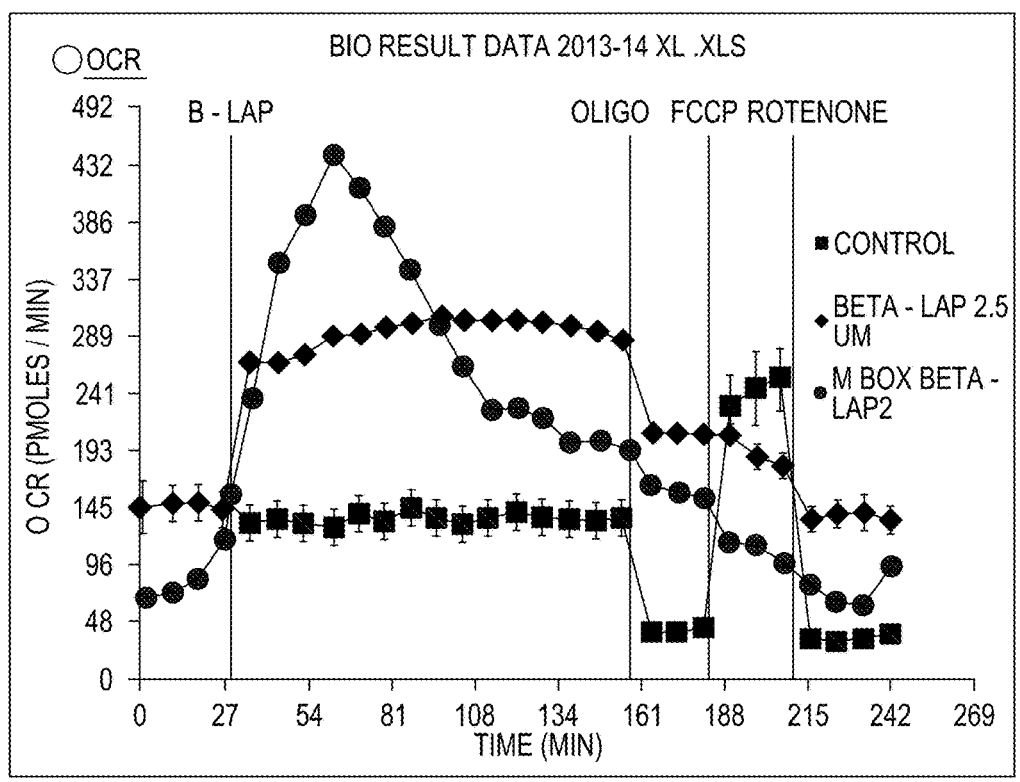
FIG. 27. Methoxyamine (MeOX) accelerates PARP1 hyperactivation-induced NAD+/ATP loss, further accelerating 02 consumption by an NQO1-dependent process in ß-lapachone-exposed Mia PaCa-2 pancreatic cells. A. ß-Lapachone enhances oxygen consumption rates (OCR) in Mia PaCa2 cells. Lethal doses of ß-lap cause dramatic OCR spikes, and subsequent losses of all metabolic capacity. Sublethal doses of ß-lap cause consistently elevated OCRs over time. Both responses are NQO1-mediated. B, addition of MeOX enhances OCR rates in combination with sublethal doses of ß-lap, similar to a lethal dose of ß-lapachone (4 μM), presumably because of the loss of NAD+ and ATP derived from PARP1 hyperactivation.
Figure 27B:
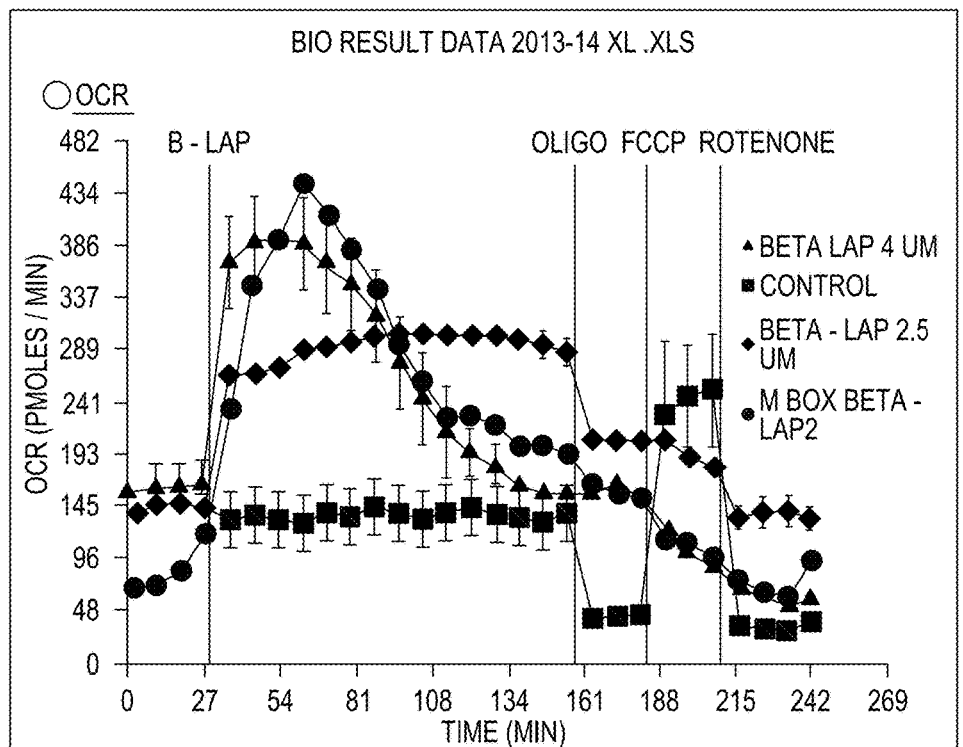

Methoxyamine (MeOX) accelerates PARP1 hyperactivation-induced NAD+/ATP loss, further accelerating reparation in ß-lapachone-exposed Mia PaCa-2 cells (FIG. 27). A. ß-Lapachone enhances oxygen consumption rates (OCR) in Mia PaCa2 cells. Lethal doses of ß-lap cause dramatic OCR spikes, and subsequent losses of all metabolic capacity. Sublethal doses of ß-lap cause consistently elevated OCRs over time. Both responses are NQO1-mediated. B, addition of MeOX enhances OCR rates in combination with sublethal doses of ß-lap, similar to a lethal dose of ß-lapachone (4 µM), presumably because of the loss of NAD+ and ATP derived from PARP1 hyperactivation.

Figure 28:
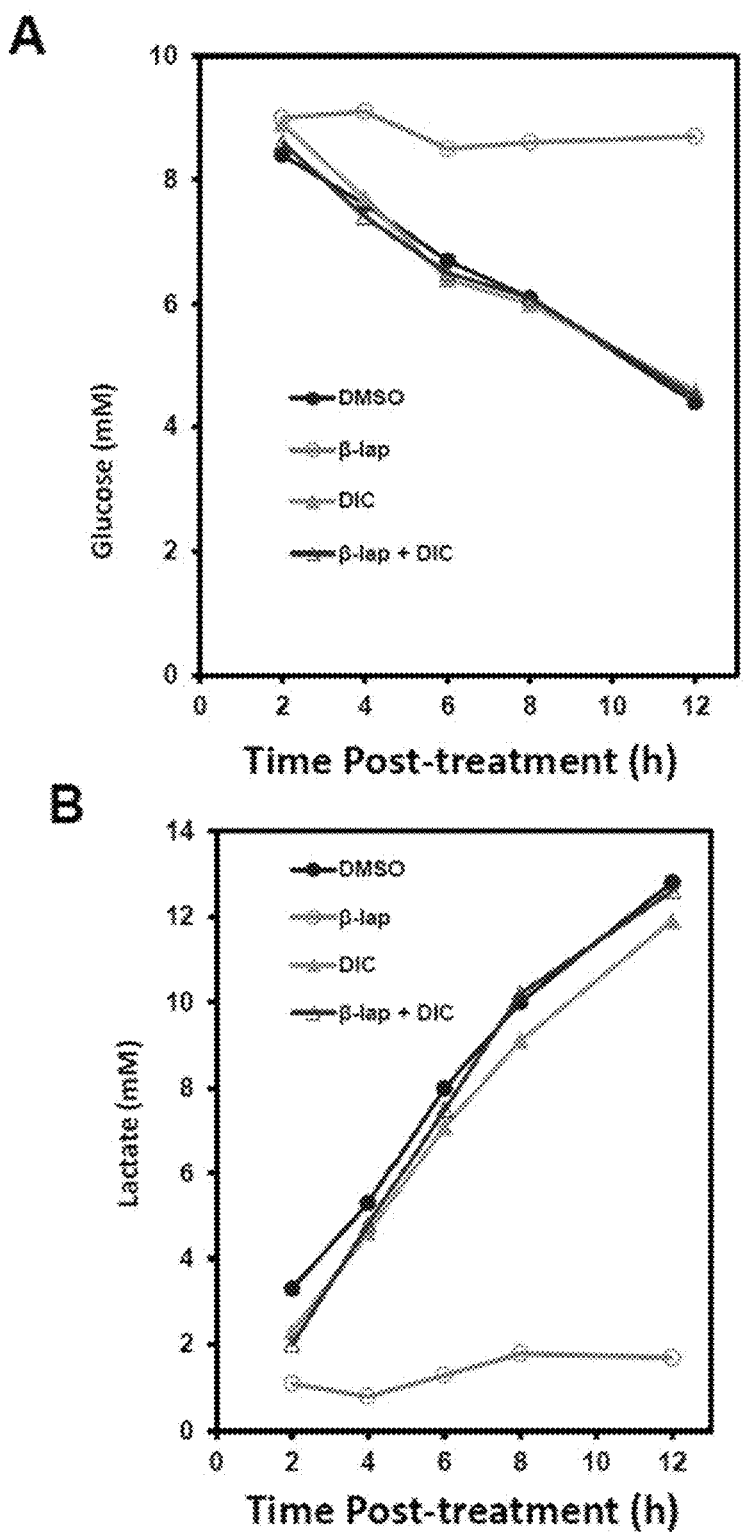
FIG. 28. NQO1 bioactivatable drug treatment suppresses glycolysis in Mia PaCa2 cells. Both glucose utilization (A) and lactate production (B) are suppressed.
Figure 29:
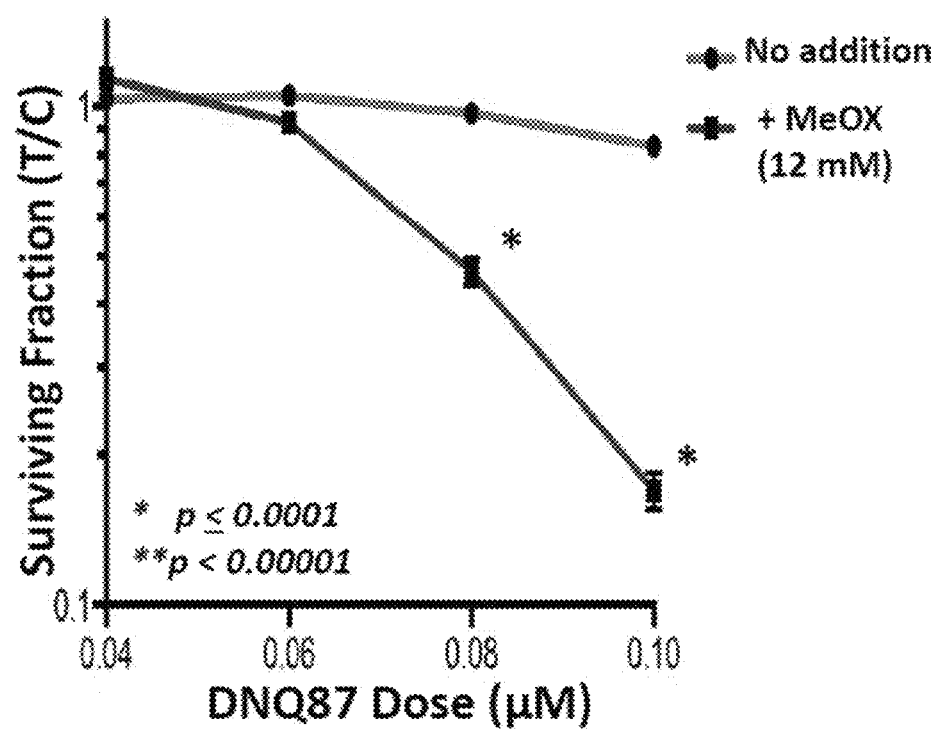
FIG. 29. A549 NSCLC cells were co-treated with 12 mM Methoxyamine (MeOX) and DNQ 87 for 2 h and relative survival was measured (as in Huang et al., Cancer Res., 2012).

NQO1 bioactivatable drug treatment suppresses glycolysis in Mia PaCa2 cells (FIG. 28). Both glucose utilization (A) and lactate production (B) are suppressed. A549 NSCLC cells were co-treated with 12 mM Methoxyamine (MeOX) and DNQ 87 for 2 h (FIG. 29) and relative survival was measured (as in Huang et al., Cancer Res., 2012).

PARP1 Inhibition Enhances the Tumor-Selective Lethality of NQO1 Bioactivatable Drugs.

Figure 30:
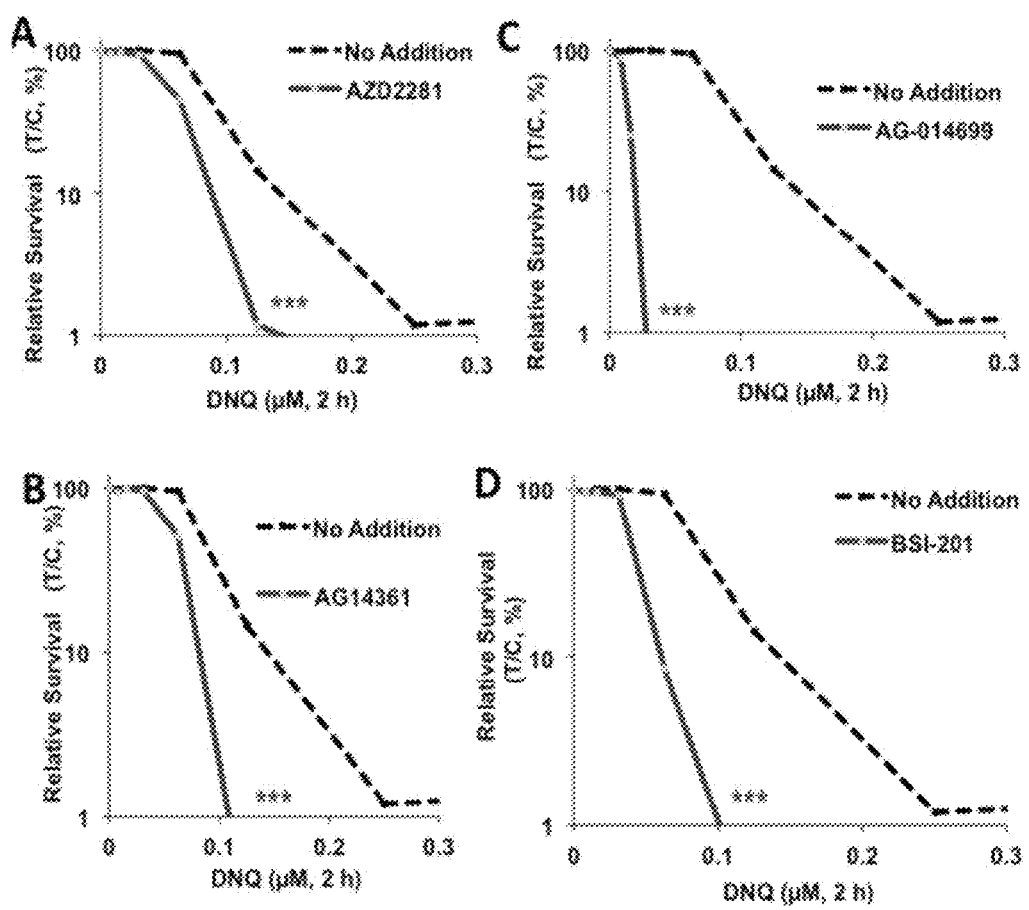
FIG. 30. PARP1 inhibition enhances lethality of NQO1 bioactivatable drugs; (A) AZD2281; (B) AG14361; (C) AG-014699; (D) BSI-201.
Figure 31:
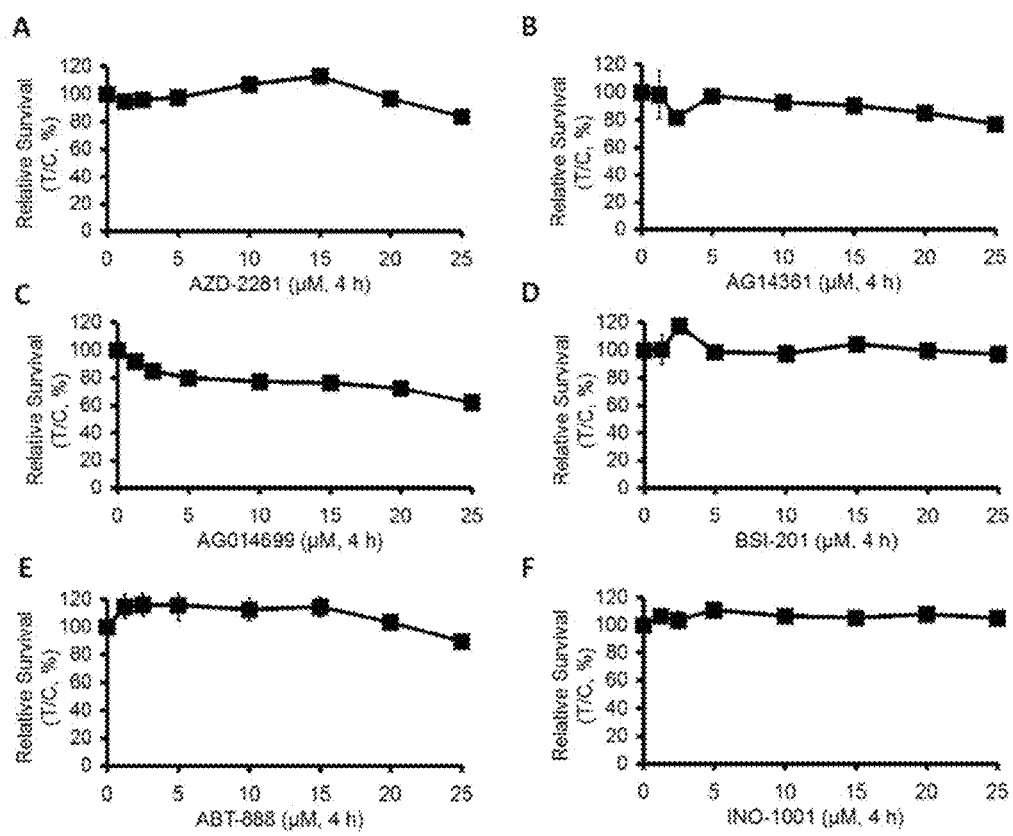
FIG. 31. Determination of nonlethal doses of PARP1 inhibitors alone in A549 NSCLC cells; (A) AZD-2281; (B) AG14361; (C) AG014699; (D) BSI-201; (E) ABT-888; (F) INO-1001.
Figure 32:
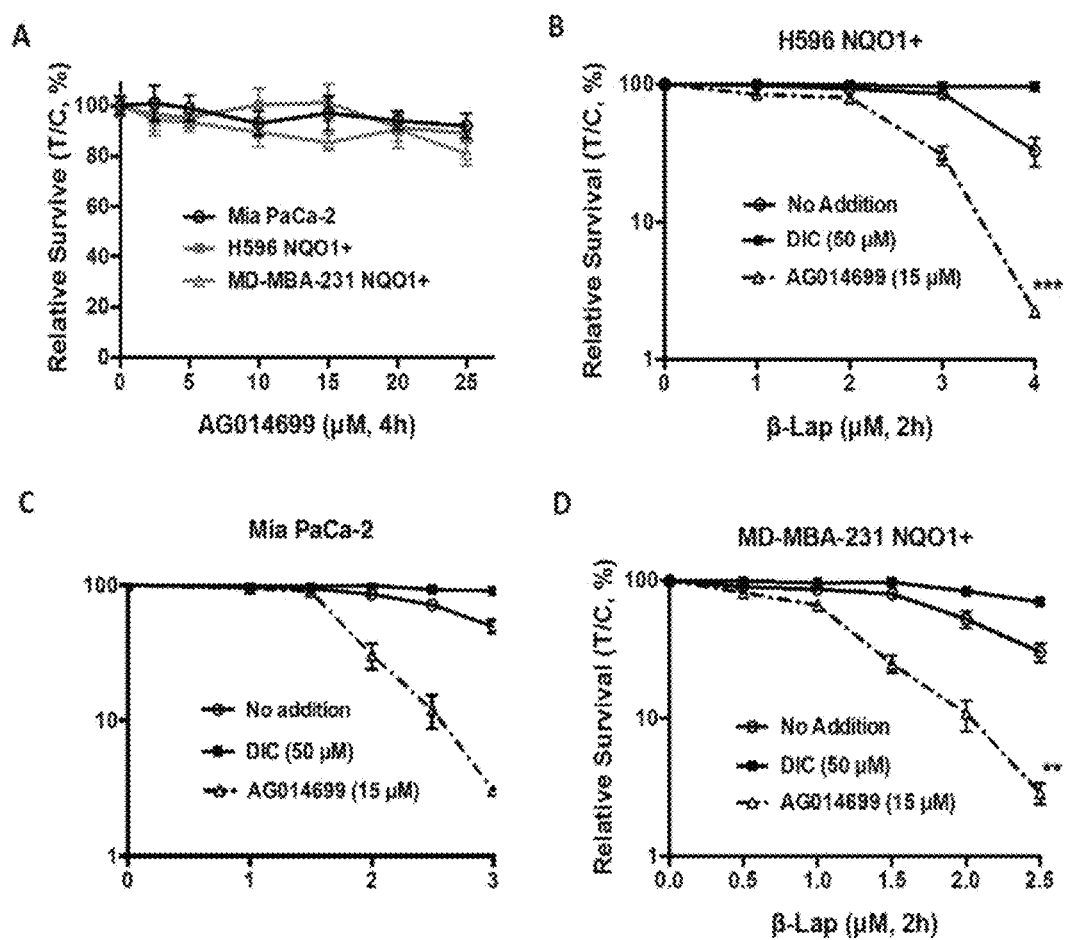
FIG. 32. Data for the PARP1 inhibitor, AG014699 (rucaparib); (A) AG014699; (B) β-lap and AG014699; (C) AG014699; (D)β-lap and AG014699.

PARP1 inhibitors enhance the lethality of NQO1 bioactivatable drugs (FIG. 30). Mia PaCa-2 cells were treated for 2 hours with the inhibitors noted in FIG. 30 and then with DNQ+ the inhibitors (all at 15 µM) for 2 hours. Cells were then washed and allowed to grow for 7 days and relative survival was assessed as in Huang et al., *Cancer Res.*, 2012, 72(12), 3038-3047, which also provides additional useful methods and techniques that can be incorporated into the method described herein. All of the inhibitors, except BSI-201, inhibited PAR formation. Further analyses showed that BSI-201 was not an efficacious PARP1 inhibitor, but did cause DNA damage, which is the mechanism by which this inhibitor synergized with NQO1 bioactivatable drugs (DNQ (shown) or ß-lap). FIG. 31 shows data for the determination of nonlethal doses of PARP1 inhibitors alone in A549 NSCLC cells. FIG. 32 shows data obtained for the PARP1 inhibitor, AG014699.

Figure 33:
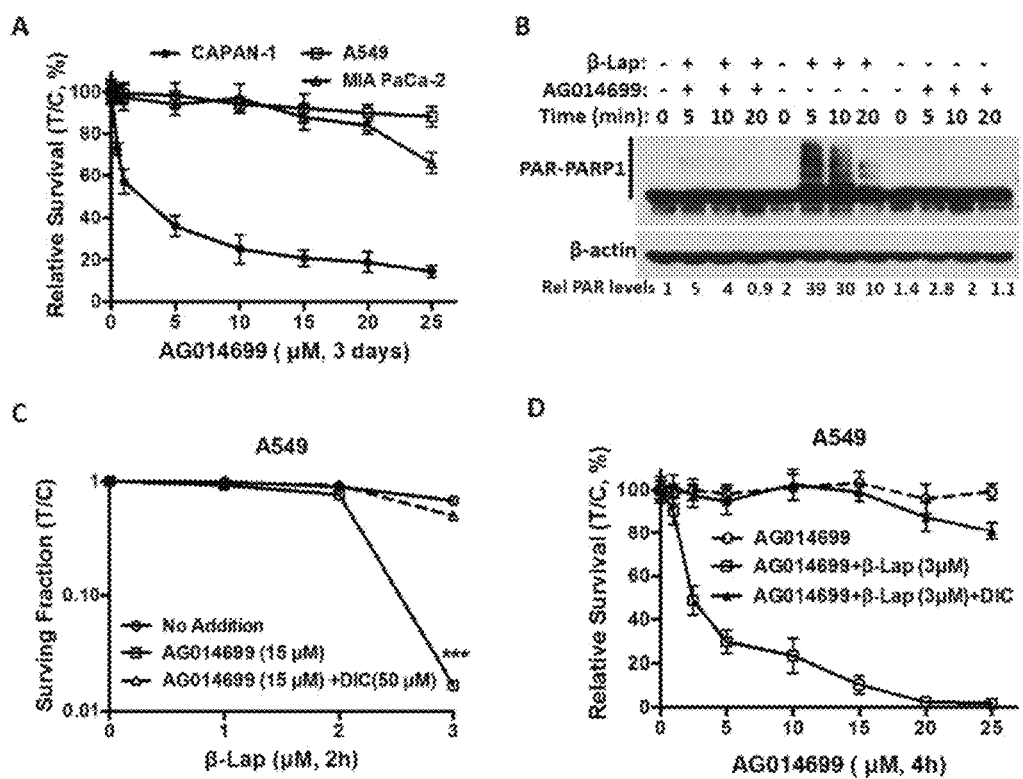
FIG. 33. AG014699 enhances the NQO1-dependent lethality of ß-lapachone in A549 NSCLC cells. A, control to demonstrate synthetic lethality of drug alone against a BRCA1-/- CAPAN-1 cells, whereas other BRAC1 wild-type cancer cells (A549 and Mia PaCa-2 cells are completely resistant to the PARP1 inhibitor. B, Demonstration that AG014699 inhibits PARP1 hyperactivation in response to ß-lap. C, Synergistic lethality of AG014699 in combination with ß-lap, which is prevented with the NQO1 inhibitor, dicoumarol. D, Dose-response of AG014699 in combination with ß-lap, and reversal by dicoumarol addition.

AG014699 enhances the NQO1-dependent lethality of ß-lapachone in A549 NSCLC cells (FIG. 33). A, control to demonstrate synthetic lethality of drug alone against a BRCA1−/− CAPAN-1 cells, whereas other BRAC1 wild-type cancer cells (A549 and Mia PaCa-2 cells are completely resistant to the PARP1 inhibitor. B, Demonstration that AG014699 inhibits PARP1 hyperactivation in response to ß-lap. C, Synergistic lethality of AG014699 in combination with ß-lap, which is prevented with the NQO1 inhibitor, dicoumarol. D, Dose-response of AG014699 in combination with ß-lap, and reversal by dicoumarol addition.

Figure 34:
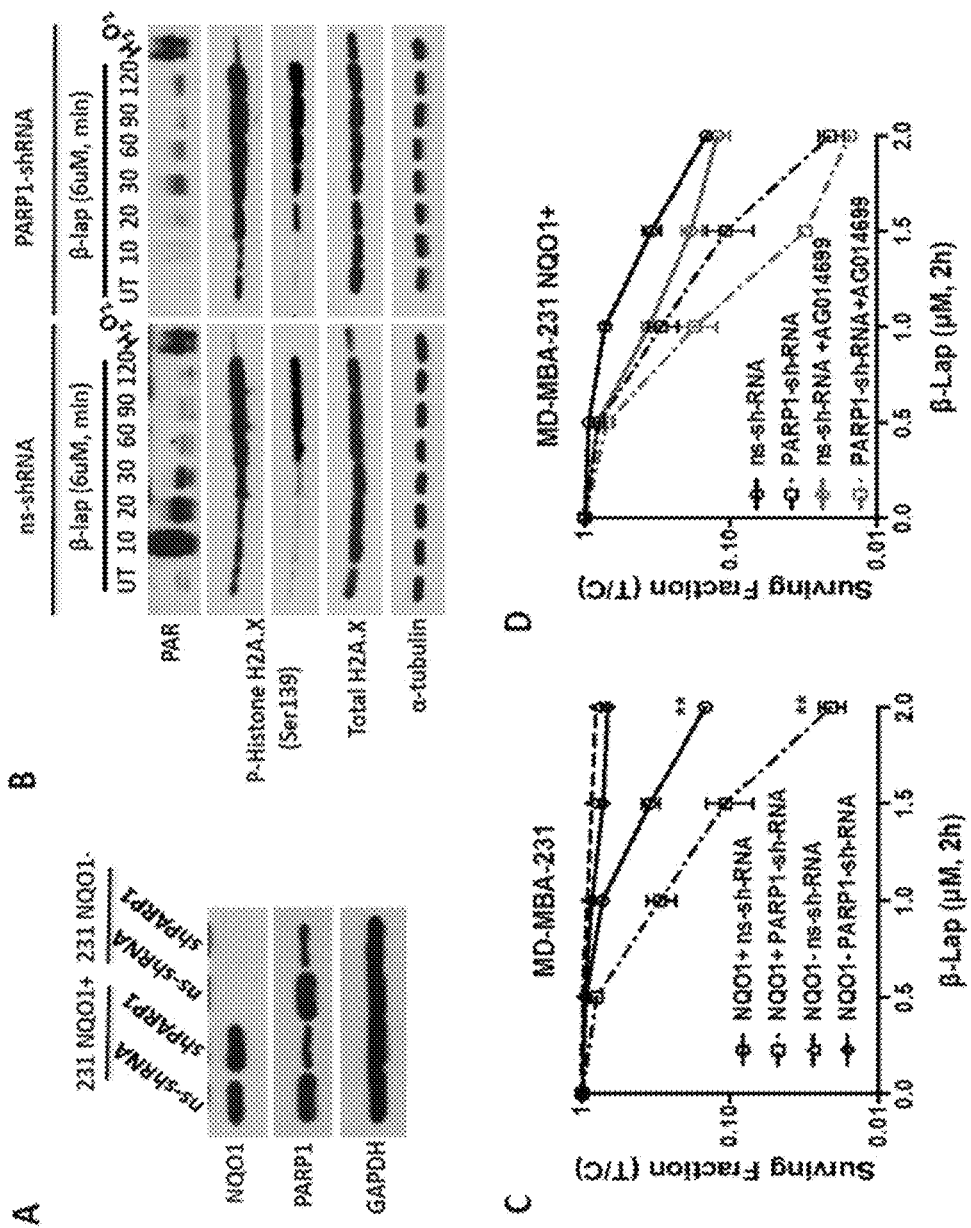
FIG. 34. PARP1 knockdown enhances lethality of ß-lapachone in triple negative MDA-MB-231 (231) breast cancer cells; (A) 231 NQO1+/−; (B) ns-shRNA and PARP1-shRNA; (C) surviving fraction of MD-MBA-231; (D) surviving fraction of MD-MBA-231 NQO1+.

PARP1 knockdown enhances lethality of ß-lapachone in triple negative MDA-MB-231 (231) breast cancer cells (FIG. 34). A. Stable PARP1 shRNA knockdown cells developed by us (Bentle et al., *JBC* 2006). Western blots demonstrate stable knockdown in cells expressing or lacking NQO1. B. Demonstrates dramatically reduced PAR-PARP1 formation in PARP1 knockdown cells. Note that DNA double strand breaks occur much sooner than in PARP1 wild-type cells. C. PARP1 knockdown sensitizes cells to ß-lap in long-term survival assays. Although PARP1 knockdown suppresses programmed necrosis induced by ß-lap (Bentle et al., *JBC* 2006), the long-term consequences are that without PARP1 cells cannot repair DNA lesions created by NQO1 bioactivatable drugs, such as ß-lap, and those lesions are converted to DSBs that eventually cause cells to die through regular caspase-mediated pathways. D. Addition of AG014699 to PARP1 knockdown 231 cells does not significantly enhance their lethality induced by ß-lap. All PARP1 inhibitors have shown similar responses, except for BSI-201.

Figure 35:
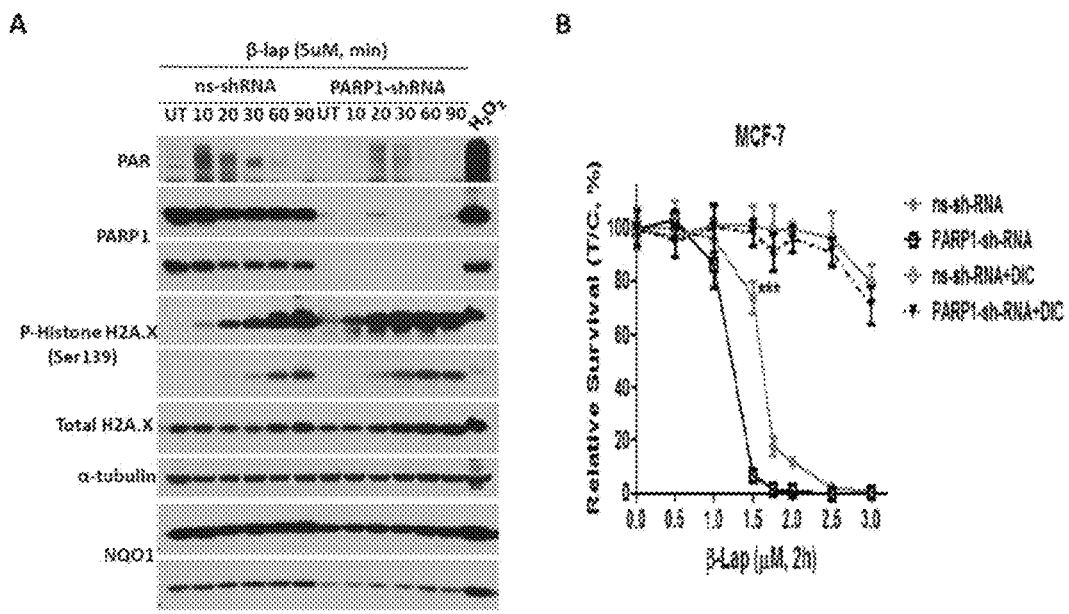
FIG. 35. PARP1 knockdown in MCF-7 breast cancer cells also enhances ß-lap lethality; (A) ß-lap at 5 μM; (B) relative survival of MCF-7 cells.

PARP1 knockdown in MCF-7 breast cancer cells also enhances ß-lap lethality (FIG. 35). A, B, PARP1 knockdown in NQO1 over-expressing MCF-7 cells greatly enhances ß-lap lethality. Note that NQO1 inhibition by dicoumarol (DIC) prevents synergy by blocking NQO1 bioactivation.

Figure 36:
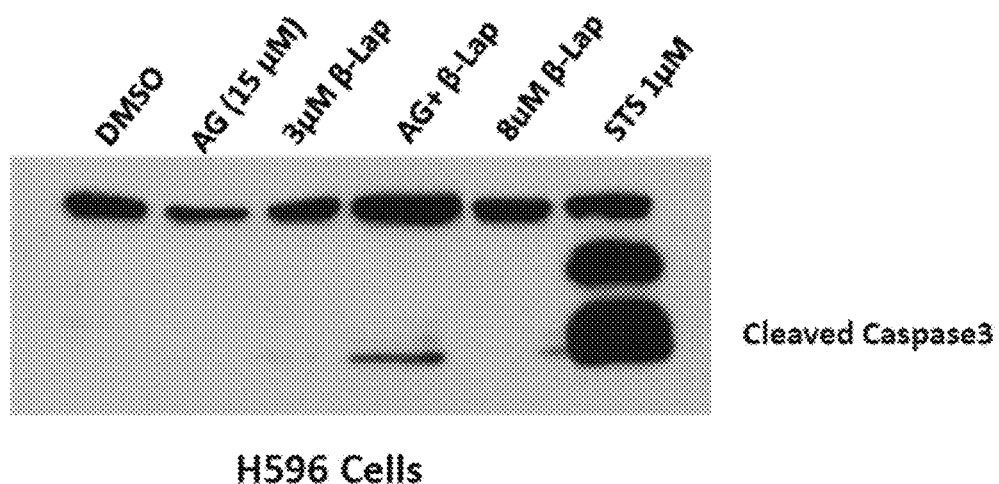
FIG. 36. NQO1+H596 NSCLC cells treated with nontoxic doses of ß-lap+nontoxic doses of AG014699 show evidence of apoptosis in the form of cleaved caspase-3.

NQO1+H596 NSCLC cells treated with nontoxic doses of ß-lap+nontoxic doses of AG014699 show evidence of apoptosis in the form of cleaved caspase-3 (FIG. 36). STS, staurosporine (1 μkm, 1 h) serves as a positive control. The active form of caspase 3 is the lower band on the blot.

Figure 37:
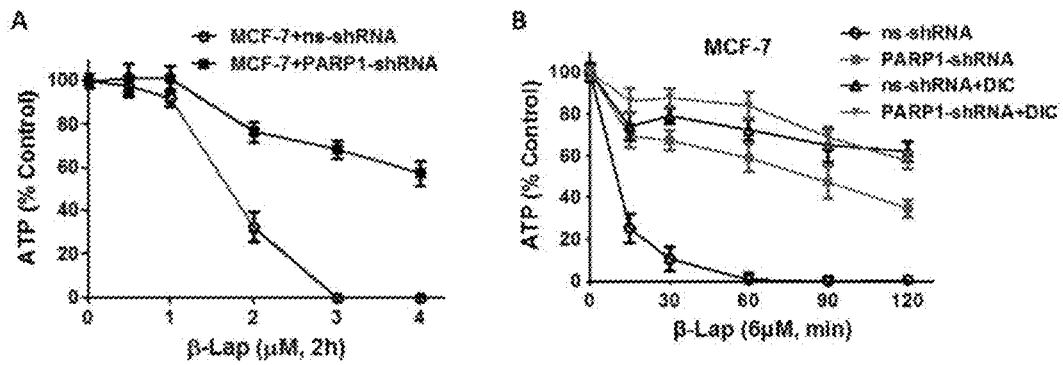
FIG. 37. PARP1 shRNA stable knockdown enhances lethality (A) but suppresses ATP loss (B) due to the suppression (loss) of PARP1 hyperactivation.

PARP1 shRNA stable knockdown enhances lethality (A) but suppresses ATP loss (B) due to the suppression (loss) of PARP1 hyperactivation (FIG. 37).

Figure 38:
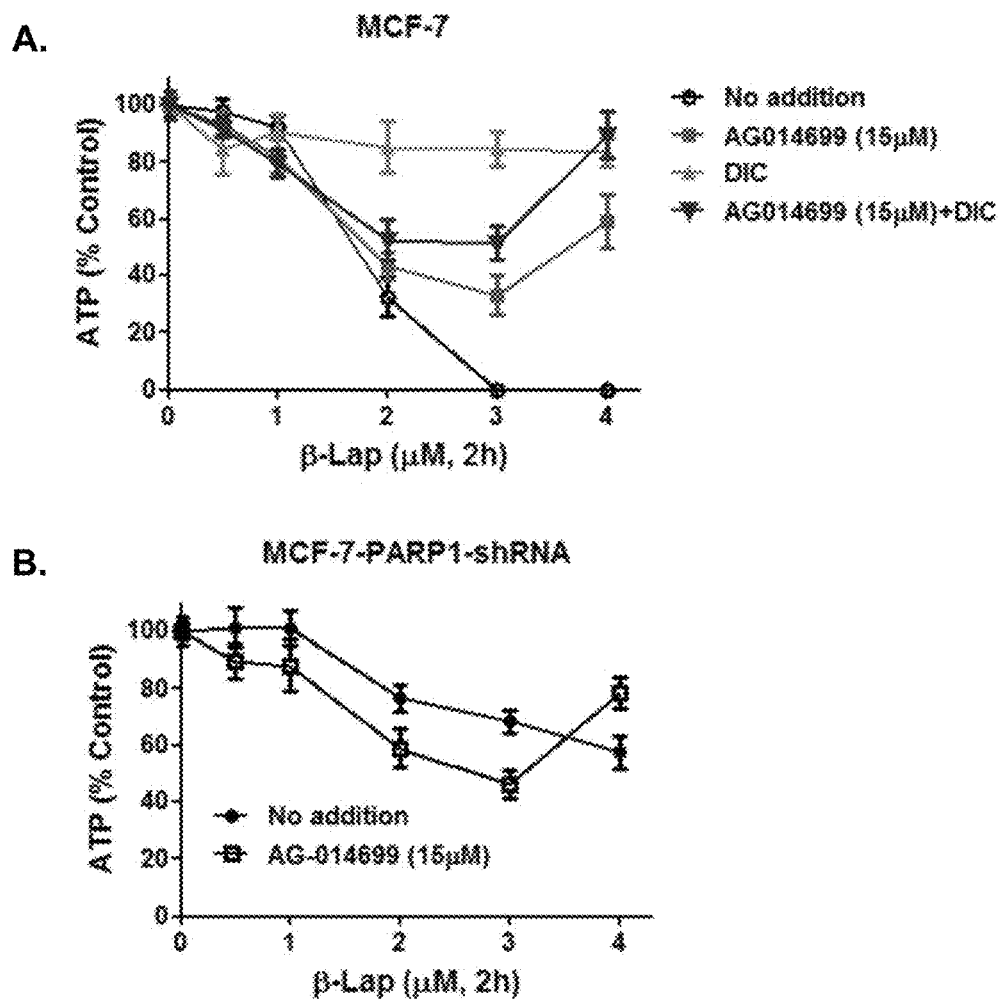
FIG. 38. ß-Lap-induced ATP loss is prevented with PARP1 shRNA stable knockdown or addition of AG014699; (A) MCF-7; (B) MCF-7-PARP1-shRNA.
Figure 39:
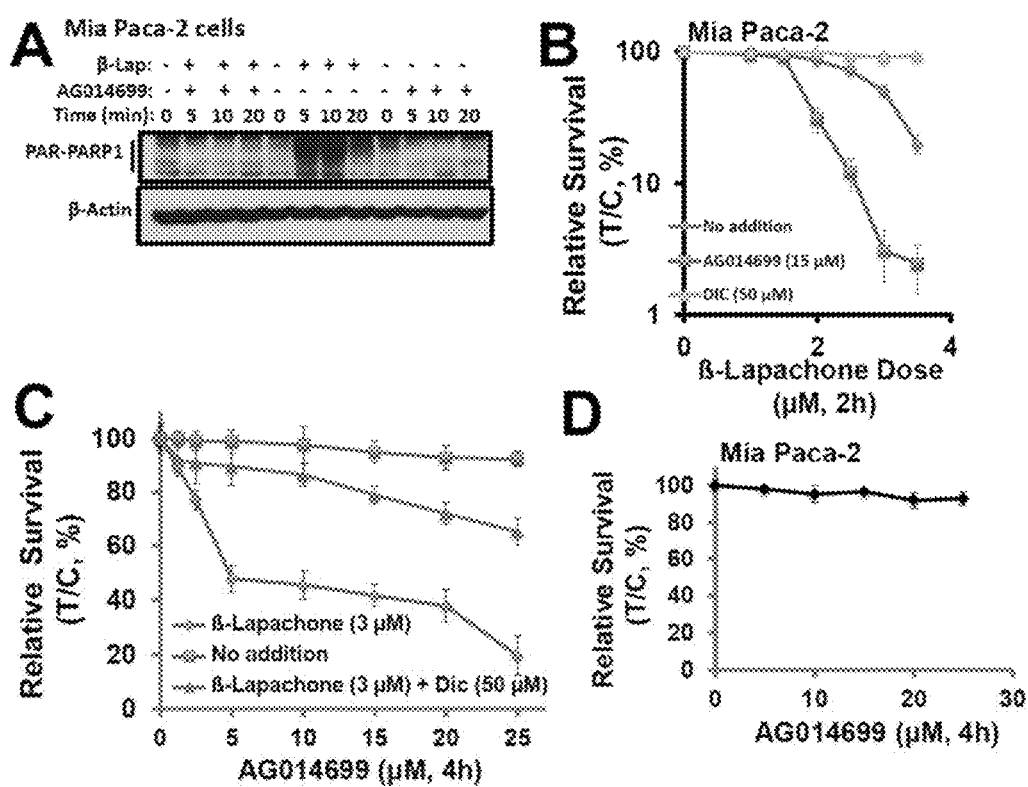
FIG. 39 show studies in Mia Paca-2 and DNQ combined PARP1 inhibitor data (A-D).
Figure 40:
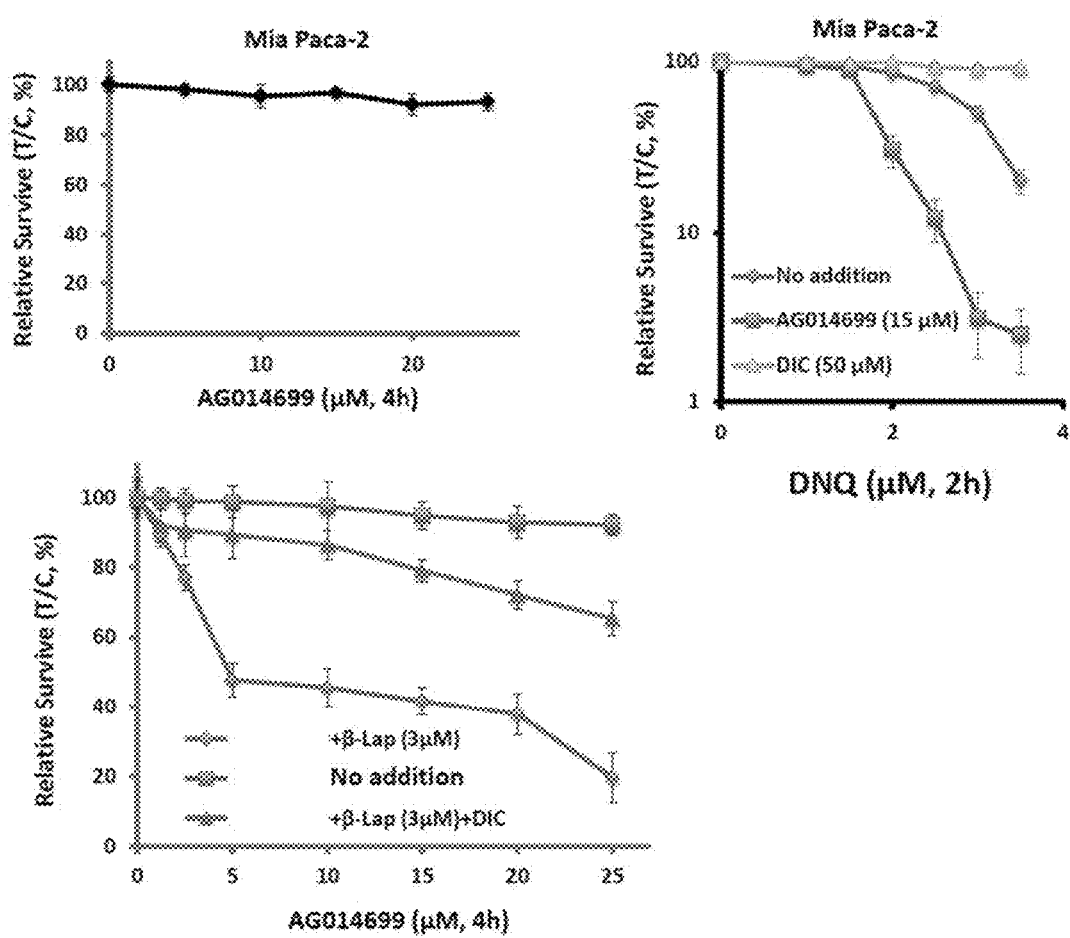
FIGS. 40-42 show studies in Mia Paca-2 and some DNQ combined PARP1 inhibitor data.
Figure 41:
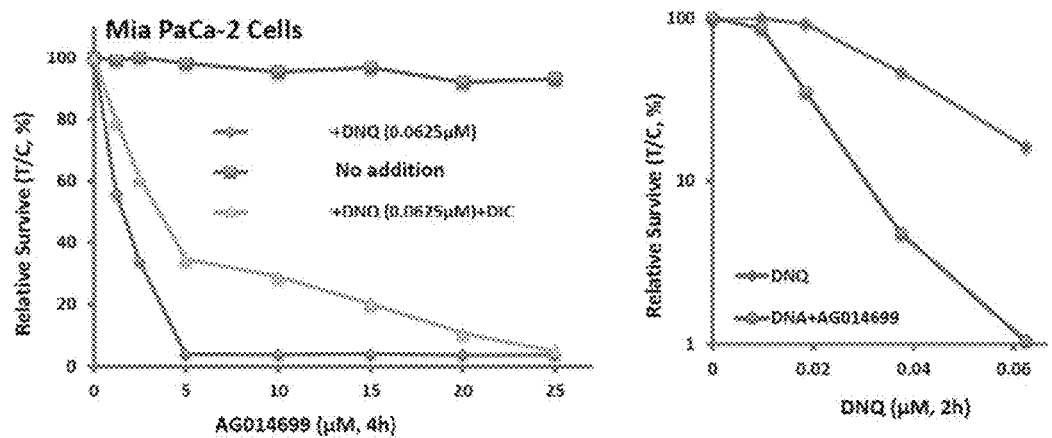
Figure 42:
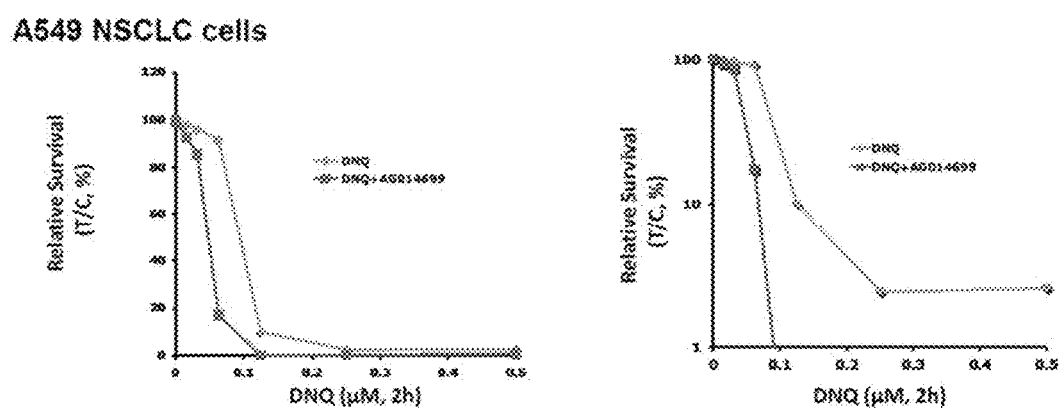

As shown in FIG. 38, ß-Lap-induced ATP loss is prevented with PARP1 shRNA stable knockdown or addition of AG014699, even though synergistic lethality occurs between ß-lap and PARP1 loss or inhibition. FIG. 39-42 show studies in Mia Paca-2 and some DNQ combined PARP1 inhibitor data.

Figure 43:
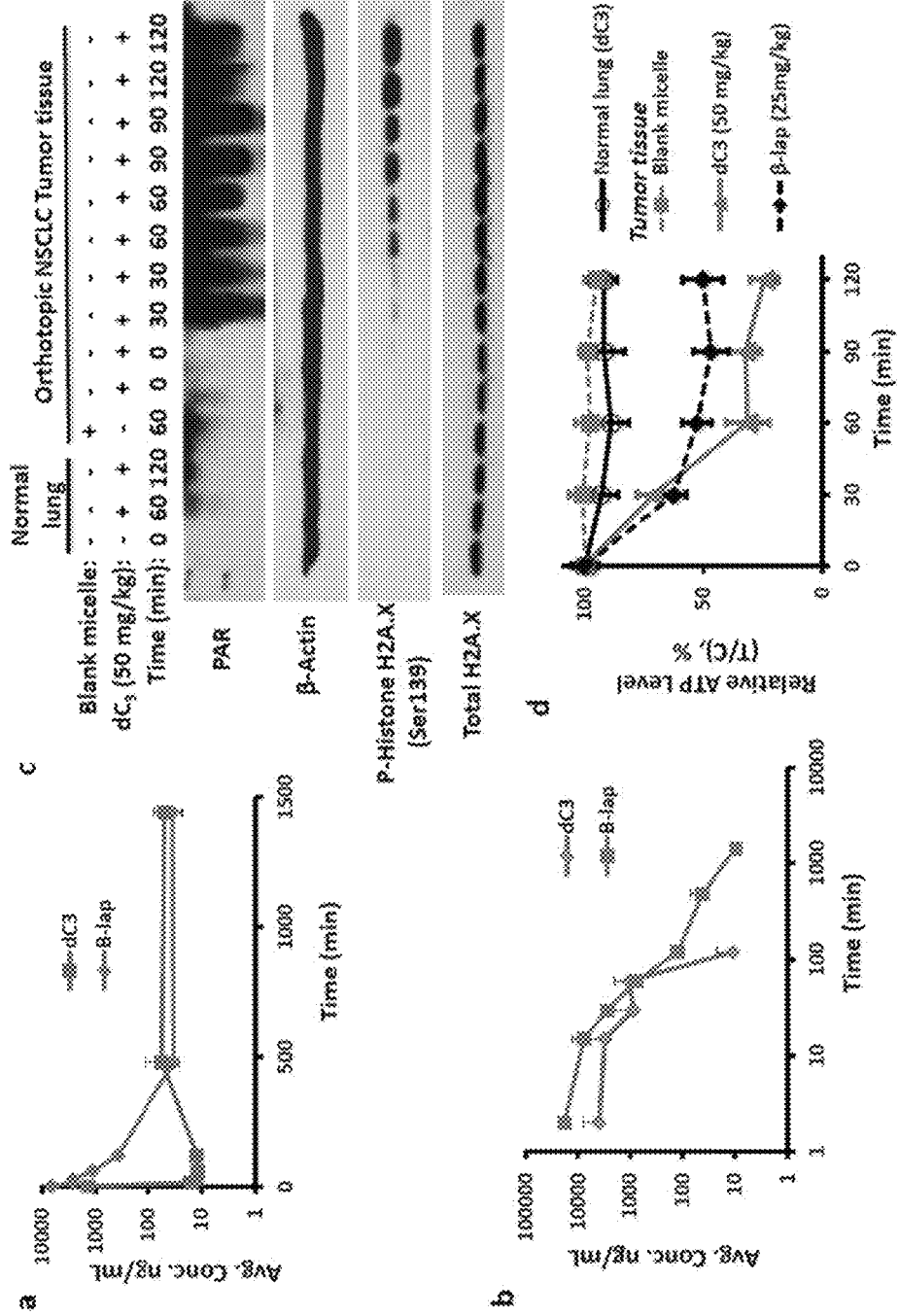
FIG. 43. Pharmacokinetic analysis and target valuation of $dC_3$ micelles in vivo; (A) dC3 and β-lap; (B) dC3 and β-lap; (C) comparison of blank micelles vs. dC3; (D) relative ATP levels.
Figure 44:
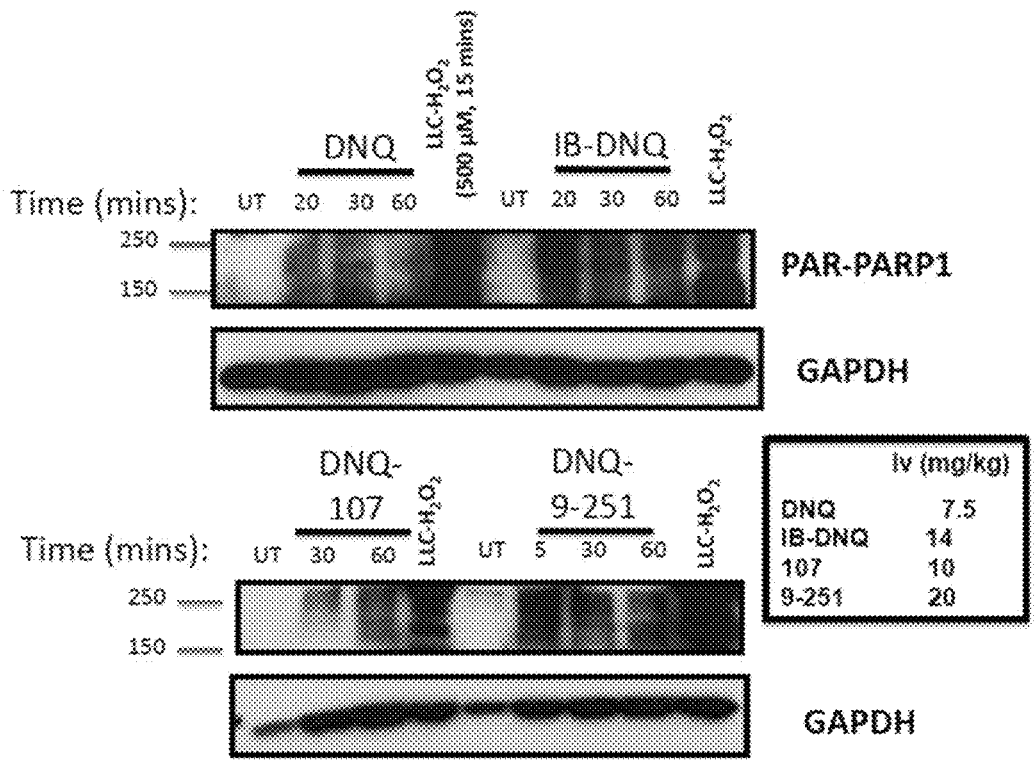
FIG. 44. DNQ Derivative PAR-PARP1 Formation in vivo.

FIG. 43 shows pharmacokinetic analysis and target valuation of dC3 micelles in vivo. a, blood concentrations of dC3 and β-lap (converted from dC3). Pharmacokinetic parameters (e.g., $t_{1/2}$) were calculated using a two-compartment pharmacokinetic model. b, Tumor concentrations of dC3 and β-lap (converted from dC3). FIG. 44 shows DNQ derivative PAR-PARP1 formation in vivo. The MDT pilot study data is shown below in Table 2-1.

TABLE 2-1

DNQ Derivatives Pilot Study of Maximum Tolerated Dose (MTD).

| Compound | NOD/SCID | Doses (mg/kg) | Dead mice (5 IV.) | MTD* |
|---|---|---|---|---|
| DNQ | 3 | 7.5 | 2 | 6 |
| 87 | 3 | 14 | 0 | ~16 |
| 107 | 3 | 10 | 1 | 8 |
| 9-251 | 3 | 20 | 0 | 20 |
| 10-41 | 3 | 15 | 3 | 7 |

NOD/SCID: 1 million 3LL-Luc cells were injected into each mouse, and after two days IV was begun.
*Pilot experiments indicate a new practical MTD in NOD/SCID, iv, 1x every other day, 5 injections.

Figure 45:
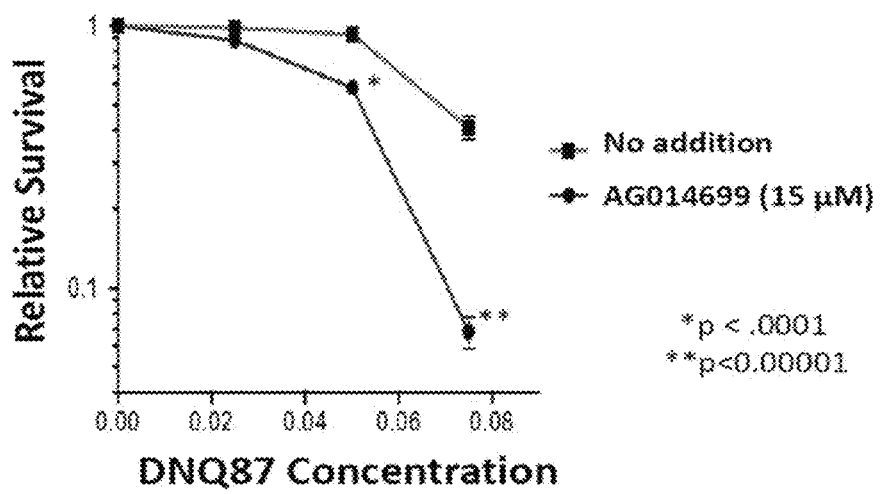
FIG. 45. A549 treatment with DNQ-87 and a PARP inhibitor (AG014699).
Figure 46:
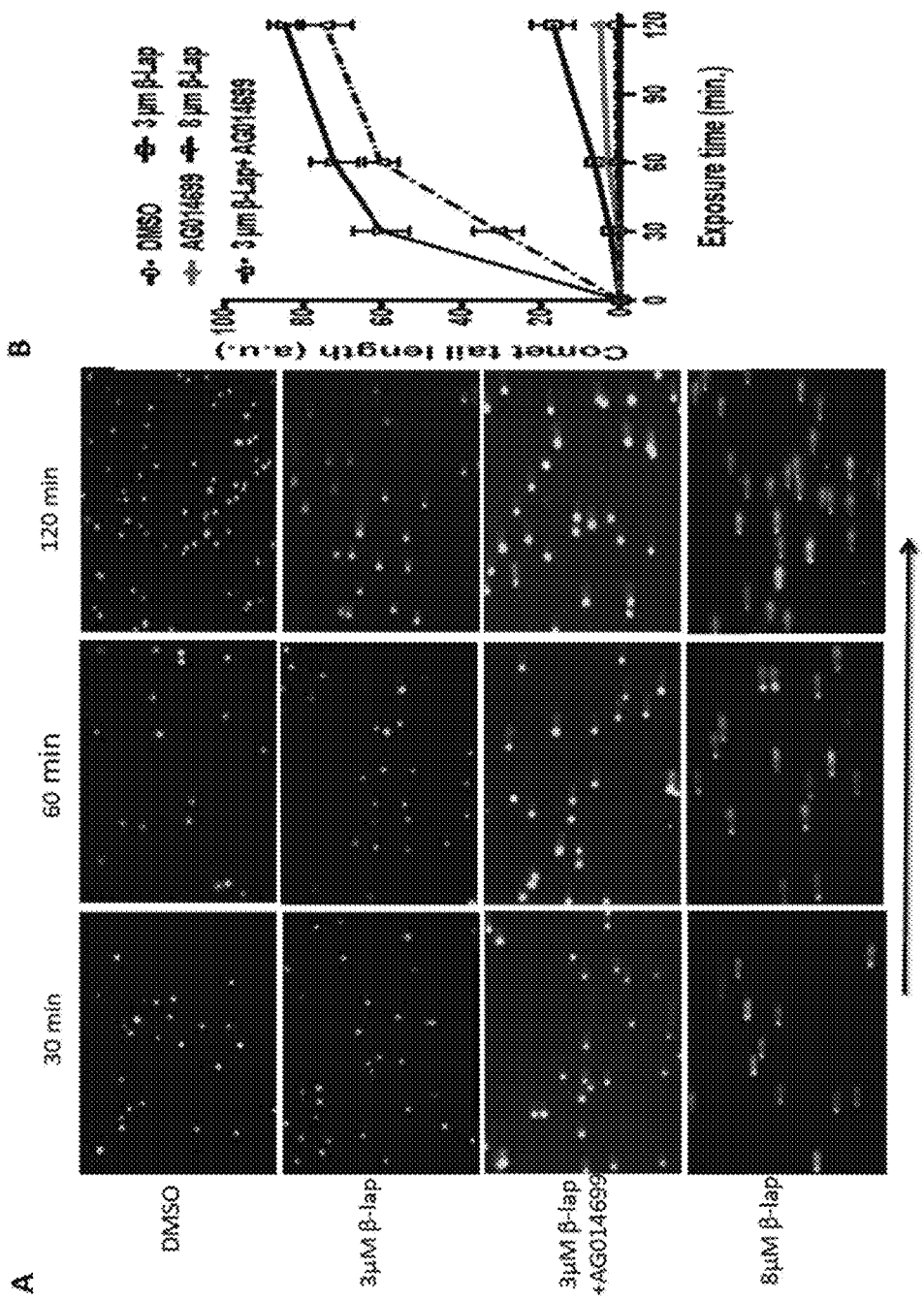
FIG. 46. DNA damage via combinatorial treatment. (A) A549 NSCLC cells were pre-treated with or without Rucaparib (AG014699) and then exposed to a nontoxic dose of ß-lapachone (3 μM) at the concentrations indicated with or without the same PARP1 inhibitor. Cells were also exposed to a lethal dose of ß-lapachone (8 μM). Cells were then analyzed by neutral comet assays and DNA damage graphed in (B). (B) Data show that DNA damage is dramatically increased in cells exposed to sublethal doses of ß-lap in the presence of PARP1 inhibitors, equivalent to DNA lesions created by a lethal dose of ß-lapachone.
Figure 47D:
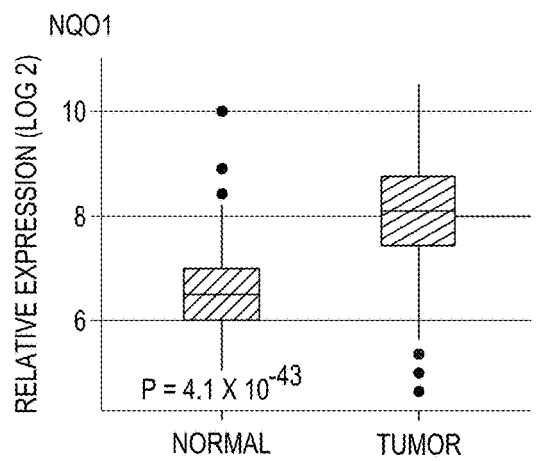
FIG. 47. NQO1/Catalase ratios are elevated in breast cancer tumors, but low in associated normal tissue; (A) A-F patient sample counts and expression data; (B) NQO1 expression.
Figure 47E:
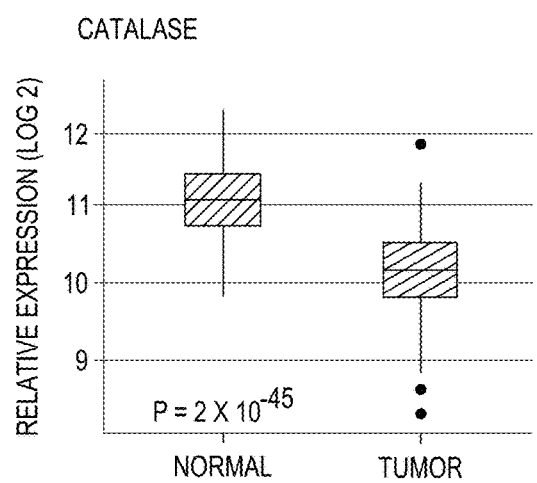
Figure 47F:
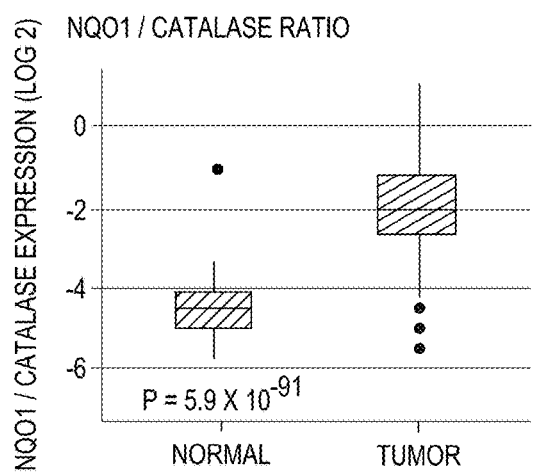
Figure 47G:
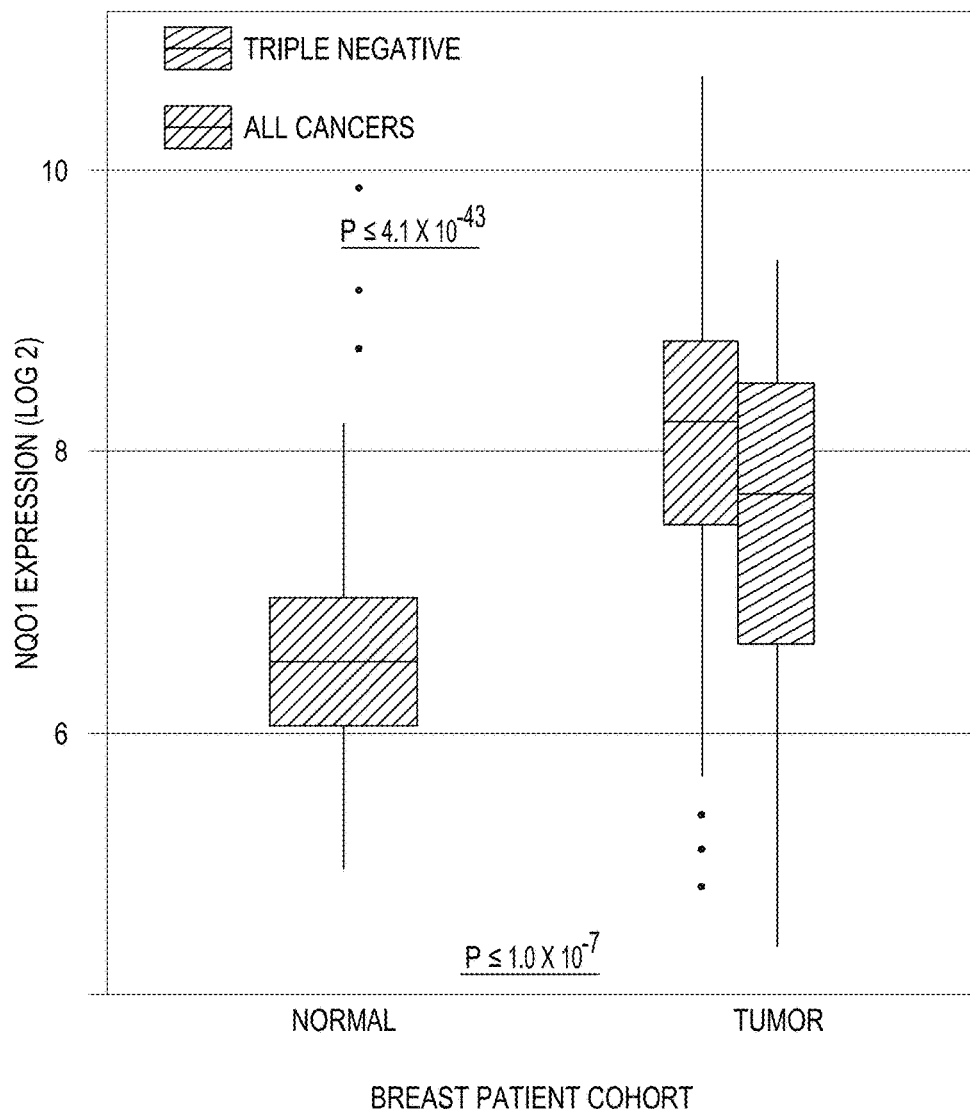
Figure 48A:
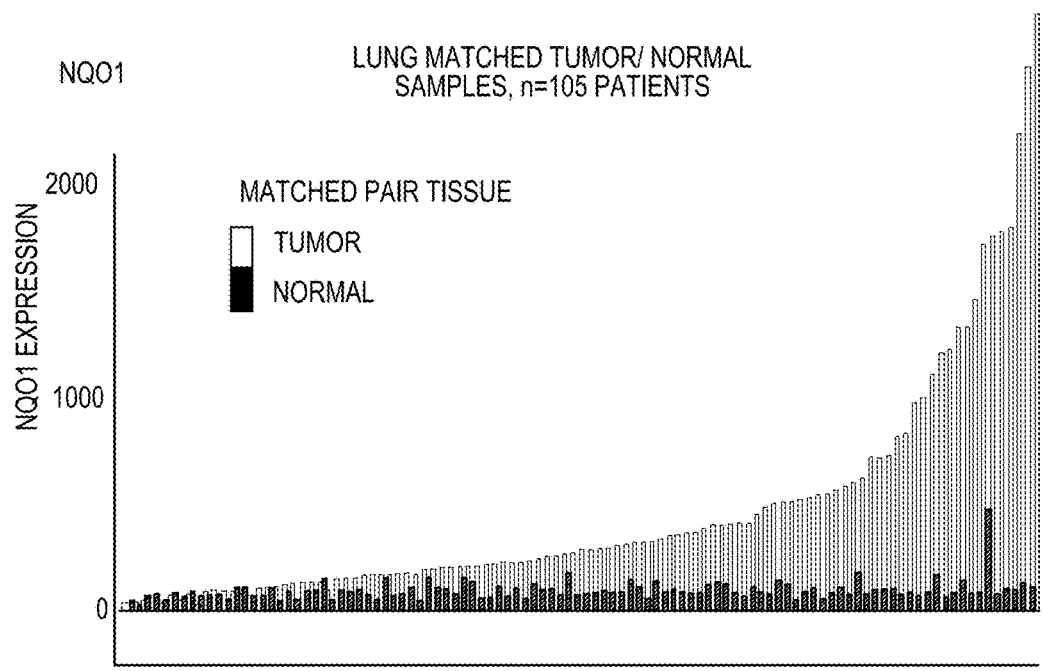
FIG. 48. NQO1 levels are also elevated in non-small cell lung cancers (NSCLCs) versus associated normal tissue (n=105) (A), whereas Catalase is elevated in Normal tissue and lower levels are found in NSCLC tumors (B). (C)-(E) expression and sample counts.
Figure 48B:
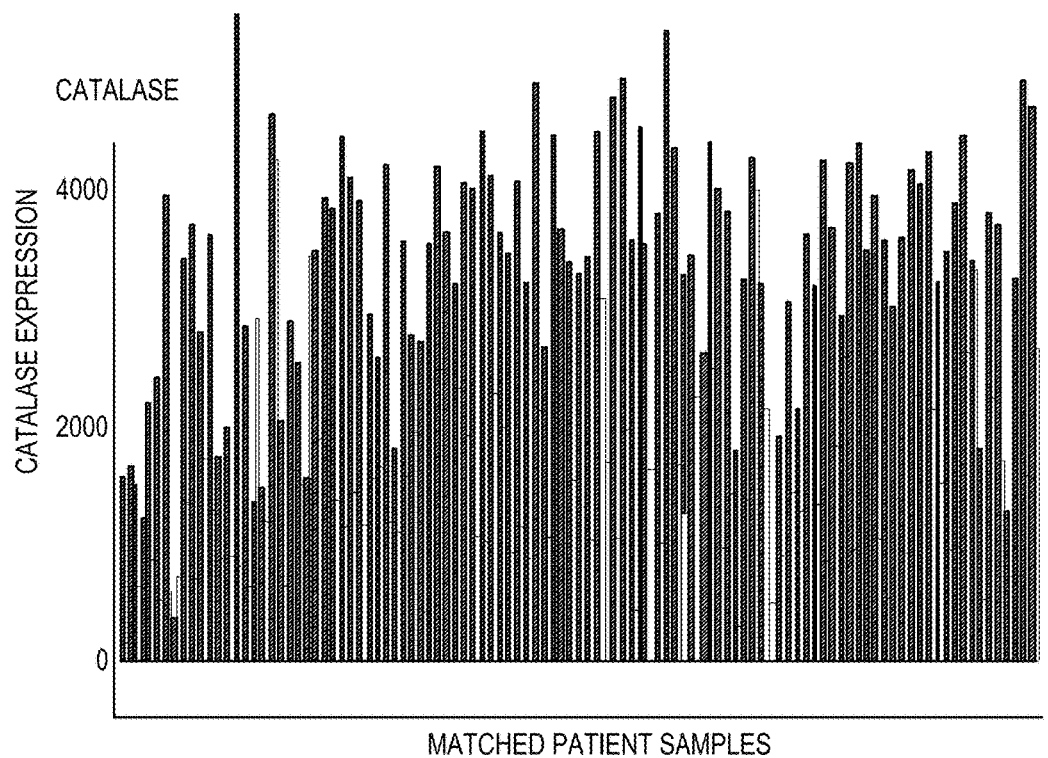
Figure 48C:
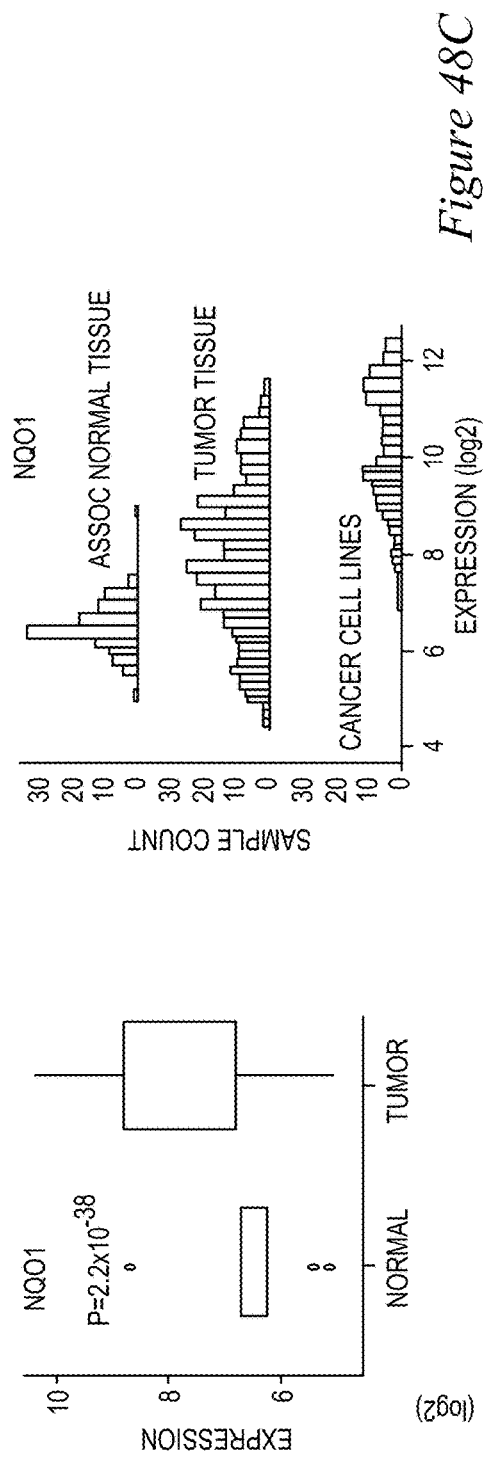
Figure 48D:
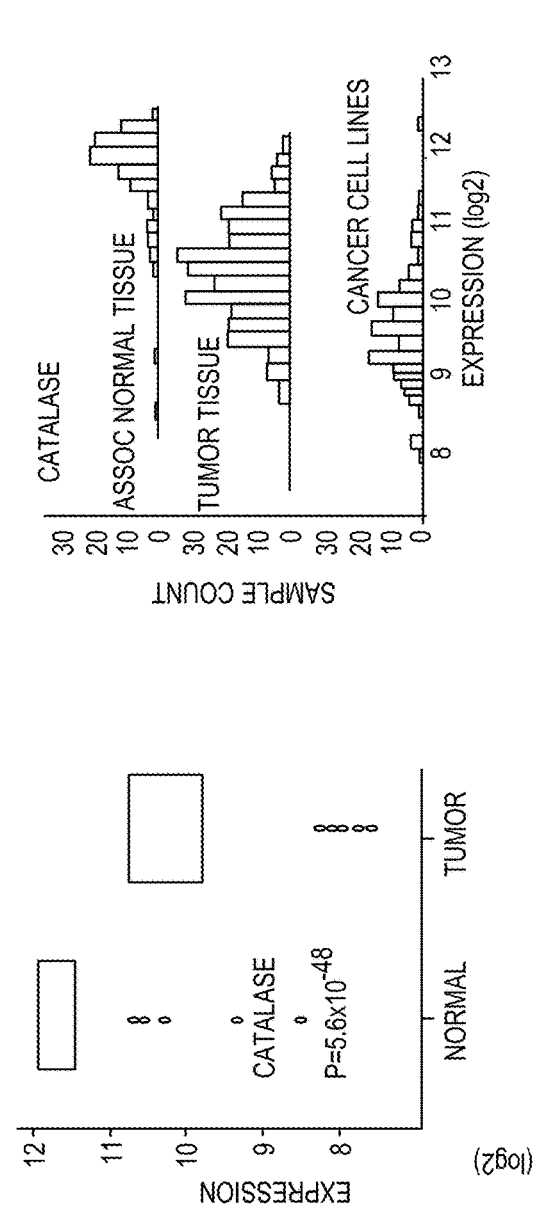
Figure 48E:
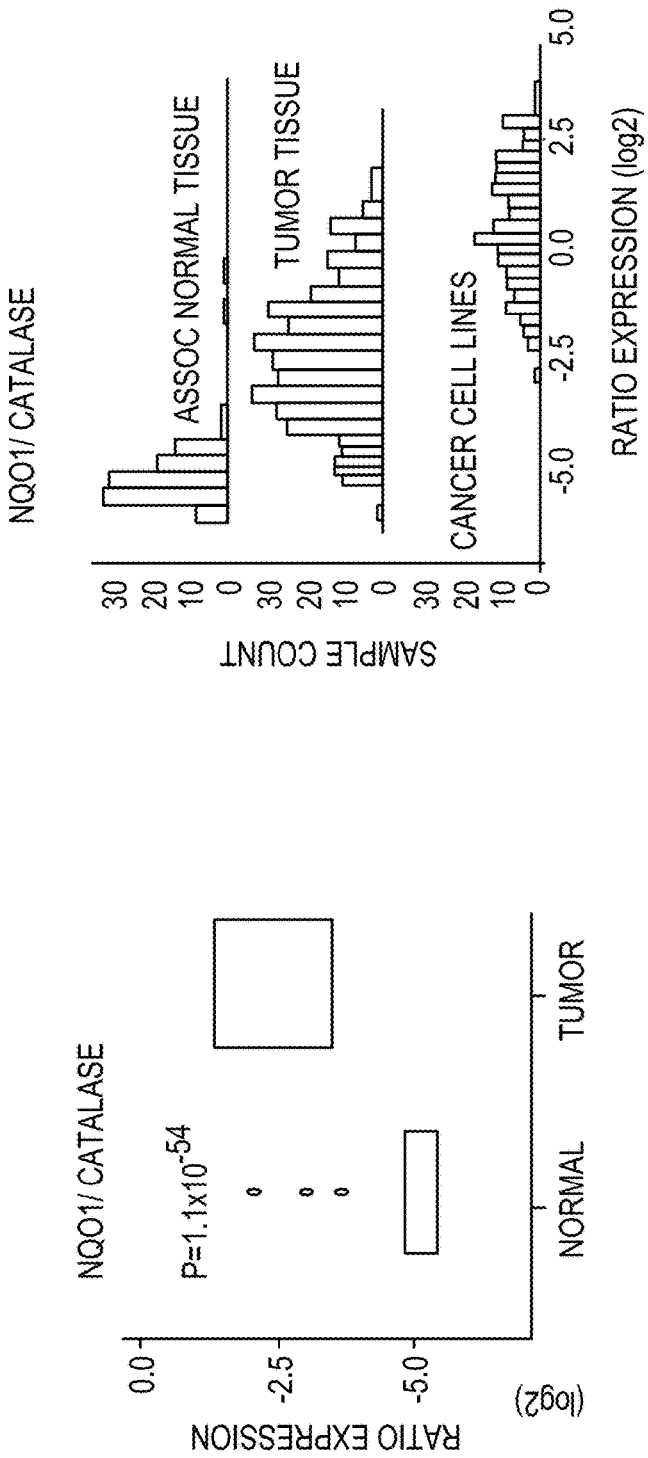

A459 NSCLC cells were pretreated with 15 μM AG014699 for 2 hours, then exposed to the same concentration of AG014699+various concentrations of DNQ87 for 2 hours as indicated (FIG. 45). Cells were then washed free of drug and relative survival performed as previously described (Huang et al., *Cancer Res.*, 2012). Cells treated in this manner by nontoxic doses of ß-lap show enhanced DNA lesion formation, equivalent to DNA lesions formed by a lethal dose of ß-lap (8 μM, 2 hours) (FIG. 46).

Figure 49:
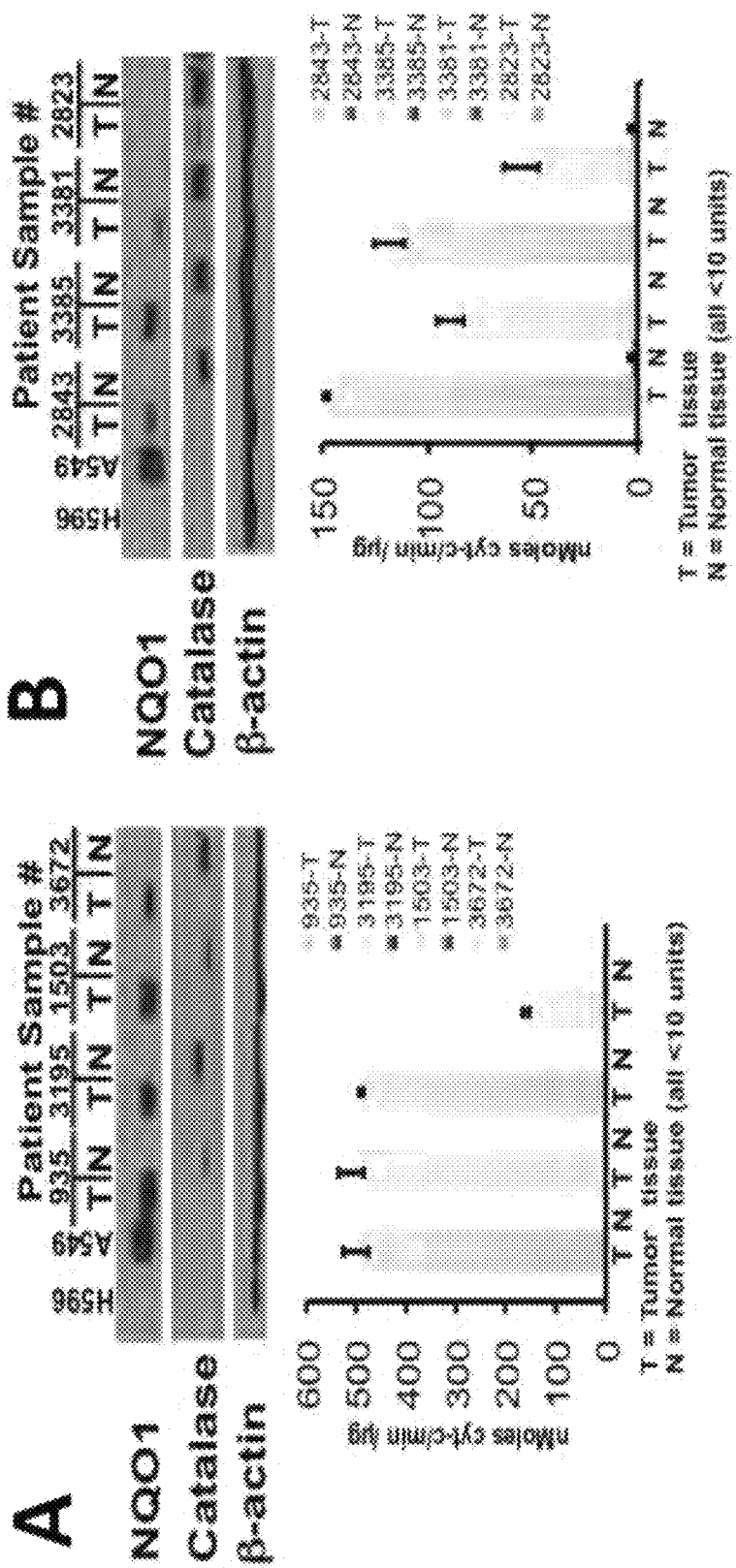
FIG. 49. NQO1/Catalase ratios in tumor versus normal tissue in human NSCLC patient samples.

Catalase Ratio Calculations. FIG. 1 shows NQO1/Catalase levels in matched (n=59) (A,B), as well as batched human pancreatic tumor vs. associated normal tissues. Importantly, NQO1 is required to 'bioactivate' DNQ and ß-lapachone and their analogs that are substrates for the enzyme, whereas Catalase is the one known resistance free radical scavenging enzyme that can protect against these drugs. Note that NQO1 ratios are very high in tumor tissue, yet low in associated normal tissue (E,H). FIG. 47 shows that NQO1/Catalase ratios are elevated in breast cancer tumors, but low in associated normal tissue (C, F). Triple-negative (ER-, PR- and HR-) human breast cancer cells are also elevated in NQO1 levels compared to associated normal tissue. FIG. 48 shows that NQO1 levels are also elevated in non-small cell lung cancers (NSCLCs) versus associated normal tissue (n=105) (A), whereas Catalase is elevated in Normal tissue and lower levels are found in NSCLC tumors (B). Similar to pancreatic and breast cancer versus normal tissue, the NQO1/Catalase ratios are elevated in tumor and lower levels found in normal tissue. Note that NQO1 levels are also elevated in prostate cancers (Dong et al., Cancer Res., 2010), although catalase levels were not assessed in that particular study. The data of FIG. 49 provides validation in human NSCLC patient samples of the NQO1/Catalase ratios in tumor versus normal tissue.

Example 3. Pharmaceutical Dosage Forms

The following formulations illustrate representative pharmaceutical dosage forms that may be used for the therapeutic or prophylactic administration of a compound of a formula described herein (e.g., DNQ or a DNQ compound, or β-Lap or a β-Lap derivative), a compound specifically disclosed herein, a pharmaceutically acceptable salt or solvate thereof, or a combination of compounds described herein (hereinafter referred to as 'Compound X'):

| (i) Tablet 1 | mg/tablet |
|---|---|
| 'Compound X' | 10.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 210.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. The compounds described herein may also be delivered in combination with delivery systems such as nanoparticles, micelles, or liposomes. Additionally, the specific ingredients and proportions are for illustrative purposes. Ingredients may be exchanged for suitable equivalents and proportions may be varied, according to the desired properties of the dosage form of interest.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be recognized by one of skill in the art, methods and devices useful for the present methods can include a large number of optional composition and processing elements and steps.

Although the present invention has been described with reference to certain embodiments thereof, other embodiments are possible without departing from the present invention. Although the description herein contains a plurality of specificities, these should not be construed as limiting the scope of the invention but as merely providing illustrations of some of the presently preferred embodiments of the invention. The spirit and scope of the appended claims should not be limited, therefore, to the description of any specific embodiments contained herein. All embodiments that come within the meaning of the claims, either literally or by equivalence are intended to be embraced therein. Furthermore, the advantages described above are not necessarily the only advantages of the invention, and it is not necessarily expected that all of the described advantages will be achieved with every embodiment of the invention.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). References cited herein are incorporated by reference to indicate the state of the art as of their publication or filing date and it is intended that this information can be employed herein, if needed, to exclude specific embodiments that are in the prior art. For example, when compounds are claimed generically, it should be understood that compounds known and available in the art prior to Applicant's invention, including compounds for which an enabling disclosure is provided in the references cited herein, are not intended to be included in the compounds claims herein.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

What is claimed is:

1. A method of killing or inhibiting the growth of cancer cells of a solid tumor in a patient in need thereof comprising administering to said patient a NQO1 bioactivatable drug in combination with administration of a poly(ADP-ribosyl) polymerase I (PARP1) inhibitor, wherein the NQO1 bioactivatable drug is administered at least about 2 hours after the PARP1 inhibitor, wherein the NQO1 bioactivatable drug is deoxynyboquinone (DNQ)

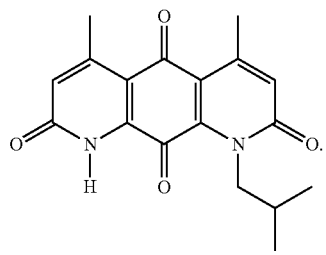 [SMILES: Cc1cc(=O)[nH]c2c1C(=O)c1c(C)cc(=O)n(CC(C)C)c1C2=O]

2. The method of claim 1, wherein the cancer cells have base excision repair (BER) defects or vulnerabilities due to faulty DNA repair processes.

3. The method of claim 2, wherein the BER defect or vulnerability comprises defective levels of X-ray cross complementing 1 (XRCC1) RNA or protein.

4. The method of claim 1, further comprising the administration of a DNA damaging agent.

5. The method of claim 1, further comprising administration of an additional chemotherapeutic agent or radiotherapy.

6. The method of claim 1, wherein the cancer cells have elevated levels of NQO1.

7. The method of claim 1, wherein the cancer cells are non-small cell lung cancer cells, prostate cancer cells, pancreatic cancer cells, breast cancer cells, head and neck cancer cells, or colon cancer cells.

8. The method of claim 1, wherein the NQO1 bioactivatable drug is DNQ.

9. The method of claim 1, wherein the NQO1 bioactivatable drug is

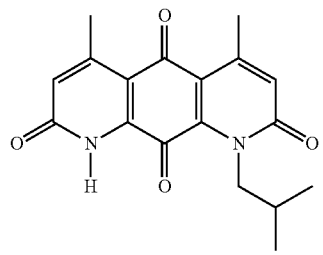 [SMILES: Cc1cc(=O)[nH]c2c1C(=O)c1c(C)cc(=O)n(CC(C)C)c1C2=O]

10. The method of claim 1, wherein said administering comprises contacting the cancer cell with an effective amount of an NQO1 bioactivatable drug in combination with a poly(ADP-ribosyl) polymerase I (PARP1) inhibitor, thereby killing or inhibiting the growth of the cancer cell.

11. The method of claim 1, wherein the NQO1 bioactivatable drug is administered at least about 24 hours, 28 hours, about 31 hours, about 35 hours, about 38 hours, about 42 hours, about 45 hours, about 2 days, about 3 days, about 4 days, about 5 days, about 6 days, about 8 days, about 9 days, about 12 days, about 15 days, about 16 days, about 18 days, or about 20 days after administration of the PARP1 inhibitor.

12. The method of claim 1, wherein the NQO1 bioactivatable drug is administered at about 1 day to about 21 days after administration of the PARP1 inhibitor.

13. The method of claim 1, wherein the NQO1 bioactivatable drug is DNQ and the PARP1 inhibitor is selected from the group consisting of AG-014699 (Rucaparib), ABT-888 (Veliparib), BSI-201 (Iniparib), AZD2281 (Olaparib), AG14361 and INO-1001.

14. The method of claim 1, wherein the NQO1 bioactivatable drug is

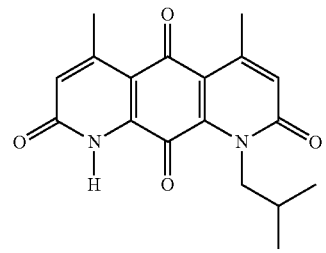 [SMILES: Cc1cc(=O)[nH]c2c1C(=O)c1c(C)cc(=O)n(CC(C)C)c1C2=O]

and the PARP1 inhibitor is selected from the group consisting of AG-014699 (Rucaparib), ABT-888 (Veliparib), BSI-201 (Iniparib), AZD2281 (Olaparib), AG14361 and INO-1001.

15. The method of claim 1, wherein the NQO1 bioactivatable drug is

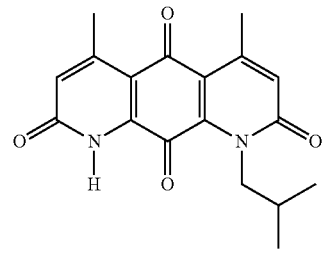 [SMILES: Cc1cc(=O)[nH]c2c1C(=O)c1c(C)cc(=O)n(CC(C)C)c1C2=O]

and the PARP1 inhibitor is Rucaparib.

16. The method of claim 1, wherein the NQO1 bioactivatable drug is

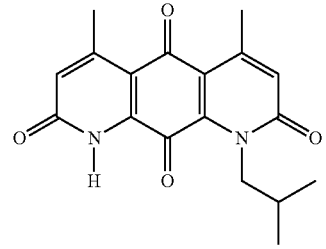 [SMILES: Cc1cc(=O)[nH]c2c1C(=O)c1c(C)cc(=O)n(CC(C)C)c1C2=O]

and the PARP1 inhibitor is Veliparib.

17. The method of claim 1, wherein the NQO1 bioactivatable drug is

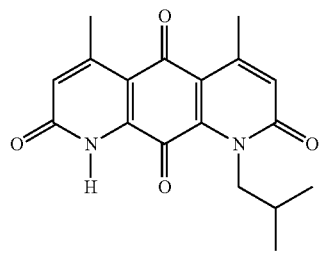 [SMILES: Cc1cc(=O)[nH]c2c1C(=O)c1c(C)cc(=O)n(CC(C)C)c1C2=O]
and the PARP1 inhibitor is Olaparib.
18. The method of claim 1, wherein the NQO1 bioactivatable drug is DNQ, and the PARP1 inhibitor is Rucaparib.
19. The method of claim 1, wherein the NQO1 bioactivatable drug is DNQ, and the PARP1 inhibitor is Veliparib.
20. The method of claim 1, wherein the NQO1 bioactivatable drug is DNQ, and the PARP1 inhibitor is Olaparib.
* * * * *

UNITED STATES PATENT AND TRADEMARK OFFICE
CERTIFICATE OF CORRECTION

PATENT NO. : 10,272,099 B2  
APPLICATION NO. : 14/783344  
DATED : April 30, 2019  
INVENTOR(S) : Paul J. Hergenrother et al.

It is certified that error appears in the above-identified patent and that said Letters Patent is hereby corrected as shown below:

In the Claims

In Claim 1, Column 47, Line 22, insert --(DNQ-87)-- after the chemical drawing.

In Claim 9, Column 47, Line 57, insert --(DNQ-87)-- after the chemical drawing.

In Claim 14, Column 48, Line 27, insert --(DNQ-87)-- after the chemical drawing.

In Claim 15, Column 48, Line 47, insert --(DNQ-87)-- after the chemical drawing.

In Claim 16, Column 48, Line 63, insert --(DNQ-87)-- after the chemical drawing.

In Claim 17, Column 49, Line 12, insert --(DNQ-87)-- after the chemical drawing.

Signed and Sealed this  
Sixth Day of August, 2019

Andrei Iancu  
*Director of the United States Patent and Trademark Office*